US011287427B2

(12) United States Patent
Powers et al.

(10) Patent No.: US 11,287,427 B2
(45) Date of Patent: Mar. 29, 2022

(54) APPLICATION OF ANTI-CD39L3 ANTIBODIES FOR USE IN DISEASE DIAGNOSTICS AND IMAGING

(71) Applicants: VANDERBILT UNIVERSITY, Nashville, TN (US); THE UNITED STATES AS REPRESENTED BY THE DEPARTMENT OF VETERANS AFFAIRS, Washington, DC (US)

(72) Inventors: Alvin C. Powers, Brentwood, TN (US); Marcela Brissova, Nashville, TN (US); Chunhua Dai, Nashville, TN (US); Neil Phillips, Lawrenceville, GA (US); Diane Saunders, Nashville, TN (US)

(73) Assignees: VANDERBILT UNIVERSITY, Nashville, TN (US); THE UNITED STATES AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 16/620,747

(22) PCT Filed: Jun. 11, 2018

(86) PCT No.: PCT/US2018/036856
§ 371 (c)(1),
(2) Date: Dec. 9, 2019

(87) PCT Pub. No.: WO2018/227176
PCT Pub. Date: Dec. 13, 2018

(65) Prior Publication Data
US 2020/0191787 A1    Jun. 18, 2020

Related U.S. Application Data

(60) Provisional application No. 62/517,728, filed on Jun. 9, 2017.

(51) Int. Cl.
*G01N 33/573* (2006.01)
*A61K 35/39* (2015.01)
(Continued)

(52) U.S. Cl.
CPC ....... *G01N 33/56966* (2013.01); *A61K 35/39* (2013.01); *C07K 16/40* (2013.01);
(Continued)

(58) Field of Classification Search
CPC ....... G01N 33/56966; G01N 33/54313; G01N 33/54326; G01N 33/573; G01N 2800/042; C07K 16/40; A61K 35/39
See application file for complete search history.

(56) References Cited

U.S. PATENT DOCUMENTS

2003/0124721 A1* 7/2003 Cheatham ............ A61P 1/18
                                                      435/366
2006/0246006 A1* 11/2006 Johnson .......... A61K 49/0004
                                                      424/9.6
2015/0118158 A1   4/2015 Jensen et al.

OTHER PUBLICATIONS

Syed et al. Ectonucleotidase NTPDase3 is abundant in pancreatic β-cells and regulates glucose-induced insulin secretion. Am J Physiol Endocrinol Metab 305: E1319-E1326 (2013)—IDS.*
(Continued)

*Primary Examiner* — Gailene Gabel
(74) *Attorney, Agent, or Firm* — Meunier Carlin & Curfman LLC

(57) ABSTRACT

In spite of significant efforts to identify β-cell-specific markers for β-cell imaging and purification, progress has been limited. Herein is disclosed a novel biomarker of human pancreatic β-cells, CD39L3 (also known as ecto-nucleoside triphosphate diphosphohydrolase-3 (NTP-
(Continued)

Dase3)). Disclosed are compositions and methods for purifying and imaging β-cell using anti-CD39L3 antibodies.

3 Claims, 19 Drawing Sheets

Specification includes a Sequence Listing.

(51) Int. Cl.
    G01N 33/569    (2006.01)
    C07K 16/40     (2006.01)
    G01N 33/543    (2006.01)

(52) U.S. Cl.
    CPC . *G01N 33/54313* (2013.01); *G01N 33/54326* (2013.01); *G01N 33/573* (2013.01); *G01N 2500/10* (2013.01); *G01N 2800/042* (2013.01)

(56) References Cited

OTHER PUBLICATIONS

Dorrell et al. Isolation of major pancreatic cell types and long-term culture-initiating cells using novel human surface markers (Stem Cell Research 1: 183-194 (2008)—IDS.*
Weir et al. Islet β cell mass in diabetes and how it relates to function, birth, and death. Annal of the New York Academy of Sciences. 1281: 92-105 (2013).*
Gutierrez et al. Heterogeneity of the Pancreatic Beta Cell. Frontiers in Genetics 8 (22): 1-9 (Mar. 2017).*
International Search Report and Written Opinion dated Aug. 10, 2018, from International Application No. PCT/US2018/036856, 12 pages.
Aamodt, K. I. et al. Development of a reliable automated screening system to identify small molecules and biologies that promote human β-cell regeneration. American Journal of Physiology—Endocrinology and Metabolism 311, E859-E868 (2016).
Abdulreda, M. H., Caicedo, A. & Berggren, P.-O. Transplantation into the anterior chamber of the eye for longitudinal, non-invasive in vivo imaging with single-cell resolution in real-time. J Vis Exp e50466 (2013). doi: 10.3791/50466.
Ahlgren U, Gotthardt M. Approaches for imaging islets: recent advances and future prospects. Adv Exp Med Biol. 2010;654:39-57.
Antonioli, L., Blandizzi, C., Csóka, B., Pacher, P. & Haskó, G. Adenosine signalling in diabetes mellitus—pathophysiology and therapeutic considerations. Nature Reviews Endocrinology 11, 228-241 (2015).
Balamurugan, A. N., Chang, Y., Fung, J. J., Trucco, M. & Bottino, R. Flexible management of enzymatic digestion improves human islet isolation outcome from sub-optimal donor pancreata. Am. J. Transplant. 3, 1135-1142 (2003).
Blodgett, D. M. et al. Novel Observations From Next-Generation RNA Sequencing of Highly Purified Human Adult and Fetal Islet Cell Subsets. Diabetes 64, 3172-3181 (2015).
Bonner-Weir S, Trent DF, Weir GC. Partial pancreatectomy in the rat and subsequent defect in glucose-induced insulin release. The Journal of clinical investigation. 1983;71(6):1544-53.
Bonner-Weir S. Life and death of the pancreatic beta cells. Trends Endocrinol Metab. 2000;11(9):375-8.
Bramswig, N. C. et al. Epigenomic plasticity enables human pancreatic α to β cell reprogramming. J. Clin. Invest. 123, 1275-1284 (2013).
Brissova M, Fowler M, Wiebe P, Shostak A, Shiota M, Radhika A, et al. Intraislet endothelial cells contribute to revascularization of transplanted pancreatic islets. Diabetes. 2004;53(5):1318-25.
Brissova M, Shiota M, Nicholson WE, Gannon M, Knobel SM, Piston DW, et al. Reduction in pancreatic transcription factor PDX-1 impairs glucose-stimulated insulin secretion. The Journal of biological chemistry. 2002;277(13):11225-32.

Brissova M, Shostak A, Shiota M, Wiebe PO, Poffenberger G, Kantz J, et al. Pancreatic islet production of vascular endothelial growth factor—a is essential for islet vascularization, revascularization, and function. Diabetes. 2006;55(11):2974-85.
Brissova, M. et al. a Cell Function and Gene Expression Are Compromised in Type 1 Diabetes. Cell Reports 22, 1-11 (2018).
Brissova, M. et al. Islet microenvironment, modulated by vascular endothelial growth factor—A signaling, promotes β cell regeneration. Cell Metabolism 19, 498-511 (2014).
Brom M, Andralojc K, Oyen WJ, Boerman OC, Gotthardt M. Development of radiotracers for the determination of the beta-cell mass in vivo. Curr Pharm Des. 2010;16(14):1561-7.
Butler AE, Janson J, Bonner-Weir S, Ritzel R, Rizza RA, Butler PC. Beta-cell deficit and increased beta-cell apoptosis in humans with type 2 diabetes. Diabetes. 2003;52(1):102-10.
Chaudhari AJ, Darvas F, Bading JR, Moats RA, Conti PS, Smith DJ, et al. Hyperspectral and multispectral bioluminescence optical tomography for small animal imaging. Physics in medicine and biology. 2005;50(23):5421-41.
Clark PB, Gage HD, Brown-Proctor C, Buchheimer N, Calles-Escandon J, Mach RH, et al. Neurofunctional imaging of the pancreas utilizing the cholinergic PET radioligand [18F]4-fluorobenzyltrozamicol. European journal of nuclear medicine and molecular imaging. 2004;31(2):258-60.
Coutinho-Silva, R., Parsons, M., Robson, T. & Burnstock, G. Changes in expression of P2 receptors in rat and mouse pancreas during development and ageing. Cell Tissue Res 306, 373-383 (2001).
Coutinho-Silva, R., Parsons, M., Robson, T., Lincoln, J. & Burnstock, G. P2X and P2Y purinoceptor expression in pancreas from streptozotocin-diabetic rats. Molecular and Cellular Endocrinology 204, 141-154 (2003).
Davalli AM, Ogawa Y, Scaglia L, Wu YJ, Hollister J, Bonner-Weir S, et al. Function, mass, and replication of porcine and rat islets transplanted into diabetic nude mice. Diabetes. 1995;44(1):104-11.
Davalli AM, Scaglia L, Zangen DH, Hollister J, Bonner-Weir S, Weir GC. Early changes in syngeneic islet grafts: effect of recipient's metabolic control on graft outcome. Transplant Proc. 1995;27(6):3238-9.
De la Tour D, Halvorsen T, Demeterco C, Tyrberg B, Itkin-Ansari P, Loy M, et al. Beta-cell differentiation from a human pancreatic cell line in vitro and in vivo. Molecular endocrinology (Baltimore, Md. 2001;15(3):476-83.
Dehghani H, Davis SC, Jiang S, Pogue BW, Paulsen KD, Patterson MS. Spectrally resolved bioluminescence optical tomography. Optics letters. 2006;31(3):365-7.
Dehghani H, Davis SC, Pogue BW. Spectrally resolved bioluminescence tomography using the reciprocity approach. Medical physics. 2008;35(11):4863-71.
Dehghani H, Eames ME, Yalavarthy PK, Davis SC, Srinivasan S, Carpenter CM, et al. Near infrared optical tomography using NIRFAST: Algorithm for numerical model and image reconstruction. Communications in numerical methods in engineering. 2008;25(6):711-32.
Dillies, M.-A. et al. A comprehensive evaluation of normalization methods for Illumina high-throughput RNA sequencing data analysis. Brief. Bioinformatics 14, 671-683 (2013).
Dorrell C, Abraham SL, Lanxon-Cookson KM, Canaday PS, Streeter PR, Grompe M. Isolation of major pancreatic cell types and long-term culture-initiating cells using novel human surface markers. Stem cell research. 2008;1(3):183-94.
Dorrell, C. et al. Human islets contain four distinct subtypes of β cells. Nat Commun 7, 11756 (2016).
Dorrell, C. et al. Isolation of mouse pancreatic alpha, beta, duct and acinar populations with cell surface markers. Molecular and Cellular Endocrinology 339, 144-150 (2011).
Dorrell, C. et al. Transcriptomes of the major human pancreatic cell types. Diabetologia 54, 2832-2844 (2011).
Eisenbarth GS, Shimizu K, Bowring MA, Wells S. Expression of receptors for tetanus toxin and monoclonal antibody A2B5 by pancreatic islet cells. Proceedings of the National Academy of Sciences of the United States of America. 1982;79(16):5066-70.

(56) References Cited

OTHER PUBLICATIONS

Enge, M. et al. Single-Cell Analysis of Human Pancreas Reveals Transcriptional Signatures of Aging and Somatic Mutation Patterns. Cell 171, 321-330.e14 (2017).
Eriksson O, Jahan M, Johnstrom P, Korsgren O, Sundin A, Halldin C, et al. In vivo and in vitro characterization of [18F]-FE-(+)-DTBZ as a tracer for beta-cell mass. Nuclear medicine and biology. 2010;37(3):357-63.
Eriksson, O. et al. In vivo imaging of beta cells with radiotracers: state of the art, prospects and recommendations for development and use. Diabetologia 59, 1340-1349 (2016).
Fagerholm V, Mikkola KK, Ishizu T, Arponen E, Kauhanen S, Nagren K, et al. Assessment of islet specificity of dihydrotetrabenazine radiotracer binding in rat pancreas and human pancreas. J Nucl Med. 2010;51(9): 1439-46.
Fowler M, Virostko J, Chen Z, Poffenberger G, Radhika A, Brissova M, et al. Assessment of pancreatic islet mass after islet transplantation using in vivo bioluminescence imaging. Transplantation. 2005;79(7):768-76.
Gepts W, Lecompte PM. The pancreatic islets in diabetes. The American journal of medicine. 1981;70(1):105-15.
Gepts W. Pathologic anatomy of the pancreas in juvenile diabetes mellitus. Diabetes. 1965;14(10):619-33.
Goland R, Freeby M, Parsey R, Saisho Y, Kumar D, Simpson N, et al. 11C-dihydrotetrabenazine PET of the pancreas in subjects with long-standing type 1 diabetes and in healthy controls. J Nucl Med. 2009;50(3):382-9.
Gotthardt M, Boermann OC, Behr TM, Behe MP, Oyen WJ. Development and clinical application of peptide-based radiopharmaceuticals. Curr Pharm Des. 2004;10(24):2951-63.
Gotthardt M. Beta cell imaging—why we need it and what has been achieved. Curr Pharm Des. 2010;16(14):1545-6.
Hampe CS, Wallen AR, Schlosser M, Ziegler M, Sweet IR. Quantitative evaluation of a monoclonal antibody and its fragment as potential markers for pancreatic beta cell mass. Exp Clin Endocrinol Diabetes. 2005;1113(7):381-7.
Hanley SC, Austin E, Assouline-Thomas B, Kapeluto J, Blaichman J, Moosavi M, et al. {beta}-Cell mass dynamics and islet cell plasticity in human type 2 diabetes. Endocrinology. 2010;151(4):1462-72.
Haque, A., Engel, J., Teichmann, S. A. & Lönnberg, T. A practical guide to single-cell RNA-sequencing for biomedical research and clinical applications. Genome Med 9, 1-12 (2017).
Holliger P, Hudson PJ. Engineered antibody fragments and the rise of single domains. Nature biotechnology. 2005;23(9):1126-36.
Huang, D. W. et al. Extracting biological meaning from large gene lists with DAVID. Curr Protoc Bioinformatics Chapter 13, Unit 13.11-13.11.13 (2009).
Hutton JC, Davidson HW. Getting beta all the time: discovery of reliable markers of beta cell mass. Diabetologia. 2010;53(7):1254-7.
Imai K, Takaoka A. Comparing antibody and small-molecule therapies for cancer. Nature reviews. 2006;6(9):714-27.
Itkin-Ansari P, Geron I, Hao E, Demeterco C, Tyrberg B, Levine F. Cell-based therapies for diabetes: progress towards a transplantable human beta cell line. Annals of the New York Academy of Sciences. 2003;1005:138-47.
Kaplan EL, Meier P. Nonparametric Estimation from Incomplete Observations. Journal of the American Statistical Association. 1958;53(282):457-81.
Kayton, N. S. et al. Human islet preparations distributed for research exhibit a variety of insulin-secretory profiles. American Journal of Physiology—Endocrinology and Metabolism 308, E592-602 (2015).
Khan, S. et al. Autocrine activation of P2Y1 receptors couples Ca2+ influx to Ca2+ release in human pancreatic beta cells. Diabetologia 57, 2535-2545 (2014).
Kobayashi H, Sakahara H, Endo K, Yao ZS, Toyama S, Konishi J. Repeating the avidin "chase" markedly improved the biodistribution of radiolabelled biotinylated antibodies and promoted the excretion of additional background radioactivity. Eur J Cancer. 1995;31A(10):1689-96.
Kume E, Fujimura H, Matsuki N, Ito M, Aruga C, Toriumi W, et al. Hepatic changes in the acute phase of streptozotocin (SZ)-induced diabetes in mice. Exp Toxicol Pathol. 2004;55(6):467-80.
Ladriere L, Leclercq-Meyer V, Malaisse WJ. Assessment of islet beta-cell mass in isolated rat pancreases perfused with D-[(3)H]mannoheptulose. Am J Physiol Endocrinol Metab. 2001;281(2):E298-303.
Ladriere L, Malaisse-Lagae F, Alejandro R, Malaisse WJ. Pancreatic fate of a (125)I-labelled mouse monoclonal antibody directed against pancreatic B-cell surface ganglioside(s) in control and diabetic rats. Cell Biochem Funct. 2001;19(2):107-15.
Larsen MO, Gotfredsen CF, Wilken M, Carr RD, Porksen N, Rolin B. Loss of betacell mass leads to a reduction of pulse mass with normal periodicity, regularity and entrainment of pulsatile insulin secretion in Gottingen minipigs. Diabetologia. 2003;46(2):195-202.
Laurent, D. et al. Pancreatic β-cell imaging in humans: fiction or option? Diabetes Obes Metab 18, 6-15 (2015).
Lavoie, E. G. et al. Identification of the ectonucleotidases expressed in mouse, rat, and human Langerhans islets: potential role of NTPDase3 in insulin secretion. American Journal of Physiology—Endocrinology and Metabolism 299, E647-56 (2010).
Liu CB, Liu GZ, Liu N, Zhang YM, He J, Rusckowski M, et al. Radiolabeling morpholinos with 90Y, 111In, 188Re and 99mTc. Nuclear medicine and biology. 2003;30(2):207-14.
Liu G, Dou S, Chen X, Chen L, Liu X, Rusckowski M, et al. Adding a clearing agent to pretargeting does not lower the tumor accumulation of the effector as predicted. Cancer bio therapy & radiopharmaceuticals. 2010;25(6):757-62.
Liu G, Dou S, He J, Liu X, Rusckowski M, Hnatowich DJ. Predicting the biodistribution of radiolabeled cMORF effector in MORF-pretargeted mice. European journal of nuclear medicine and molecular imaging. 2007;34(2):237-46.
Liu G, Dou S, Pretorius PH, Liu X, Chen L, Rusckowski M, et al. Tumor pretargeting in mice using MORF conjugated CC49 antibody and radiolabeled complimentary cMORF effector. Q J Nucl Med Mol Imaging. 2009.
Liu G, He J, Dou S, Gupta S, Rusckowski M, Hnatowich DJ. Further investigations of morpholino pretargeting in mice—establishing quantitative relations in tumor. European journal of nuclear medicine and molecular imaging. 2005;32(9):1115-23.
Liu G, Hnatowich DJ. A semiempirical model of tumor pretargeting. Bioconjugate chemistry. 2008;19(11):2095-104.
Liu G, Liu C, Zhang S, He J, Liu N, Gupta S, et al. Investigations of 99mTc morpholino pretargeting in mice. Nuclear medicine communications. 2003;24(6):697-705.
Liu G, Mang'era K, Liu N, Gupta S, Rusckowski M, Hnatowich DJ. Tumor pretargeting in mice using (99m)Tc-labeled morpholino, a DNA analog. J Nucl Med. 2002;43(3):384-91.
Liu G, Zhang C, Liu F, Wang R, Fu Z, Li G, et al. 99mTc-N,N'-bis(aminoethyl)propanediamine hexaacetic acid (BPHA): a glomerular filtration agent similar to 99mTc-DTPA. Nuclear medicine and biology. 2002;29(4):399-404.
Liu G, Zhang S, He J, Zhu Z, Rusckowski M, Hnatowich DJ. Improving the Tabeling of S-acetyl NHS-MAG(3)-conjugated morpholino oligomers. Bioconjugate chemistry. 2002;13(4):893-7.
Liu, S. & Trapnell, C. Single-cell transcriptome sequencing: recent advances and remaining challenges. F1000Res 5, 1-9 (2016).
Maes F, Collignon A, Vandermeulen D, Marchal G, Suetens P. Multimodality image registration by maximization of mutual information. IEEE transactions on medical imaging. 1997;16(2):187-98.
Malaisse WJ, Doherty M, Ladriere L, Malaisse-Lagae F. Pancreatic uptake of [2-(14)C]alloxan. Int J Mol Med. 2001;7(3):311-5.
Malaisse WJ, Ladriere L. Assessment of B-cell mass in isolated islets exposed to D-[3H]mannoheptulose. Int J Mol Med. 2001;7(4):405-6.
Malone, J. H. & Oliver, B. Microarrays, deep sequencing and the true measure of the transcriptome. BMC Biol. 9, 34 (2011).

(56) References Cited

OTHER PUBLICATIONS

McCulloch DK, Koerker DJ, Kahn SE, Bonner-Weir S, Palmer JP. Correlations of in vivo beta-cell function tests with beta-cell mass and pancreatic insulin content in streptozocin-administered baboons. Diabetes. 1991;40(6):673-9.

Moore A, Bonner-Weir S, Weissleder R. Noninvasive in vivo measurement of beta-cell mass in mouse model of diabetes. Diabetes. 2001;50(10):2231-6.

Munkonda, M. N. et al. Characterization of a monoclonal antibody as the first specific inhibitor of human NTP diphosphohydrolase-3. FEBS Journal 276, 479-496 (2009).

Nyman LR, Wells KS, Head WS, McCaughey M, Ford E, Brissova M, et al. Real-time, multidimensional in vivo imaging used to investigate blood flow in mouse pancreatic islets. The Journal of clinical investigation. 2008;118(11):3790-7.

Olafsen T, Wu AM. Antibody vectors for imaging. Seminars in nuclear medicine. 2010;40(3):167-81.

Olafsen, T. & Wu, A. M. Antibody Vectors for Imaging. YSNUC 40, 167-181 (2010).

Otonkoski T, Nanto-Salonen K, Seppanen M, Veijola R, Huopio H, Hussain K, et al. Noninvasive Diagnosis of Focal Hyperinsulinism of Infancy With [18F]-DOPA Positron Emission Tomography. Diabetes. 2006;55(1):13-8.

Parnaud, G. et al. Proliferation of sorted human and rat beta cells. Diabetologia 51, 91-100 (2008).

Petit, P., Lajoix, A.-D. & Gross, R. P2 purinergic signalling in the pancreatic β-cell Control of insulin secretion and pharmacology. European Journal of Pharmaceutical Sciences 37, 67-75 (2009).

Powers AC, Rabizadeh A, Akeson R, Eisenbarth GS. Characterization of monoclonal antibody 3G5 and utilization of this antibody to immobilize pancreatic islet cell gangliosides in a solid phase radioassay. Endocrinology. 1984;114(4):1338-43.

Rahier J, Guiot Y, Goebbels RM, Sempoux C, Henquin JC. Pancreatic beta-cell mass in European subjects with type 2 diabetes. Diabetes, obesity & metabolism. 2008;10 Suppl 4:32-42.

Chandra, et al., RFX6 Regulates Insulin Secretion by Modulating Ca2+ Homeostasis in Human β Cells. Cell Reports 9, 2206-2218 (2014).

Robertson RP. Estimation of beta-cell mass by metabolic tests: necessary, but how sufficient? Diabetes. 2007;56(10):2420-4.

Robinson, M. D. & Oshiack, A. A scaling normalization method for differential expression analysis of RNA-seq data. Genome Biol. 11, R25 (2010).

Robson, S. C., Sévigny, J. & Zimmermann, H. The E-NTPDase family of ectonucleotidases: Structure function relationships and pathophysiological significance. Purinergic Signal. 2, 409-430 (2006).

Sadoff L. Nephrotoxicity of streptozotocin (NSC-85998). Cancer chemotherapy reports. 1970;54(6):457-9.

Saito K, Yaginuma N, Takahashi T. Differential volumetry of A, B and D cells in the pancreatic islets of diabetic and nondiabetic subjects. The Tohoku journal of experimental medicine. 1979;129(3):273-83.

Schmitz A, Shiue CY, Feng Q, Shiue GG, Deng S, Pourdehnad MT, et al. Synthesis and evaluation of fluorine-18 labeled glyburide analogs as beta-cell imaging agents. Nuclear medicine and biology. 2004;31(4):483-91.

Schneider S, Feilen PJ, Schreckenberger M, Schwanstecher M, Schwanstecher C, Buchholz HG, et al. In vitro and in vivo evaluation of novel glibenclamide derivatives as imaging agents for the non-invasive assessment of the pancreatic islet cell mass in animals and humans. Exp Clin Endocrinol Diabetes. 2005;113(7):388-95.

Segerstolpe, Å. et al. Single-Cell Transcriptome Profiling of Human Pancreatic Islets in Health and Type 2 Diabetes. Cell Metabolism 24, 593-607 (2016).

Silva, A. M. et al. Electrophysiological and immunocytochemical evidence for P2X purinergic receptors in pancreatic beta cells. Pancreas 36, 279-283 (2008).

Simpson NR, Souza F, Witkowski P, Maffei A, Raffo A, Herron A, et al. Visualizing pancreatic beta-cell mass with [11C]DTBZ. Nuclear medicine and biology. 2006;33(7):855-64.

Souza F, Simpson N, Raffo A, Saxena C, Maffei A, Hardy M, et al. Longitudinal noninvasive PET-based beta cell mass estimates in a spontaneous diabetes rat model. The Journal of clinical investigation. 2006;116(6):1506-13.

Speier, S. et al. Noninvasive high-resolution in vivo imaging of cell biology in the anterior chamber of the mouse eye. Nat Protoc 3, 1278-1286 (2008).

Speier, S. et al. Noninvasive in vivo imaging of pancreatic islet cell biology. Nature Medicine 14, 574-578 (2008).

Sweet IR, Cook DL, Lernmark A, Greenbaum CJ, Krohn KA. Non-invasive imaging of beta cell mass: a quantitative analysis. Diabetes Technol Ther. 2004;6(5):652-9.

Sweet IR, Cook DL, Lernmark A, Greenbaum CJ, Wallen AR, Marcum ES, et al. Systematic screening of potential beta-cell imaging agents. Biochem Biophys Res Commun. 2004;314(4):976-83.

Syed, S. K. et al. Ectonucleotidase NTPDase3 is abundant in pancreatic β-cells and regulates glucose-induced insulin secretion. American Journal of Physiology—Endocrinology and Metabolism 305, E1319-26 (2013).

Thorel F, Nepote V, Avril I, Kohno K, Desgraz R, Chera S, et al. Conversion of adult pancreatic alpha-cells to beta-cells after extreme beta-cell loss. Nature. 2010;464(7292):1149-54.

Trapnell, C., Pachter, L. & Salzberg, S. L. TopHat: discovering splice junctions with RNA-Seq. Bioinformatics 25, 1105-1111 (2009).

Virostko J, Chen Z, Fowler M, Poffenberger G, Powers AC, Jansen ED. Factors influencing quantification of in vivo bioluminescence imaging: application to assessment of pancreatic islet transplants. Mol Imaging. 2004;3(4):333-42.

Virostko J, Jansen ED, Powers AC. Current status of imaging pancreatic islets. Current diabetes reports. 2006;6(4):328-32.

Virostko J, Powers AC, Jansen ED. Validation of luminescent source reconstruction using single-view spectrally resolved bioluminescence images. Applied optics. 2007;46(13):2540-7.

Virostko J, Powers AC. Molecular imaging of the pancreas in small animal models. Gastroenterology. 2009;136(2):407-9.

Virostko J, Radhika A, Poffenberger G, Chen Z, Brissova M, Gilchrist J, et al. Bioluminescence imaging in mouse models quantifies beta cell mass in the pancreas and after islet transplantation. Mol Imaging Biol. 2010;12(1):42-53.

Virostko J, Xie J, Hallahan DE, Arteaga CL, Gore JC, Manning HC. A molecular imaging paradigm to rapidly profile response to angiogenesis-directed therapy in small animals. Mol Imaging Biol. 2009;11(3):204-12.

Wangler B, Schneider S, Thews O, Schirrmacher E, Comagic S, Feilen P, et al. Synthesis and evaluation of (S)-2-(2-[18F]fluoroethoxy)-4-([3-methyl-1-(2-piperidin-1-yl-phenyl)-butyl-carbamoyl]-methyl)-benzoic acid ([18F]repaglinide): a promising radioligand for quantification of pancreatic beta-cell mass with positron emission tomography (PET). Nuclear medicine and biology. 2004;31(5):639-47.

Wu AM. Antibodies and antimatter: the resurgence of immuno-PET. J Nucl Med. 2009;50(1):2-5.

Wuttke, A., Idevall-Hagren, O. & Tengholm, A. P2Y$_1$ receptor-dependent diacylglycerol signaling microdomains in β cells promote insulin secretion. FASEB J 27, 1610-1620 (2013).

Xin, Y. et al. RNA Sequencing of Single Human Islet Cells Reveals Type 2 Diabetes Genes. Cell Metabolism 24, 608-615 (2016).

Zimmermann, H., Zebisch, M. & Sträter, N. Cellular function and molecular structure of ecto-nucleotidases. Purinergic Signal. 8, 437-502 (2012).

International Preliminary Report on Patentability issued for Application No. PCT/US2018/036856, dated Dec. 19, 2019.

* cited by examiner

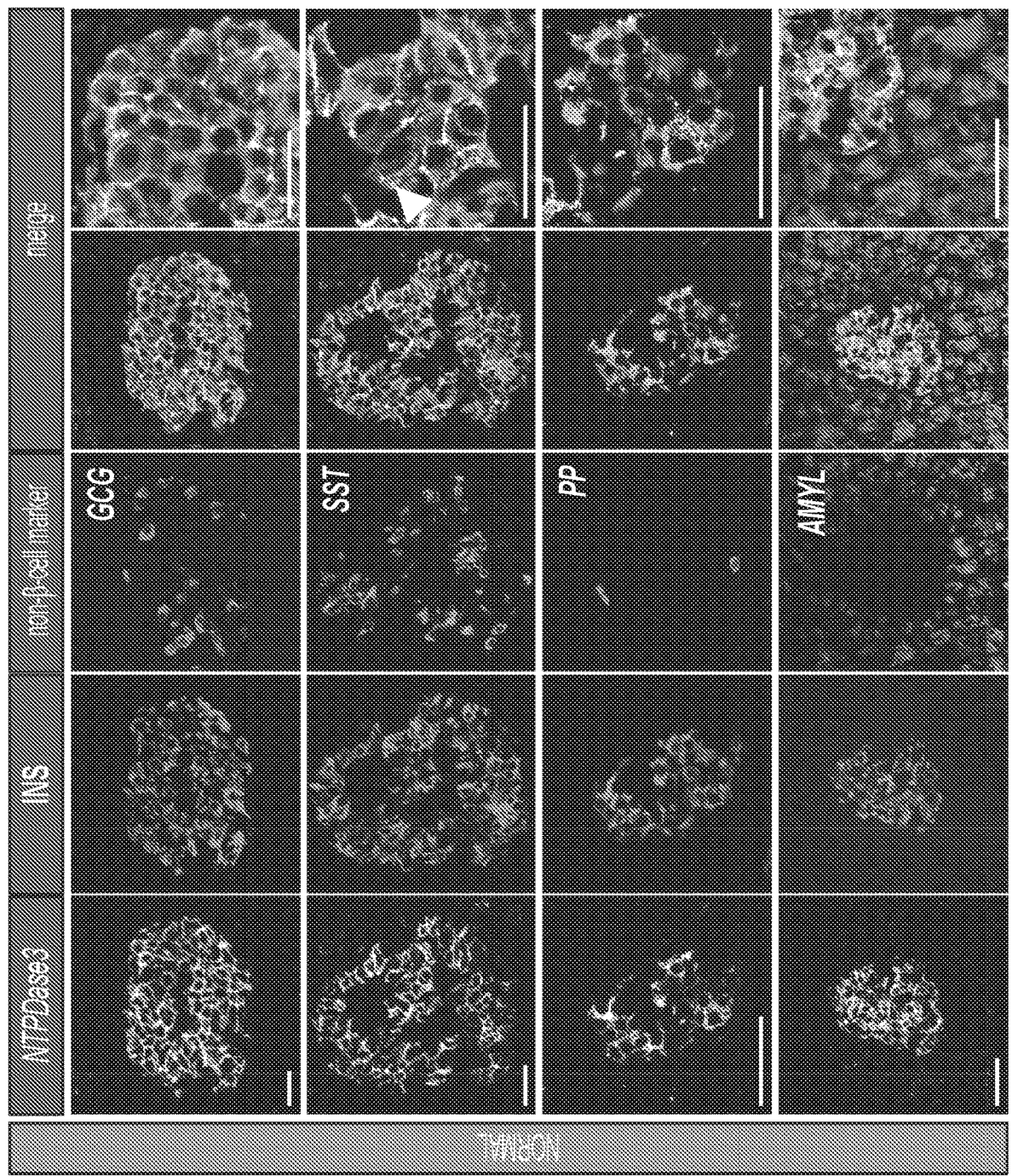

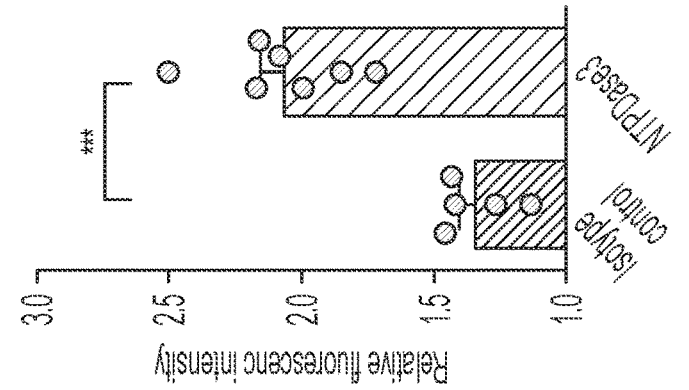
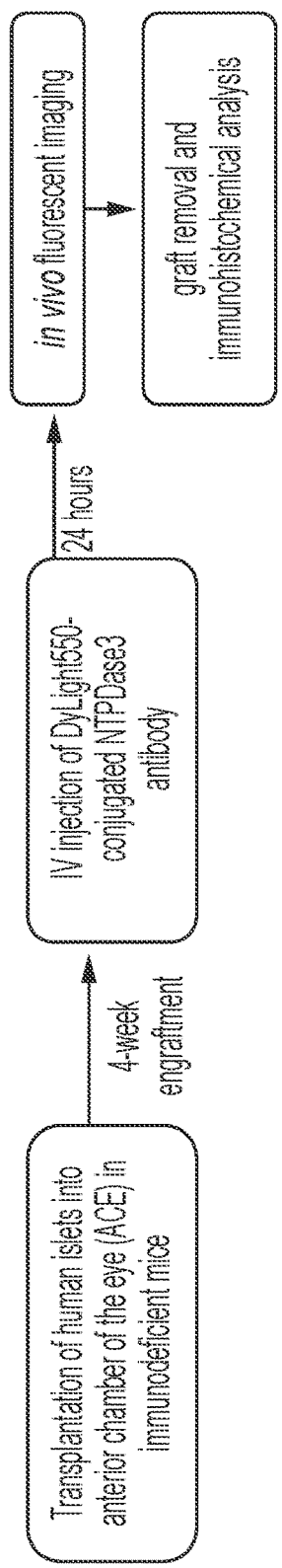
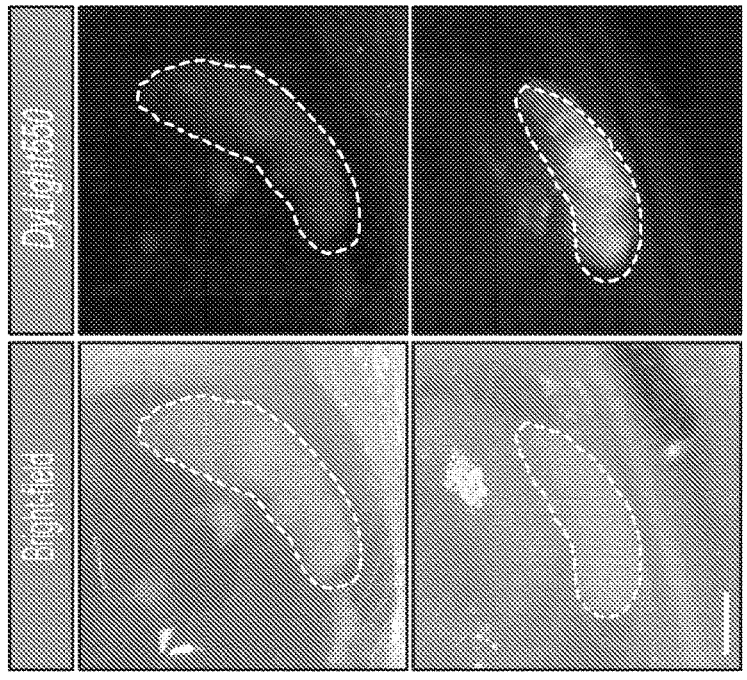
FIG. 6A
FIG. 6B
FIG. 6C

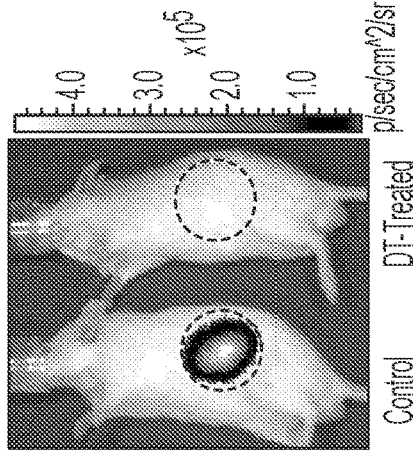
FIG. 9A
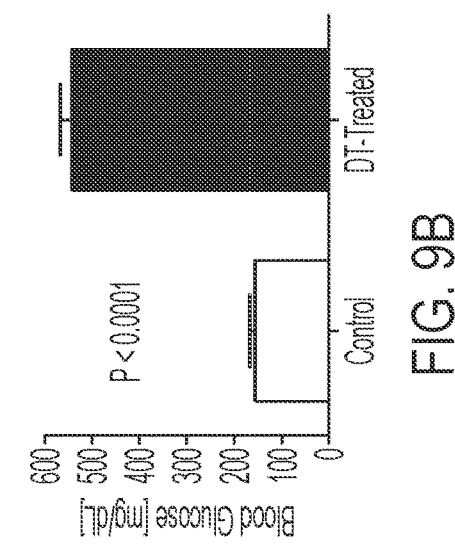
FIG. 9B
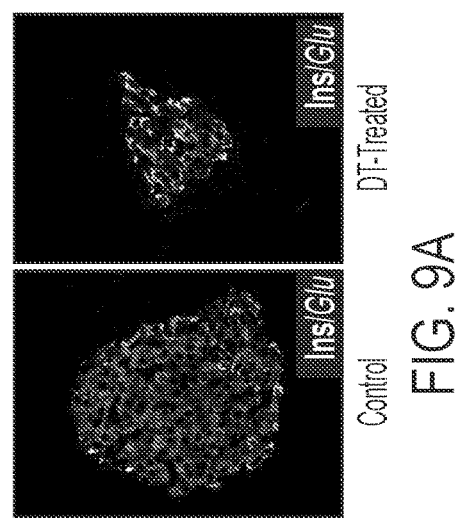
FIG. 9C
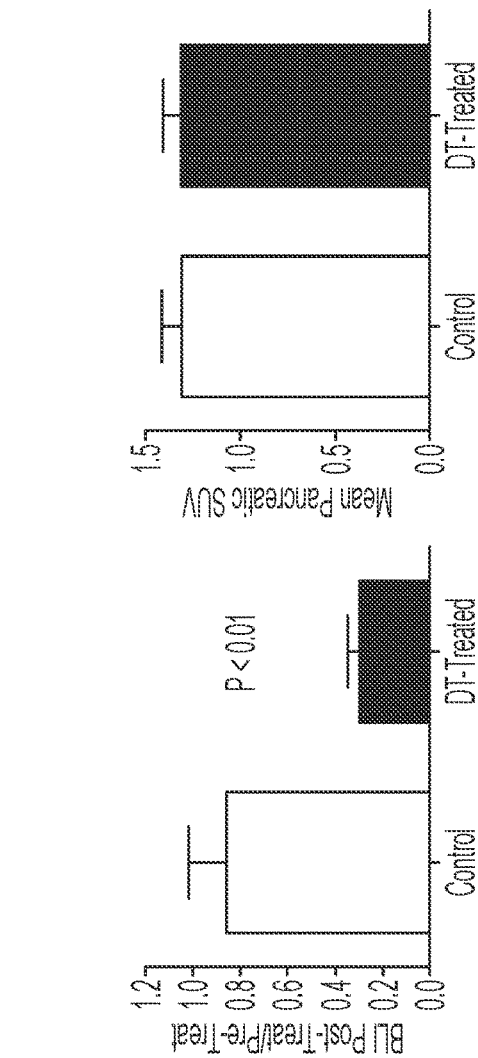
FIG. 9D
FIG. 9E
FIG. 9F

SEQUENCE LISTING

<160> NUMBER OF SEQ ID NOS: 2

<210> SEQ ID NO 1
<211> LENGTH: 529
<212> TYPE: PRT
<213> ORGANISM: Homo sapiens

<400> SEQUENCE: 1

Met Phe Thr Val Leu Thr Arg Gln Pro Cys Glu Gln Ala Gly Leu Lys
1               5                   10                  15

Ala Leu Tyr Arg Thr Pro Thr Ile Ile Ala Leu Val Val Leu Leu Val
            20                  25                  30

Ser Ile Val Val Leu Val Ser Ile Thr Val Ile Gln Ile His Lys Gln
        35                  40                  45

Glu Val Leu Pro Pro Gly Leu Lys Tyr Gly Ile Val Leu Asp Ala Gly
    50                  55                  60

Ser Ser Arg Thr Thr Val Tyr Val Tyr Gln Trp Pro Ala Glu Lys Glu
65                  70                  75                  80

Asn Asn Thr Gly Val Val Ser Gln Thr Phe Lys Cys Ser Val Lys Gly
                85                  90                  95

Ser Gly Ile Ser Ser Tyr Gly Asn Asn Pro Gln Asp Val Pro Arg Ala
            100                 105                 110

Phe Glu Glu Cys Met Gln Lys Val Lys Gly Gln Val Pro Ser His Leu
            115                 120                 125

His Gly Ser Thr Pro Ile His Leu Gly Ala Thr Ala Gly Met Arg Leu
            130                 135                 140

Leu Arg Leu Gln Asn Glu Thr Ala Ala Asn Glu Val Leu Glu Ser Ile
145                 150                 155                 160

Gln Ser Tyr Phe Lys Ser Gln Pro Phe Asp Phe Arg Gly Ala Gln Ile
                165                 170                 175

Ile Ser Gly Gln Glu Gly Val Tyr Gly Trp Ile Thr Ala Asn Tyr
            180                 185                 190

Leu Met Gly Asn Phe Leu Glu Lys Asn Leu Trp His Met Trp Val His
            195                 200                 205

Pro His Gly Val Glu Thr Thr Gly Ala Leu Asp Leu Gly Gly Ala Ser
            210                 215                 220

Thr Gln Ile Ser Phe Val Ala Gly Glu Lys Met Asp Leu Asn Thr Ser
225                 230                 235                 240

Asp Ile Met Gln Val Ser Leu Tyr Gly Tyr Val Tyr Thr Leu Tyr Thr
                245                 250                 255

His Ser Phe Gln Cys Tyr Gly Arg Asn Glu Ala Glu Lys Lys Phe Leu
            260                 265                 270

Ala Met Leu Leu Gln Asn Ser Pro Thr Lys Asn His Leu Thr Asn Pro
            275                 280                 285

Cys Tyr Pro Arg Asp Tyr Ser Ile Ser Phe Thr Met Gly His Val Phe
            290                 295                 300

Asp Ser Leu Cys Thr Val Asp Gln Arg Pro Glu Ser Tyr Asn Pro Asn
305                 310                 315                 320

Asp Val Ile Thr Phe Glu Gly Thr Gly Asp Pro Ser Leu Cys Lys Glu
                325                 330                 335

Lys Val Ala Ser Ile Phe Asp Phe Lys Ala Cys His Asp Gln Glu Thr
            340                 345                 350

Cys Ser Phe Asp Gly Val Tyr Gln Pro Lys Ile Lys Gly Pro Phe Val
            355                 360                 365

Ala Phe Ala Gly Phe Tyr Tyr Thr Ala Ser Ala Leu Asn Leu Ser Gly
            370                 375                 380

Ser Phe Ser Leu Asp Thr Phe Asn Ser Ser Thr Trp Asn Phe Cys Ser
385                 390                 395                 400

Gln Asn Trp Ser Gln Leu Pro Leu Leu Pro Lys Phe Asp Glu Val
                405                 410                 415

Tyr Ala Arg Ser Tyr Cys Phe Ser Ala Asn Tyr Ile Tyr His Leu Phe
            420                 425                 430

Val Asn Gly Tyr Lys Phe Thr Glu Glu Thr Trp Pro Gln Ile His Phe
            435                 440                 445

Glu Lys Glu Val Gly Asn Ser Ser Ile Ala Trp Ser Leu Gly Tyr Met
            450                 455                 460

Leu Ser Leu Thr Asn Gln Ile Pro Ala Glu Ser Pro Leu Ile Arg Leu
465                 470                 475                 480

Pro Ile Glu Pro Pro Val Phe Val Gly Thr Leu Ala Phe Phe Thr Ala
                485                 490                 495

Ala Ala Leu Leu Cys Leu Ala Phe Leu Ala Tyr Leu Cys Ser Ala Thr
            500                 505                 510

Arg Arg Lys Arg His Ser Glu His Ala Phe Asp His Ala Val Asp Ser
    515                 520                 525

Asp

<210> SEQ ID NO 2
<211> LENGTH: 2797
<212> TYPE: DNA
<213> ORGANISM: Homo sapiens

<400> SEQUENCE: 2

| | | | | | |
|---|---|---|---|---|---|
| acccacgcgt | ctggccgcgg | gccgcctctg | cggcagcgct | agtcgccttc | tccgaatcgg | 60 |
| ctccgcacag | ctaggagaaa | agatgttcac | tgtgctgacc | cgccaaccat | gtgagcaagc | 120 |
| aggcctcaag | gccctctacc | gaactccaac | catcattgcc | ttggtggtct | tgcttgtgag | 180 |
| tattgtggta | cttgtgagta | tcactgtcat | ccagatccac | aagcaagagg | tcctccctcc | 240 |
| aggactgaag | tatggtattg | tgctggatgc | cgggtcttca | agaaccacag | tctacgtgta | 300 |
| tcaatggcca | gcagaaaaag | agaataatac | cggagtggtc | agtcaaacct | tcaaatgtag | 360 |
| tgtgaaaggc | tctggaatct | ccagctatgg | aaataacccc | caagatgtcc | ccagagcctt | 420 |
| tgaggagtgt | atgcaaaaag | tcaaggggca | ggttccatcc | cacctccacg | gatccacccc | 480 |
| cattcacctg | ggagccacgg | ctgggatgcg | cttgctgagg | ttgcaaaatg | aaacagcagc | 540 |
| taatgaagtc | cttgaaagca | tccaaagcta | cttcaagtcc | cagcccttg | actttagggg | 600 |
| tgctcaaatc | atttctgggc | aagaagaagg | ggtatatgga | tggattacag | ccaactattt | 660 |
| aatgggaaat | ttcctggaga | gaacctgtg | gcacatgtgg | gtgcacccgc | atggagtgga | 720 |
| aaccacgggt | gccctggact | taggtggtgc | ctccacccaa | atatccttcg | tggcaggaga | 780 |
| gaagatggat | ctgaacacca | gcgacatcat | gcaggtgtcc | ctgtatgct | acgtatacac | 840 |
| gctctacaca | cacagcttcc | agtgctatgg | ccggaatgag | gctgagaaga | gtttctggc | 900 |
| aatgctcctg | cagaattctc | ctaccaaaaa | ccatctcacc | aatccctgtt | accctcggga | 960 |
| ttatagcatc | agcttcacca | tgggccatgt | atttgatagc | ctgtgcactg | tggaccagag | 1020 |
| gccagaaagt | tataaccca | atgatgtcat | cactttttgaa | ggaactgggg | acccatctct | 1080 |
| gtgtaaggag | aaggtggctt | ccatatttga | cttcaaagct | tgccatgatc | aagaaacctg | 1140 |
| ttcttttgat | ggggtttatc | agccaaagat | taagggcca | tttgtggctt | ttgcaggatt | 1200 |
| ctactacaca | gccagtgctt | taaatctttc | aggtagcttt | tccctggaca | ccttcaactc | 1260 |
| cagcacctgg | aatttctgct | cacagaattg | gagtcagctc | ccactgctgc | tccccaaatt | 1320 |
| tgatgaggta | tatgcccgct | cttactgctt | ctcagccaac | tacatctacc | acttgtttgt | 1380 |
| gaacggttac | aaattcacag | aggagacttg | gccccaaata | cactttgaaa | agaagtggg | 1440 |
| gaatagcagc | atagcctggt | ctcttggcta | catgctcagc | ctgaccaacc | agatcccagc | 1500 |
| tgaaagccct | ctgatccgtc | tgcccataga | accacctgtc | tttgtgggca | ccctcgcttt | 1560 |
| cttcacagtg | gcagccttgc | tgtgtctggc | atttcttgca | tacctgtgtt | cagcaaccag | 1620 |
| aagaaagagg | cactccgagc | atgcctttga | ccatgcagtg | gattctgact | gagccttcaa | 1680 |
| agcagctcct | ggagtccaat | ggctgcttag | agtcagcctg | ggtggcacca | ggcaatgcag | 1740 |
| gtgaagtggc | tgccttcagg | aaatacaact | aactaaaatc | aaacacctag | gtcacgtgcc | 1800 |
| tctcaaatac | tgatttctgc | cacagcacct | cttgaggcat | cccttggcta | ttctgtgcat | 1860 |
| attgttcttc | agagacctca | ctacccacat | gctgatctat | ggggaacag | agaagagaca | 1920 |
| ggccactaag | gtcaggctct | ttatattaag | ttccccagag | gaagagtaag | ttgagaaggt | 1980 |

```
atcagtttaa tgttgaagaa ttgacctcag ggctcagttt ccatttccct ccctcagtat    2040
tcttcctggc aagatacccca ttaagcattt cgccaatcag aatctcattt tatagttttt    2100
cccattggtc tttaactaag actttcttgt agcaatctcg taagcagtga accccctcag    2160
atcagtagaa tatagtatct gggggagaag acttacttcc ttcagggcag cagccacagc    2220
caggcttctg tcatacaggt agatcccgaa gcacagagac ataaaaaagg tctcccagaa    2280
aactatagac cattctccaa gtggaattcc cacttagggc tctggtcact agattgcaac    2340
ctgtgtgttt gtcatcatcc tcatctcacc attgtattgc tatgccctcc cataaaaaca    2400
cattgatccc tagcaagatt attgcattcc agattttact gcctttgcta ggcttttgct    2460
tagcaaaggg ctgactttcc attgttatca tggtgtatat attttttgtca ccattcccac    2520 aagtatactt gatgttgtca tagaacgaac atcctactct atgatttact aaccaattac    2580
tttcccagat catagacctc tctgcatagt agtcataggt cttgactttg gggaaagaaa    2640
aggaagctgc aggaatattt atctccaaag tcgaatgaga aagaactcca gcaaatccaa    2700
tggctacaaa ctaaaaatca gcattatttc atattgctgt ttcttagctg aatatggaat    2760
aaagaactat tattttattt tgaaaaaaaa aaaaaaa                              2797
```

APPLICATION OF ANTI-CD39L3 ANTIBODIES FOR USE IN DISEASE DIAGNOSTICS AND IMAGING

CROSS REFERENCE TO RELATED APPLICATIONS

This application is a national stage application filed under 35 U.S.C. § 371 of PCT/US2018/036856, filed Jun. 11, 2018, which claims the benefit of U.S. Provisional Patent Application No. 62/517,728, filed on Jun. 9, 2017, applications which are incorporated herein by reference in their entirety.

BACKGROUND

Diabetes is a major health concern worldwide, and its growing prevalence poses an increasing demand for effective therapeutic and preventative approaches. The disease is broadly classified as type 1 or type 2, with both types characterized by dysfunction or destruction of insulin-secreting β-cells of the Islets of Langerhans. The highly vascularized, highly innervated islet functions as a mini-organ, and its heterogeneous composition and anatomical location pose challenges particularly to identifying characteristics of individual cell subtypes in normal or disease states. Approaches to noninvasively assay beta cell mass are greatly needed because being able to assess beta cell mass would lead to a better understanding of the pathogenesis of diabetes, provide an early diagnostic marker for type 1 and type 2 diabetes, and accelerate the development and evaluation of new therapies. For example, reduced beta cell mass is a cardinal feature of Type 1 diabetes and is now recognized as a critical feature in type 2 diabetes as well, but beta cell mass cannot be non-invasively quantified in humans. While the amount of insulin/C-peptide secreted following a glucose or meal challenge gives insight into insulin secretory capacity, these only indirectly reflect beta cell mass and cannot determine whether beta cell mass is improved or declining Additionally, glucose homeostasis is unaffected until beta cell mass is reduced to less than half its original value, presumably due to a large functional reserve capacity. Pancreatic islet mass can be accurately quantified by morphometric analysis of histological sections of the pancreas, but this requires removal of the pancreas. Thus, the time course of how both forms of diabetes develop is incompletely understood and this limits the ability to effectively test interventions to prevent beta cell loss or to increase beta cell mass in those with diabetes. Likewise, efforts to improve islet transplantation would greatly benefit from the ability to assess the number of islets surviving after transplantation.

Because of this, several groups have developed systems to isolate subpopulations of islet cells for transcriptional, metabolic, and functional analyses. These isolations are generally accomplished by dispersing and sorting cells using antibodies that target either cell surface antigens on live cells or intracellular proteins in fixed, permeabilized cells. Other groups have alternatively sorted β-cells based on zinc content, using the zinc-binding fluorochrome Newport Green. Each approach has advantages and drawbacks, but one critical limitation is the lack of a cell surface antibody that specifically targets human β-cells. What are needed are new targets and methods for detecting islet β cells in vivo and ex vivo.

SUMMARY

Disclosed are methods and compositions related to detecting islet β cells with anti-CD39L3 antibodies.

In one aspect, disclosed herein are method of non-invasively detecting islet β cell mass in a subject comprising a) administering to the subject an anti-CD39L3 antibody, nucleic acid probes specific for CD39, or labeled small molecules that target CD39; and b) assaying for the anti-CD39L3 antibody, nucleic acid probe, or small molecule, or detecting β-cells using more invasive methods comprising a) administering to the subject an anti-CD39L3 antibody, nucleic acid probes specific for CD39, or labeled small molecules that target CD39; b) obtaining a pancreatic tissue sample from the subject; and c) assaying for the anti-CD39L3 antibody nucleic acid probe, and/or small molecule.

Also disclosed are methods of any preceding aspect, wherein the administered anti-CD39L3 antibody is primary antibody conjugated to an unlabeled detectable marker.

Also disclosed are methods of any preceding aspect, wherein the unlabeled detectable marker is a biotin or a first morpholino.

Also disclosed are methods of any preceding aspect, wherein the method further comprises a secondary labeled antibody which is specific for conjugated marker on the primary antibody.

Also disclosed are methods of any preceding aspect, wherein the method further comprises a labeled complementary morpholino which is complementary to the first morpholino conjugated to the primary antibody.

In one aspect, disclosed herein are methods of isolating islet β-cells from a tissue sample from a subject comprising contacting the tissue sample with an anti-CD39L3 antibody, nucleic acid probe specific for CD39, or labeled small molecule that targets CD39, and separating the cells expressing CD39L3 using fluorescence activated cell sorting (FACS) or magnetic bead separation to detect cells bound by the CD39L3 antibody, nucleic acid probe, or labeled small molecule; wherein the cells expressing CD39L3 are islet β-cells.

Also disclosed herein are methods of treating diabetes in a subject comprising a) obtaining a pancreatic tissue sample from a donor; b) contacting the pancreatic tissue sample with a labeled anti-CD39L3 antibody, nucleic acid probe specific for CD39, or a labeled small molecule that targets CD39; wherein the anti-CD39L3 antibody binds to islet β-cells from the pancreatic tissue sample; c) isolating the islet β-cells using magnetic beads or fluorescence activated cell sorting; and d) transferring the isolated islet β-cells from the donor to the subject with diabetes.

In one aspect, disclosed herein are methods of detecting diabetes in a subject comprising contacting the islet β-cells of the subject with an anti-CD39L3 antibody nucleic acid probe specific for CD39, or a labeled small molecule that targets CD39, and measuring the mass of the islet β-cells; wherein a decrease in cell mass relative to a control indicates that a subject has diabetes.

Also disclosed are methods of any preceding aspect, wherein the islet β-cells are contacted with the CD39L3 antibody in vivo and the cell mass is assessed using one or more imaging method selected from bioluminescence (BLI), magnetic resonance imaging (MRI), Positron emission tomography (PET), Single photon emission computed tomography (SPECT), computed tomography (CT) scanning, and/or fluorescence molecular tomography (FMT).

Also disclosed are methods of any preceding aspect, wherein the islet β-cells are obtained from a tissue sample obtained from the subject and the islet β-cells are contacted with the anti-CD39L3 antibody ex vivo.

Also disclosed are methods of any preceding aspect, wherein the islet β-cell mass is assessed by an immunoassay selected from the group consisting of Radioimmunoassay (RIA), Enzyme-Linked Immunosorbent Assay (ELISA), Enzyme-Linked Immuno spot Assay (ELISPOT), Flow cytometry, fluorescence activated cell sorting (FACS), protein array, multiplexed bead assay, and magnetic capture.

In one aspect, disclosed herein are methods of testing the efficacy of an agent that is designed to increase islet β-cell mass comprising administering the agent to a subject; administering an anti-CD39L3 antibody, nucleic acid probe specific for CD39, or a labeled small molecule that targets CD39 to the subject; and measuring the mass of the islet β-cells in the subject by imaging or immunoassay, wherein an increase in the islet β-cell mass relative to a control indicates that the agent increases β-cell mass.

Also disclosed herein are methods of testing the efficacy of islet β-cell transplant comprising a) administering the agent to a subject isolated β-islet cells; b) administering an anti-CD39L3 antibody, nucleic acid probe specific for CD39, or labeled small molecule that targets CD39 to the subject, wherein the anti-CD39L3 antibody binds to islet βcells; and c) detecting the labeled islet β-cells in the subject by imaging or immunoassay.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows that NTPDase3 is expressed specifically in adult human β-cells.

FIGS. 2A, 2B, 2C, 2D, and 2E show expression of NTPDase3 in adult pancreatic endocrine and exocrine cells. NTPDase3 is not expressed in adult α-cells (labeled by GCG; 2A), PP cells (PP; 2C), or acinar cells (AMY; 2D). A small percentage of δ-cells (SST; 2B) express NTPDase3, as indicated by the white arrowhead. Sample is 18yM (see Table 1). FIG. 2E shows that in some islets during the period of infancy, NTPDase3 expression can be seen in both b-cells and surrounding acinar tissue. Arrowheads indicate the expression of non-endocrine cells. Scale bars in 2A, 2B, 2C, 2D, and 2E are 50 μm.

FIG. 3 shows that in some neonatal islets NTPDase3 expression can be seen both in β-cells and surrounding acinar tissue. Arrowheads indicate the expression in non-endocrine cells. Donor information is available in Table 1.

FIG. 4A shows the experimental overview of islet dispersion and sorting. FIG. 4B shows the separation of α- and β-cell subpopulations by flow cytometry. Indirect antibody labeling was used to preselect endocrine cells (HPi1$^+$) and subsequently identify α-cells (HPa3$^+$) and β-cells (NTPDase3$^+$). See Tables 2 and 3. FIG. 4C shows that FACS-collected islet cells were dispersed and stained, and cell populations were assessed by immunocytochemistry. Two independent islet preparations are shown; donor information is available in Table 1. Scale bar is 50 μm. FIGS. 4D and 4E show RNA-sequencing analysis of purified human α- and β-cells from normal adult donors (n=5; ages 26-55 years). FIG. 4D shows the principal component analysis (PCA) plot shows clustering of α- and β-cell samples. FIG. 4E shows the heat map of a selected gene subset shows relative gene expression in individual α- and β-cell samples.

FIGS. 6A, 6B, 6C, and 6D show targeting NTPDase3 detects human β-cells in vivo. FIG. 6A shows the experimental overview of human islet transplantation, antibody administration, and imaging. FIG. 6B shows bright-field images of islet grafts (outlined in white dashed lines) in the anterior chamber of the eye (ACE) of NSG mice receiving injections of DyLight550-conjugated antibody (left: isotype control, IgG2b-DyL550; right: NTPDase3-DyL550). Scale bar is 200 μm. FIG. 6C shows intensity in grafts of mice receiving injections of DyLight550-conjugated NTPDase3 antibody (n=7) or isotype control (n=5) was analyzed relative to background, ***, p=0.006. FIG. 6D shows immunohistochemistry on sections of islet grafts after removal from NSG mice. Secondary anti-mouse-Alexa488 antibody (left panel) recognized bound NTPDase3 antibody; DyLight550 signal (Cy3, second panel from left) remained intact following removal and fixation of grafts. Scale bar is 50 μm. Grafts pictured in 6B and 6C are from 61yM human islet donor (n=2 mice each, IgG2b-DyL550 and NTPDase3-DyL550); more information is available in Table 1.

FIG. 7A shows experimental overview of human islet transplantation, antibody administration, and immunohistochemical visualization. FIG. 7B shows a macro view of islet graft (outlined in dashed white line) and surrounding kidney tissue. Anti-mouse-cy3-conjugated secondary antibody shows NTPDase3 bound to human β-cells. FIG. 7C shows immunohistochemical detail of islet graft, as denoted by white box in (7B). Scale bars in 7B-7C are 50 μm. Transplanted islets are from 18yM (see Table 1).

FIG. 8A shows bright-field images of islet grafts (outlined in white dashed lines) in the anterior chamber of the eye (ACE) of NSG mice receiving injections of DyLight550-conjugated antibody (left: isotype control, IgG2b-DyLight550; right: NTPDase3-DyLight550). Scale bars are 200 µm. FIG. 8B shows immunohistochemistry on sections of islet grafts after removal from NSG mice. DyLight550 signal (first column from left, red) remained intact following graft removal and fixation. Secondary anti-mouse-Alexa488 antibody recognized bound NTPDase3 antibody (second column from left; green). DyLight550 and Alexa488 signals co-localized with insulin labeling (INS, blue). Sections were counterstained with nuclear dye DAPI (white). Scale bars are 50 µm and apply to all images in panel 8B. Donor information is available in Table 1.

FIGS. 9A, 9B, 9C, 9D, 9E, and 9F show that diphtheria toxin treatment ablates beta cells and bioluminescence signal in the MIP-Luc-VU/RIP-DTR mouse model, but not pancreatic PET radiotracer accumulation. FIG. 9A shows an islet from a control, untreated mouse (left) displays normal insulin-expressing beta (green) and glucagon-expressing alpha cells (red). After DT administration (right), an islet displays almost complete loss of beta cells (green), and the persistence of alpha cells (red). FIG. 9B shows that MIP-Luc-VU/RIP-DTR mice treated with DT exhibited significantly increased blood glucose 4 days after DT administration compared with normoglycemic untreated, control mice. FIG. 9C shows the BLI of a control untreated mouse (left) reveals emission from pancreas. This signal was abolished after DT-treatment (right). FIG. 9D shows that quantitative analysis showed a significant reduction (p=0.01) of BLI after this treatment. FIG. 9E shows that in contrast, the pancreatic uptake of a PET tracer targeting the islet was similar in control and DT-treated mice. FIG. 9F shows ex vivo biodistribution of radiotracer accumulation was similar in organs dissected from DT-treated and untreated MIP-Luc-VU/RIP-DTR mice.

FIG. 10A shows that after luciferin injection, bioluminescence is emitted from the pancreas of a MIP-Luc-VU/RIP-DTR mouse. FIG. 10B shows that a PET/CT image from the same mouse displays radiotracer accumulation in the abdomen, including in the liver, bladder, and intestines. FIG. 10C shows reconstructed bioluminescence tomography of the same mouse displays the bioluminescence source location (displayed in 'hot' color scale) within the CT mouse volume (blue pixels). FIG. 10D shows an axial slice through the tomographic bioluminescence image reveals the reconstructed bioluminescence source location in the expected anatomical location of the pancreas. The dashed red line defines the pancreatic ROI. FIG. 10E shows PET/CT of the same slice displays radiotracer uptake in the kidneys, intestines, spleen, spine, and pancreas. The pancreatic ROI (red) from panel 10D is overlaid on the PET/CT image, demonstrating the pancreatic co-registration of bioluminescence and part of the radiotracer PET signal.

DETAILED DESCRIPTION

Figure 1A:
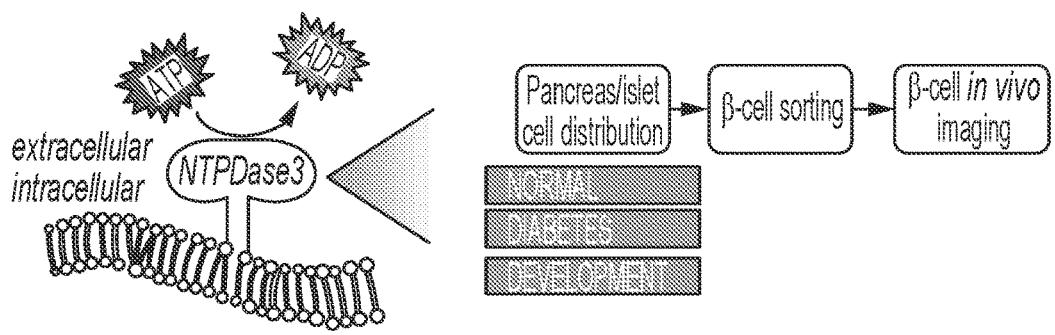
FIG. 1A shows an overview of NTPDase3 analysis and experimental applications.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular anti-CD39L3 antibody is disclosed and discussed and a number of modifications that can be made to a number of molecules including the anti-CD39L3 antibody are discussed, specifically contemplated is each and every combination and permutation of the anti-CD39L3 antibody and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

In response to the challenge of devising new methods and reagents for non-invasively quantified beta cell mass and purifying beta cells, new islet-specific ligands (antibodies to cell surface of islet cells) were developed allowing for the use of new imaging approaches, and unique models to image mouse and human islets in vivo. Accordingly, in one aspect, disclosed herein is a novel biomarker of human pancreatic β-cells, CD39L3 (ectonucleoside triphosphate diphosphohydrolase-3 (NTPDase3)). Disclosed are methods and compositions related to detecting islet β cells with anti-CD39L3 (also known as NTPDase3) antibodies, nucleic acid probes specific for CD39, or labeled small molecules that targets CD39.

It is understood and herein contemplated that detection of anti-CD39L3 labeled islet β cells can be done through either noninvasive or invasive means. The use of non-invasive means to detect islet β cells have the advantage of not requiring surgery (including outpatient surgery), dot not need sample processing or preparation, do not require culturing, and have reduced pain associated with the method. Accordingly, in one aspect, disclosed herein are methods of non-invasively detecting islet β cell mass in a subject comprising a) administering to the subject an anti-CD39L3 antibody, nucleic acid probes specific for CD39, or labeled small molecules that target CD39; and b) assaying for the anti-CD39L3 antibody, nucleic acid probe specific for CD39, or small molecule. Methods of non-invasive detection of antibodies, such as the detection of anti-CD39L3 islet β cells, can be accomplished through the use of noninvasive means of detecting antibodies known in the art, including, but not limited to bioluminescence (BLI), magnetic resonance imaging (MRI), Positron emission tomography (PET), Single photon emission computed tomography (SPECT), computed tomography (CT) scanning, Endoscopic retrograde cholangiopancreatography (ERCP), and/or fluorescence molecular tomography (FMT).

The advantages of non-invasive detection methods notwithstanding, as noted above, the disclosed methods can include detecting β-cells can be accomplished using more invasive methods comprising a) administering to the subject an anti-CD39L3 antibody, nucleic acid probes specific for CD39, or labeled small molecules that target CD39; b) obtaining a pancreatic tissue sample from the subject; and c) assaying for the anti-CD39L3 antibody, nucleic acid probe, or small molecule. Tissue samples can be collected by any means known in the art including but not limited to tissue resection, biopsy (including, but not limited to core needle biopsy, cone biopsy, open biopsy, brush biopsy, endoscopic biopsy, excision biopsy, incision biopsy, stereotactic biopsy), Crosby capsule, lavage, and curettings.

It is understood and herein contemplated that a deficiency in islet β cell mass or function can lead to insufficient levels of insulin, resulting in hyperglycemia and diabetes. Thus, the use of the disclosed anti-CD39L3 antibodies, nucleic acid probes, or small molecules can be used to detect or diagnose diabetes in a subject as a reduction in the number of islet β cells relative to a normal control is indicative of diabetes. Accordingly, disclosed herein are methods of detecting diabetes in a subject comprising contacting the islet β-cells of the subject with an anti-CD39L3 antibody, nucleic acid probes specific for CD39, or labeled small molecules that target CD39, and measuring the mass of the islet β-cells; wherein a decrease in cell mass relative to a control indicates that a subject has diabetes. As with the methods of detection disclosed herein the methods of detecting/diagnosing diabetes in a subject can be accomplished using any invasive or non-invasive means. Thus, disclosed are methods of detecting diabetes in a subject, wherein the islet β-cells are contacted with the CD39L3 antibody or labeled small molecules that target CD39 in vivo and the cell mass is assessed using one or more imaging method selected from bioluminescence (BLI), magnetic resonance imaging (MRI), Positron emission tomography (PET), Single photon emission computed tomography (SPECT), computed tomography (CT) scanning, and/or fluorescence molecular tomography (FMT). Also disclosed herein are methods of detecting diabetes in a subject, wherein the islet β-cells are obtained from a tissue sample obtained from the subject and the islet β-cells are contacted with the anti-CD39L3 antibody ex vivo. In one aspect, the islet β-cell mass is assessed by an immunoassay selected from the group consisting of Radioimmunoassay (RIA), Enzyme-Linked Immunosorbent Assay (ELISA), Enzyme-Linked Immuno spot Assay (ELISPOT), Flow cytometry, fluorescence activated cell sorting (FACS), protein array, multiplexed bead assay, and magnetic capture.

It is understood and herein contemplated that the same antibodies, nucleic acid probes, and small molecules that can be used to detect CD93L3 can also be used to isolate islet 13 cells from tissue. Accordingly, disclosed herein are methods of isolating islet β-cells from a tissue sample from a subject comprising contacting the tissue sample with an anti-CD39L3 antibody, nucleic acid probes specific for CD39, or labeled small molecules that target CD39 and separating the cells expressing CD39L3. Cells can be separated using any means known in the art, including, but not limited to magnetic bead separation and fluorescence activated cell sorting (FACS). Thus in one aspect, disclosed herein are methods of isolating islet β-cells from a tissue sample from a subject comprising contacting the tissue sample with an anti-CD39L3 antibody and separating the cells expressing CD39L3 by FACS or magnetic bead separation to detect and separate cells bound by the CD39L3 antibody; wherein the cells expressing CD39L3 are islet β-cells.

One treatment for diabetes is the administration of islet β cells to a subject with diabetes. It is understood and herein contemplated that islet β cells detected and isolated by the disclosed methods can then be used to treat diabetes. Accordingly, in one aspect, disclosed herein are methods of treating diabetes in a subject comprising a) obtaining a pancreatic tissue sample from a donor; b) contacting the pancreatic tissue sample with a labeled anti-CD39L3 antibody or labeled small molecules that target CD39, wherein the anti-CD39L3 antibody binds to islet β-cells from the pancreatic tissue sample; c) isolating the islet β-cells using magnetic beads or fluorescence activated cell sorting; and d) transferring the isolated islet β-cells from the donor to the subject with diabetes. In one aspect, the islet β cells used in the disclosed methods can be isolated from a subject receiving the β cell therapy (an autologous donor source), from a type match donor source (i.e., syngeneic), from a non-type matched donor source of the same species (i.e, an allogeneic source), or a donor of a different species (xenogeneic source).

Also disclosed herein are methods of testing the efficacy of islet β-cell transplant comprising a) administering the agent to a subject isolated β-islet cells; b) administering an anti-CD39L3 antibody to the subject, wherein the anti-CD39L3 antibody binds to islet βcells; and c) detecting the labeled islet β-cells in the subject by imaging or immunoassay.

It is understood and herein contemplated that one method for detecting the CD39L3 biomarker in the disclosed detection methods and methods of isolating islet β cells, is through the use of antibodies, nucleic acid probes, or small molecules. With their highly selective recognition and binding of molecular targets, antibodies hold great promise as molecular imaging agents. Antibodies typically have greater diversity, specificity, and affinity than peptides. Several antibodies targeting islet cell surface antigens have been evaluated for imaging applications.

1. Antibody

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with CD39L3. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (1), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab, Fv, ScFv, and the like, including hybrid fragments. Thus, fragments of the antibodies that retain the ability to bind their specific antigens are provided. For example, fragments of antibodies which maintain CD39L3 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane.

*Antibodies, A Laboratory Manual.* Cold Spring Harbor Publications, New York, (1988)).

As disclosed herein "diabody" refers to a single chain bi-specific immunoconstruct. Diabodies are bi-specific antibodies comprising two variable regions and no Fc region. Similarly, a tri-specific or bi-specific trivalent antibody (triabody) comprises three variable regions and no Fc region. Unlike typical monospecific divalent antibodies, the variable regions of diabodies and triabodies are specific for different targets. In one aspect, the anti-CD39L3 antibody disclosed herein and used in the disclosed methods is a bi- (diabody), tri- (triabody), or multi-specific antibody.

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature,* 321:522-525 (1986); Riechmann et al., *Nature,* 332:323-327 (1988); and Presta, *Curr. Op. Struct. Biol.,* 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., *J. Immunol.,* 151:2296 (1993) and Chothia et al., *J. Mol. Biol.,* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., *Proc. Natl. Acad. Sci. USA,* 90:2551-255 (1993); Jakobovits et al., *Nature,* 362:255-258 (1993); Bruggemann et al., Year in *Immuno.,* 7:33 (1993)). Human antibodies can also be produced in phage display libraries (Hoogenboom et al., *J. Mol. Biol.,* 227:381 (1991); Marks et al., *J. Mol. Biol.,* 222:581 (1991)). The techniques of Cote et al. and Boerner et al. are also available for the preparation of human monoclonal antibodies (Cole et al., *Monoclonal Antibodies and Cancer Therapy,* Alan R. Liss, p. 77 (1985); Boerner et al., *J. Immunol.,* 147(1):86-95 (1991)).

Disclosed are hybidoma cells that produces the monoclonal antibody. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., *Proc. Natl. Acad. Sci. USA,* 81:6851-6855 (1984)).

Monoclonal antibodies may be prepared using hybridoma methods, such as those described by Kohler and Milstein, *Nature,* 256:495 (1975) or Harlow and Lane. *Antibodies, A Laboratory Manual*. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises CD39L3. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of CD39L3 expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. *Hybridoma*. 1998 December; 17(6):569-76; Kilpatrick K E et al. High-affinity monoclonal antibodies to PED/PEA-15 generated using 5 microg of DNA. *Hybridoma*. 2000 August; 19(4):297-302, which are incorporated herein by referenced in full for the methods of antibody production) and as described in the examples.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of an anti-CD39L3 antibody as fusion proteins. The antigen is produced by inserting a gene fragment in-frame between the signal sequence and the mature protein domain of the anti-CD39L3 antibody nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103) Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.*, 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against CD39L3. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane *Antibodies, A Laboratory Manual* Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816, 567) or by covalently joining to the immunoglobulin coding sequence all or part of the coding sequence for a non-immunoglobulin polypeptide. Optionally, such a non-immunoglobulin polypeptide is substituted for the constant domains of an antibody or substituted for the variable domains of one antigen-combining site of an antibody to create a chimeric bivalent antibody comprising one antigen-combining site having specificity for CD39L3 and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, *Antibodies, A Laboratory Manual*, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) *Synthetic Peptides: A User Guide*. W.H. Freeman and Co., N.Y. (1992); Bodansky M and Trost B., Ed. (1993) *Principles of Peptide Synthesis*. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry,* 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. *Science,* 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) *FEBS Lett.* 307:97-101; Clark-Lewis I et al., *J. Biol. Chem.,* 269:16075 (1994); Clark-Lewis I et al., *Biochemistry,* 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science,* 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with CD39L3. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. *Nucl. Acids Res.* 10:6487-500 (1982).

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. *Antibodies, A Laboratory Manual.* Cold Spring Harbor Publications, New York, (1988), for a description of immunoassay formats and conditions that could be used to determine selective binding. The binding affinity of a monoclonal antibody can, for example, be determined by the Scatchard analysis of Munson et al., *Anal. Biochem.*, 107:220 (1980).

Also provided is an antibody reagent kit comprising containers of the monoclonal antibody or fragment thereof and one or more reagents for detecting binding of the antibody or fragment thereof to CD39L3. The reagents can include, for example, fluorescent tags, enzymatic tags, or other tags. The reagents can also include secondary or tertiary antibodies or reagents for enzymatic reactions, wherein the enzymatic reactions produce a product that can be visualized.

In one aspect, it is contemplated herein that the disclosed antibodies can be used in in vivo, ex vivo, and/or in vitro imaging and detection methods to assess β islet cell mass, detect β islet cells, and purify β islet cells. Accordingly in one aspect, disclosed herein are methods of non-invasively detecting islet βcell mass in a subject, methods of isolating islet βcells from a tissue sample from a subject, methods of treating diabetes, methods of detecting diabetes, methods of testing the efficacy of an agent that is designed to increase islet βcell mass, and/or methods of testing the efficacy of islet βcell transplant comprising contact a β islet cells with the anti-CD39L3 antibodies disclosed herein and measuring or detecting the anti-CD39L3 antibody using imaging methods or immunoassays as disclosed herein; wherein said measurement can occur in vivo with imaging methods or can occur ex vivo or in vitro using immunoassays, immunodetection, or imaging methods.

As used herein, "imaging" can refer to can be many equally sufficient methods for noninvasively imaging tissue in vivo which can be used alone or in combination including but not limited to bioluminescence (BLI), magnetic resonance imaging (MRI), Positron emission tomography (PET), Single photon emission computed tomography (SPECT), computed tomography (CT) scanning (including, but not limited to x-ray computed tomography), fluorescence molecular tomography (FMT), or any other noninvasive imaging technique known. Thus, for example, in one aspect, disclosed herein are noninvasive systems for imaging beta islet cells in a subject comprising one or more of BLI, magnetic resonance imaging, positron emission tomography (PET), single photon emission computed tomography (SPECT), computed tomography (CT) scanning, fluorescence molecular tomography (FMT).

As used herein, "magnetic resonance imaging" refers to the use of use magnetic fields and radio waves to form images of the body. Typically, when used in cardiac situations, cardiovascular magnetic resonance imaging (CMR) involves ECG gating which combats the artifacts created by the beating of the heart.

"computed tomography" means the use of x-ray images taken from the patient at different angles to produce tomographic (cross-sectional) images.

2. Immunoassays and Fluorochromes

The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, fluorescence activated cell sorting (FACS), protein arrays, multiplexed bead arrays, magnetic capture, in vivo imaging, fluorescence resonance energy transfer (FRET), and fluorescence recovery/localization after photobleaching (FRAP/FLAP). In one aspect, disclosed herein are methods of non-invasively detecting islet β-cell mass in a subject, methods of isolating islet β-cells from a tissue sample from a subject, methods of treating diabetes, methods of detecting diabetes, methods of testing the efficacy of an agent that is designed to increase islet β-cell mass, and/or methods of testing the efficacy of islet β-cell transplant; comprising amongst other things detecting the presence of or measuring the amount of anti-CD39L3 antibody or detecting or measuring cells comprising CD39L3 that have said antibodies bound to them using one or more immunoassays including but not limited to Radioimmunoassay (RIA), Enzyme-Linked Immunosorbent Assay (ELISA), Enzyme-Linked Immuno spot Assay (ELISPOT), Flow cytometry, fluorescence activated cell sorting (FACS), protein array, multiplexed bead assay, and magnetic capture.

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

As used herein, a label can include a fluorescent dye, a member of a binding pair, such as biotin/streptavidin, a morpholino (MORF)/complementary MORF (cMORF), a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; CyS™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DlC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green;

Magdala Red (Phloxin B); Mag-Fura Red; Mag-Fura-2; Mag-Fura-5; Mag-lndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (Pl); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair or MORF/cMORF. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250:4007-4021 (1975), herein incorporated by reference in its entirety for its teaching regarding two-dimensional electrophoresis methods. Other examples include but are not limited to, those found in Anderson, L and Anderson, NG, High resolution two-dimensional electrophoresis of human plasma proteins, Proc. Natl. Acad. Sci. 74:5421-5425

(1977), Ornstein, L., Disc electrophoresis, L. Ann. N.Y. Acad. Sci. 121:321349 (1964), each of which is herein incorporated by reference in its entirety for teachings regarding electrophoresis methods. Laemmli, U.K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromogenic detection. Standard methods for Western blot analysis can be found in, for example, D. M. Bollag et al., *Protein Methods* (2d edition 1996) and E. Harlow & D. Lane, *Antibodies, a Laboratory Manual* (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), morpholino (MORF) conjugated primary antibodies (e.g., MORF with labeled complementary morpholino (cMORF)), or probes to biotinylated primary antibodies (e.g., conjugated avidin/streptavidin). In one aspect, the anti-CD39L3 antibodies used in the methods disclosed herein can be primary antibodies comprising a directly detectable label or primary antibody conjugated to an unlabeled detectable marker. Where the method utilizes an antibody with an unlabeled detectable marker, the method can further comprise a secondary labeled antibody which is specific for conjugated marker on the primary antibody.

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner Exemplary techniques are described in Ornstein L., Disc electrophoresis—I: Background and theory, Ann. NY Acad. Sci. 121:321-349 (1964), and Matsudiara, PT and DR Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at <http://www.promega.com/faq/gelshfaq.html> (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Enzyme-Linked Immuno spot Assay (ELISPOT), Flow cytometry, fluorescence activated cell sorting (FACS), protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}I$ or $^{131}I$ are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase.

Variations of ELISA techniques are know to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

Enzyme-Linked Immunospot Assay (ELISPOT) is an immunoassay that can detect an antibody specific for a protein or antigen. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. In this assay a nitrocellulose microtiter plate is coated with antigen. The test sample is exposed to the antigen and then reacted similarly to an ELISA assay. Detection differs from a traditional ELISA in that detection is determined by the enumeration of spots on the nitrocellulose plate. The presence of a spot indicates that the sample reacted to the antigen. The spots can be counted and the number of cells in the sample specific for the antigen determined.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialised chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include colour coding for microbeads (Luminex, Austin, Tex.; Bio-Rad Laboratories) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilised on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in E. coli, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on Staph. aureus protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany) These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colours. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumour extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into E. coli, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, Conn.).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

Like many other antibody-based attempts in molecular imaging, efforts to image islets in vivo with antibodies suffer two limitations: slow clearance of antibodies from the blood, with half-lives on the order of days to weeks, and high background uptake in non-target tissue, lowering the target to non-target ratio. The pre-targeting/clearance approach developed herein overcomes limitations that have plagued antibody-based imaging applications, open new areas of investigation, and serve as a platform imaging technology to assess new imaging ligands in the future.

Accordingly, in one aspect, disclosed herein are methods of non-invasively detecting islet β-cell mass in a subject, methods of non-invasively detecting diabetes, methods of methods of non-invasively testing the efficacy of an agent that is designed to increase islet β-cell mass, and/or methods of non-invasively testing the efficacy of islet β-cell transplant comprising administering to a subject an anti-CD39L3 antibody, wherein the antibody is conjugated to a detectable substrate (such as, for example, biotin and/or MORF); administering a clearing agent (such as, for example, a secondary antibody comprising a detectable label (such as, for example an avidin or cMORF) and has specificity for the detectable substrate on the primary anti-CD39L3 antibody).

3. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br.*

*J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

4. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

5. Compositions Identified by Screening with Disclosed Compositions/Combinatorial Chemistry a) Combinatorial Chemistry The disclosed anti-CD39L3 antibodies can be used as targets for any combinatorial technique to identify molecules or macromolecular molecules that interact with the disclosed anti-CD39L3 antibodies in a desired way. Also disclosed are the compositions that are identified through combinatorial techniques or screening techniques in which the anti-CD39L3 antibodies are used as the target in a combinatorial or screening protocol.

In one aspect, disclosed herein are methods of testing the efficacy of an agent that is designed to increase islet β-cell mass comprising administering the agent to a subject; administering an anti-CD39L3 antibody to the subject; and measuring the mass of the islet β-cells in the subject by imaging or immunoassay, wherein an increase in the islet β-cell mass relative to a control indicates that the agent increases β-cell mass.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed anti-CD39L3 antibodies, are also disclosed. Thus, the products produced using the combinatorial or screening approaches that involve the disclosed anti-CD39L3 antibodies, are also considered herein disclosed.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. *Proc. Natl. Acad. Sci. USA*, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. *Proc. Natl. Acad. Sci. USA*, 94(23)12997-302 (1997)).

Another preferred method for combinatorial methods designed to isolate peptides is described in Cohen et al. (Cohen B. A., et al., *Proc. Natl. Acad. Sci. USA* 95(24): 14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art. 162. Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919, 955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2, 3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721, 099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in interative processes.

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed anti-CD39L3 antibodies.

It is understood that when using the disclosed compositions in modeling techniques, molecules, such as macromolecular molecules, will be identified that have particular desired properties such as inhibition or stimulation or the target molecule's function. The molecules identified and isolated when using the disclosed anti-CD39L3 antibodies, are also disclosed. Thus, the products produced using the molecular modeling approaches that involve the disclosed anti-CD39L3 antibodies, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

6. Kits

Disclosed herein are kits that are drawn to reagents that can be used in practicing the methods disclosed herein (such as, for example, methods of non-invasively detecting islet β-cell mass in a subject, methods of isolating islet β-cells from a tissue sample from a subject, methods of treating diabetes, methods of detecting diabetes, methods of testing the efficacy of an agent that is designed to increase islet β-cell mass, and/or methods of testing the efficacy of islet β-cell transplant). The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for detecting diabetes in a subject, comprising an anti-CD39L3 antibody. Also disclosed are kits for measuring beta islet cell mass comprising an anti-CD39L3 antibody as disclosed herein.

B. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The overall goal of the research was to develop, optimize, and evaluate novel nuclear imaging methods for quantifying pancreatic islet cell mass in vivo. The small size of islets, their low abundance, and their scattered distribution create considerable challenges for non-invasive methods to quantify islet cell mass. Indeed, imaging pancreatic islets in vivo continues to be a vexing scientific challenge. Despite the efforts of a number of investigators, no current approach allows for the non-invasive assessment of islet cell mass in humans. The ability to measure pancreatic islet cell mass would lead to a better understanding of the pathogenesis of diabetes, provide an early diagnostic indicator of type 1 and type 2 diabetes, and accelerate the development and evaluation of new therapies.

Approaches to noninvasively assay beta cell mass are greatly needed because being able to assess beta cell mass would lead to a better understanding of the pathogenesis of diabetes, provide an early diagnostic marker for type 1 and type 2 diabetes, and accelerate the development and evaluation of new therapies. For example, reduced beta cell mass is a cardinal feature of Type 1 diabetes and is now recognized as a critical feature in type 2 diabetes as well, but beta cell mass cannot be non-invasively quantified in humans. While the amount of insulin/C-peptide secreted following a glucose or meal challenge gives insight into insulin secretory capacity, these only indirectly reflect beta cell mass and cannot determine whether beta cell mass is improved or declining Additionally, glucose homeostasis is unaffected until beta cell mass is reduced to less than half its original value, presumably due to a large functional reserve capacity. Pancreatic islet mass can be accurately quantified by morphometric analysis of histological sections of the pancreas, but this requires removal of the pancreas. Thus, the time course of how both forms of diabetes develop is incompletely understood and this limits the ability to effectively test interventions to prevent beta cell loss or to increase beta cell mass in those with diabetes. Likewise, efforts to improve islet transplantation would greatly benefit from the ability to assess the number of islets surviving after transplantation.

Through considerable efforts by many investigators, a number of radiotracers targeting various islet receptors or processes have been evaluated for islet imaging but have thus far not proven useful for quantifying islet mass in humans. This lack of success most likely reflects the failure to achieve the requisite endocrine cell sensitivity and endocrine to exocrine binding contrast needed to distinguish islet cells. An ideal method or technology to image and quantify islet cell mass would have the following features:
   a. Non-invasive and allow for serial quantitative measurements in the same animal or person
   b. Specifically identify islet cells with minimal background signal from surrounding exocrine pancreas
   c. Non-toxic to islet cells
   d. Reflect islet cell mass in pathophysiologically relevant conditions
   e. Not require ex-vivo labeling methods so that native pancreatic islets can be imaged
   f. Adaptable to both human and murine islets since studies with genetically-modified mice greatly accelerate new knowledge applicable to human islet physiology

1. Example 1: Newly-Developed, Islet Cell Surface-Directed Antibodies

In addition to analyzing human β-cells ex vivo, there is great need to identify and visualize β-cells non-invasively in vivo. Indeed, although reduced β-cell mass is an established feature of diabetes progression, current knowledge has originated from post-mortem analysis because there are no effective methods to quantify β-cell mass non-invasively in humans. This limitation has greatly hindered our understanding of disease risk and progression and prevents the evaluation of interventions designed to preserve or increase β-cell mass. Many traditional imaging modalities lack necessary sensitivity for the small size and sparse distribution of islets, and better reagents are necessary to distinguish β-cells from other endocrine cells and neighboring exocrine tissue. Antibodies typically have greater specificity and affinity than other molecules such as peptides and small molecules, and multiple antibodies targeting islet cell surface antigens have unsuccessfully been tried for islet imaging applications in vivo.

In efforts to identify cell surface markers of human β-cells, we examined expression of nucleoside triphosphate diphosphoyhydrolase-3 (NTPDase3), an enzyme localized to the endocrine islet in the human pancreas, using a monoclonal antibody. NTPDase3 (encoded by gene ENTPD3) is a member of the E-NTPDase family, which is comprised of eight members. The function of NTPDase3, and of other related ectonucleotidases, is to modulate local extracellular nucleotide levels, thereby affecting availability of ligands that mediate nucleotide signaling. The ectonucleotidase NTPDase3 has been mainly studied in the rodent brain, where it is proposed to help regulate synaptic function. In human, NTPDase3 is expressed in brain, GI tract, and urinary bladder tissues as reported by the NIH Genotype-Tissue Expression Saunders et al. (3) (GTEx) program. Of particular interest to the current study, NTPDase3 is expressed in pancreatic islets of both human and rodents, and recent work has suggested its activity in regulating insulin secretion.

a) Results and Discussion

Figure 1B:
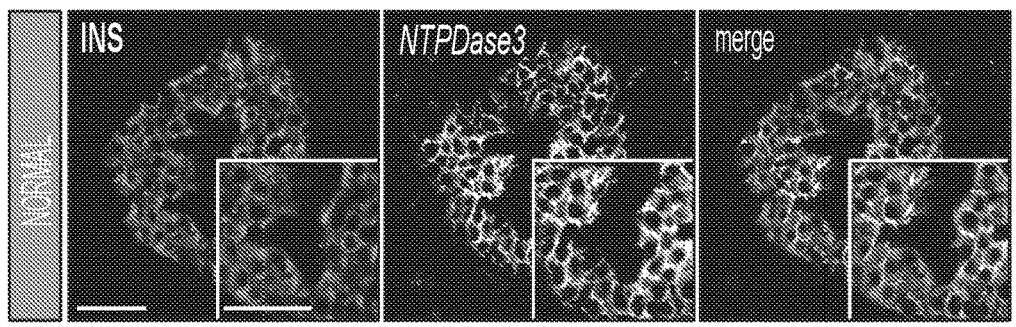
FIG. 1B shows a representative image of an islet in an adult pancreas (18yM) showing NTPDase3 expression in INS$^+$ cells. See also FIG. 2.
Figure 1C:
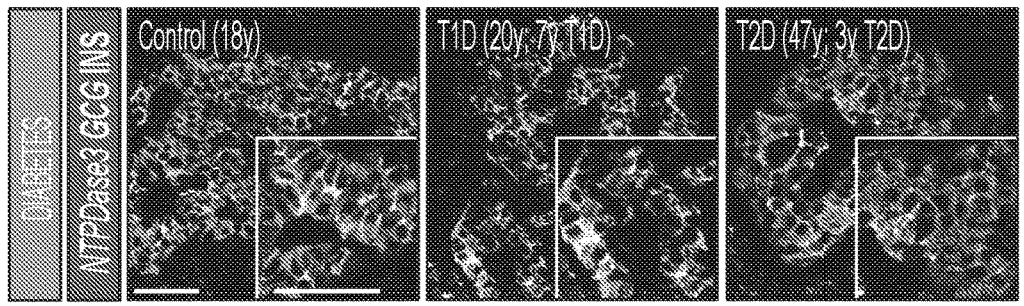
FIG. 1C shows that NTPDase3 expression is retained in β-cells from individuals with type 1 (T1D) and type 2 (T2D) diabetes.
Figure 2E:
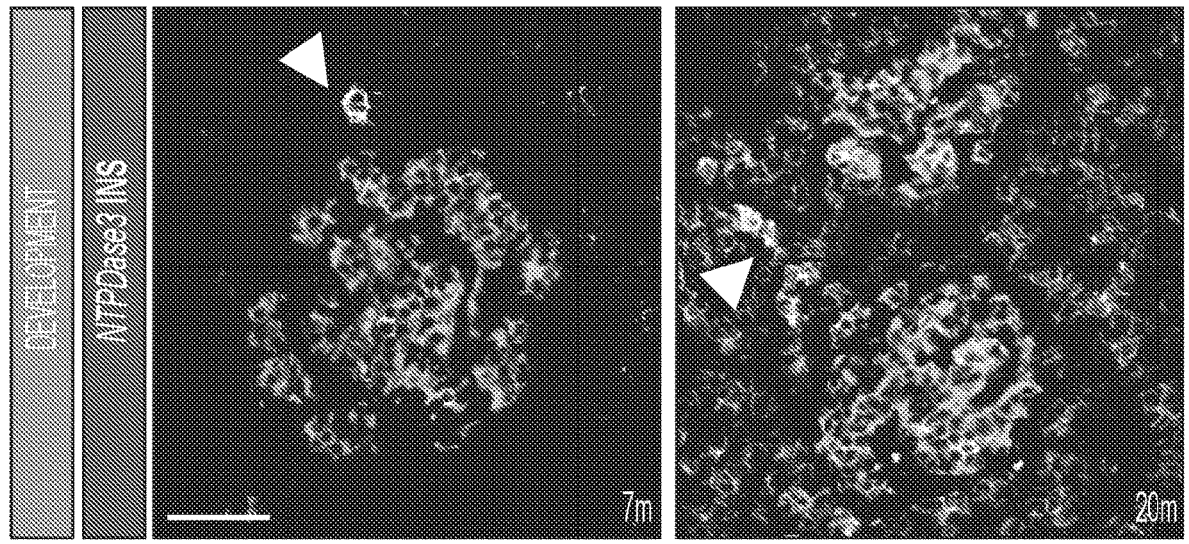
Figure 3:
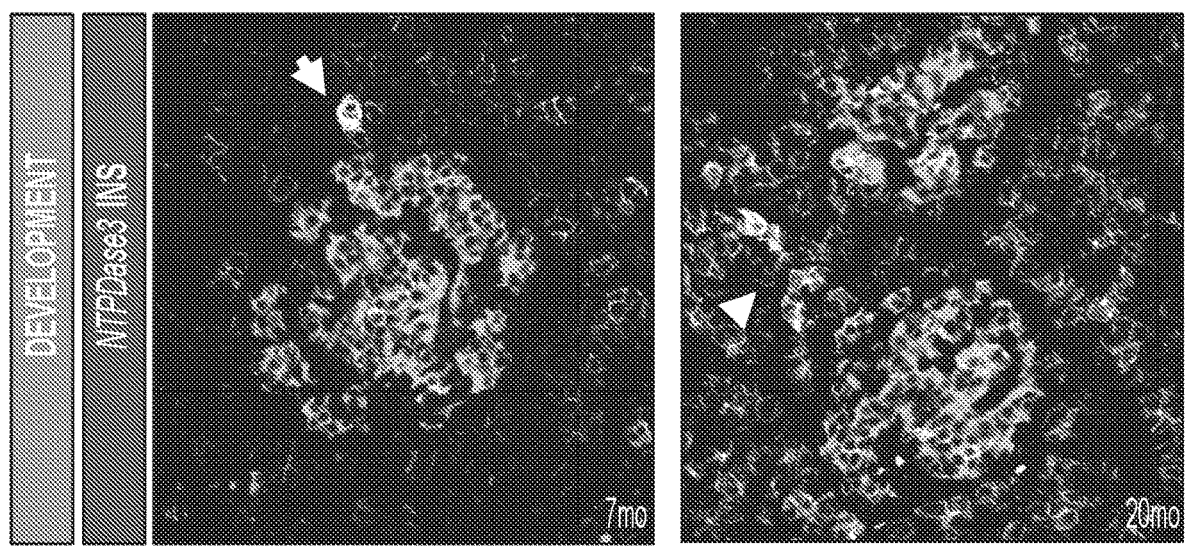
FIG. 3 shows the expression of NTPDase3 in islets from additional juvenile individuals.

To characterize expression of NTPDase3 (FIG. 1a), immunohistochemistry was performed on pancreatic tissue sections from human donors (n=18, age range of 0-49 years) and found NTPDase3 expression on the membrane of most adult β-cells, but importantly, not in adult α-cells (FIGS. 1b and 2a). This is in contrast to a prior report of NTPDase3 expression by human α-cells. No colocalization of NTPDase3 with pancreatic polypeptide (PP) hormone (FIG. 2c) or amylase (exocrine enzyme; FIG. 2d) was observed, though a small number of somatostatin-expressing δ cells did express NTPDase3 (FIG. 2b). These results differ from a prior report in mice where NTPDase3 was found to colocalize with markers of all islet cells (α-, β-, δ-, and PP cells) by immunohistochemistry. Significantly, β-cell NTPDase3 expression was preserved in human T1D and T2D disease states (FIGS. 1c and 3a). The level of NTPDase3 expression, which appeared more polarized than evenly distributed throughout the cell membrane, was similar across all β-cells, indicating that this marker of β-cells does not correlate with recently reported β-cell subtypes.

Figure 1D:
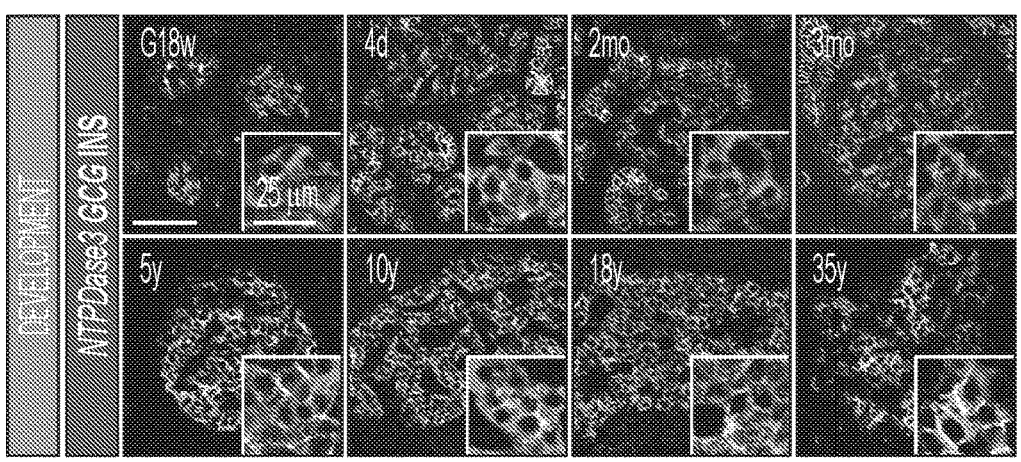
FIG. 1D shows that NTPDase3 has a different pattern of expression in the human pancreas at different stages of development; in top row, NTPDase3 is initially restricted to pancreatic epithelium and acinar cells, but by 1 year of age, acinar cell expression has ceased and only β-cells specifically express NTPDase3 (bottom row). INS—insulin green; NTDPase, red; GCG—glucagon blue. Scale bars in 1B, 1C, and 1D are 50 μm. Human pancreatic donor information is available in Table 1.

Interestingly, although NTPDase3 labeled adult human β-cells with high specificity, its expression during early pancreas development, especially the first few years of life, is quite dynamic. At 18 weeks of gestation (G18W), human acinar cells, but not β-cells, expressed NTPDase3 (FIG. 1d, top panel), but NTPDase3 was expressed in developing pancreatic epithelium. During neonatal period (birth-2 months), human acinar cells, but only a few b-cells, expressed NTPDase3 (4 d, 2 mos; FIG. 1d). In infancy, between 3 months and 2 years of age, NTPDase3 expression became less in acinar cells and appeared in an increasing proportion of β-cells; this transition was heterogeneous among individuals and even in islets from the same pancreas. During this age range, both acinar cells and β-cells expressed NTPDase3 (FIGS. 2e and 3b). By 5 years of age, acinar expression was completely absent and NTPDase3 was only expressed in β-cells (5 y, 10 y, 18 y, and 35 y; FIG. 1d, bottom panel).

Based on the expression pattern of NTPDase3 and current knowledge of postnatal β-cell development, it was postulated that NTPDase3 is important for β-cells to attain their functional maturity. As modulators of extracellular ATP, NTPDases directly impact purinergic signaling pathways controlling processes like glucose-stimulated insulin secretion. Furthermore, the cellular expression of specific purinergic receptor subtypes appears to change during rodent pancreatic development and also under diabetic conditions, indicating that NTPDase expression is functionally relevant in pancreatic islets and can affect β-cell maturation.

Figure 4A:
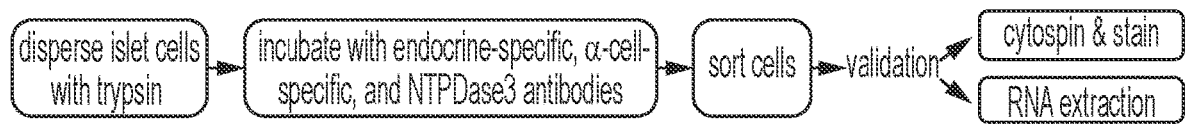
FIGS. 4A, 4B, 4C, 4D, and 4E show that NTPDase3 antibody effectively and efficiently isolates β-cells from live dispersed human islet cells.
Figure 4B:
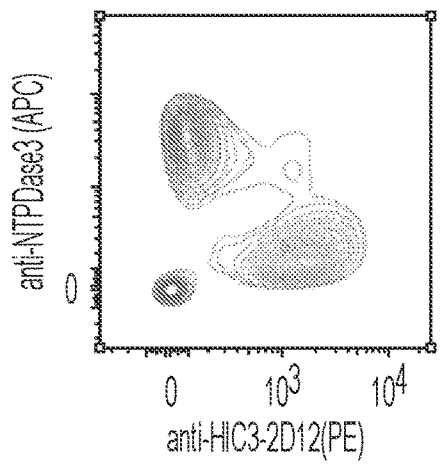
Figure 4C:
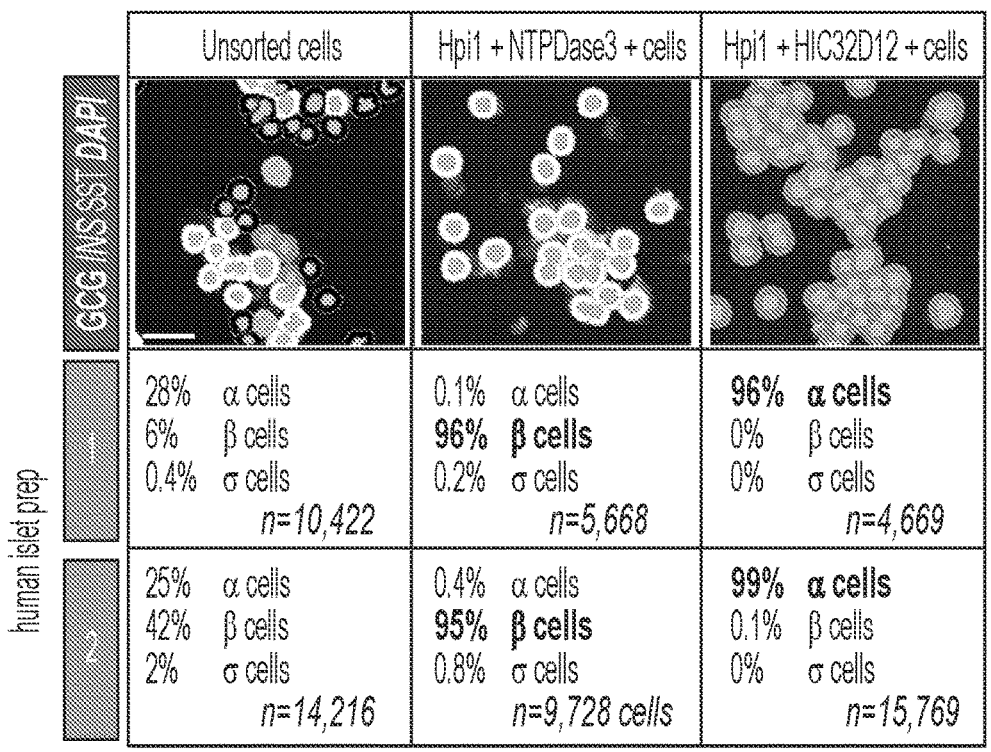
Figure 4D:
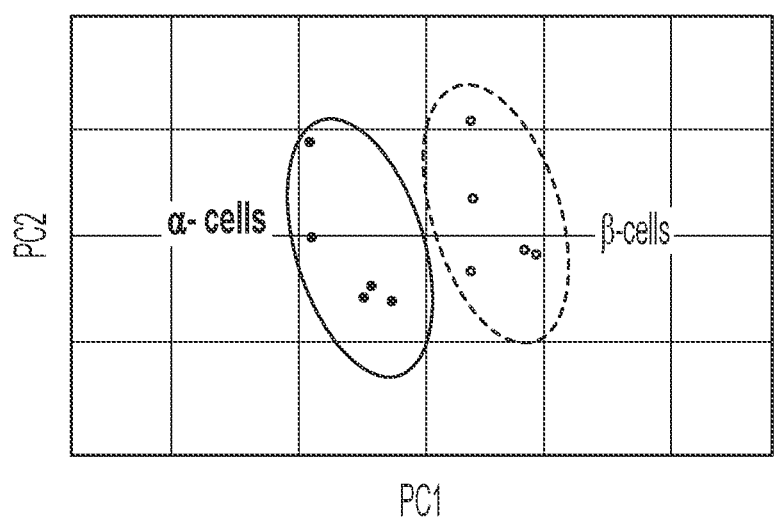
Figure 4E:
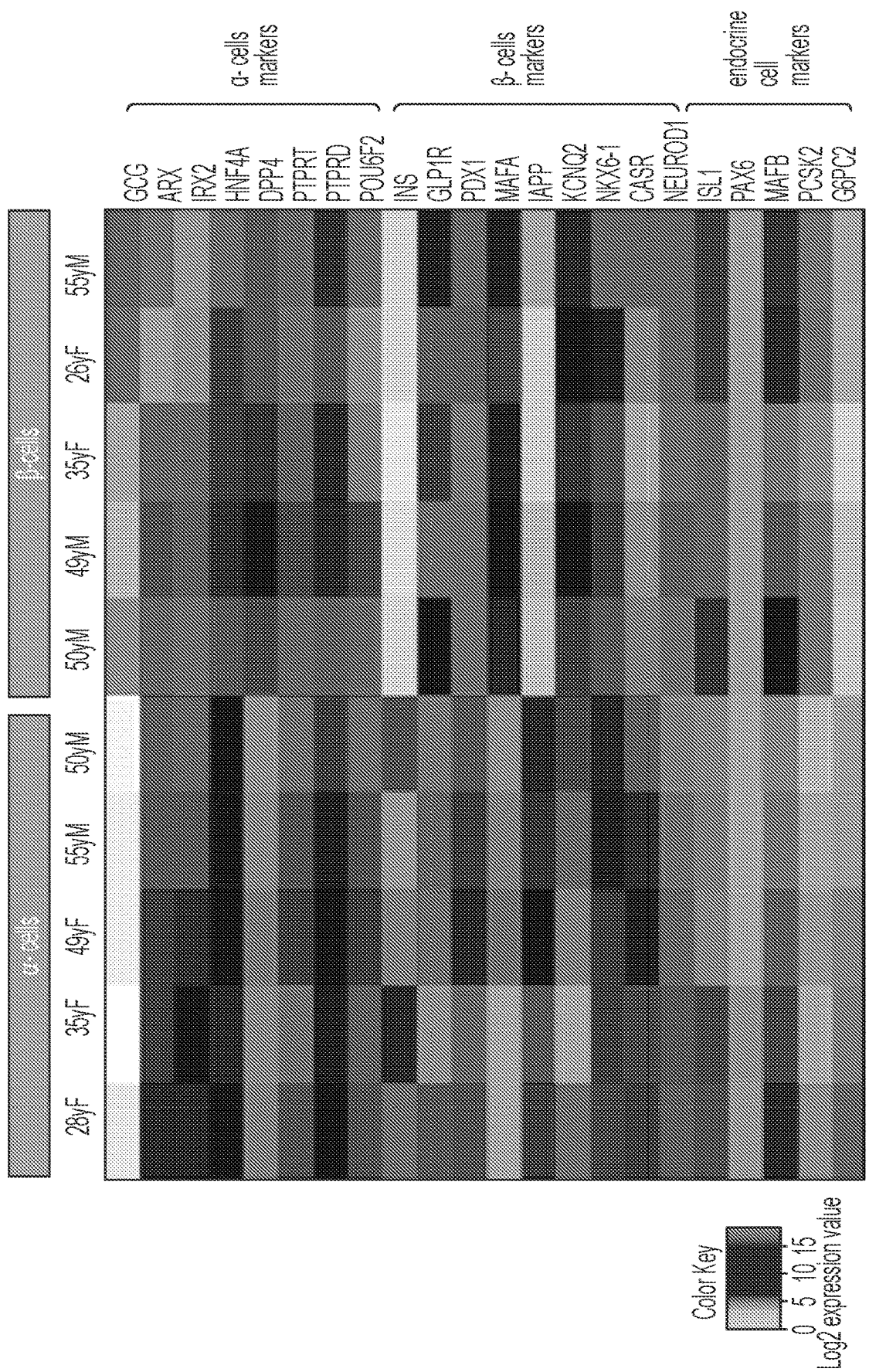

To investigate the utility of NTPDase3 as a biomarker for mature β-cells, a cell sorting strategy was developed to label live human islet cells (FIG. 4a). Use of the NTPDase3 antibody in combination with previously characterized cell surface markers enabled effective separation of α- and β-cell subpopulations (FIGS. 4b and 5). The purity of the subpopulations was validated using two complementary approaches, immunocytochemistry (FIG. 4c) and RNA sequencing (RNA-seq). Based on hormone expression (insulin, glucagon, somatostatin), β- and α-cell populations were enriched to 96% and 98% purity, respectively, from a dispersed islet preparation composed of many disparate cell types (FIG. 4c). This separation was corroborated by principal component analysis of α- and β-cell subpopulations (FIG. 4d). Transcripts of α-cell-specific genes (e.g. Arx, Hnf4a) were highly expressed in α-cell samples and minimally expressed in β-cell samples; the inverse was true of β-cell-specific genes (e.g. Glp1r, Pdx1), which were detected at high levels only in β-cell samples (FIG. 4e) and minimally expressed in islet α-cells, other endocrine cells and acinar cells. Genes common to both α- and β-cells (e.g. Isl1, Pax6) showed similar abundance in both cell types. NTPDase3 transcript (ENTPD3) was approximately 10-fold higher in β-cells than α-cells.

Prior studies have relied on isolating live β-cells through exclusion of other cell types, which results in higher contamination (e.g. up to 13% in β-cells as reported by Bramswig et al.) and means that existing data sets are contaminated with gene expression data from non-β-cells. The results using NTPDase3 as a positive selector of β-cells provide a more accurate transcriptional profile than other cell sorting approaches and without compromising membrane integrity, as is required for sorting using intracellular insulin. Furthermore, recent single cell RNA-seq (scRNA-seq) studies incompletely define human β-cells, as the technology still lacks the sensitivity to reliably detect low-abundance transcripts. For example, recent scRNA-seq studies performed on human islet cells detected an average of only 3,000-7,000 genes per cell. In contrast, the bulk analysis captured the expression of over 20,000 genes. A NTPDase3-based sorting strategy can considerably improve the accuracy of transcriptional profiling from "bulk" or sorted populations of cells.

Figure 5A:
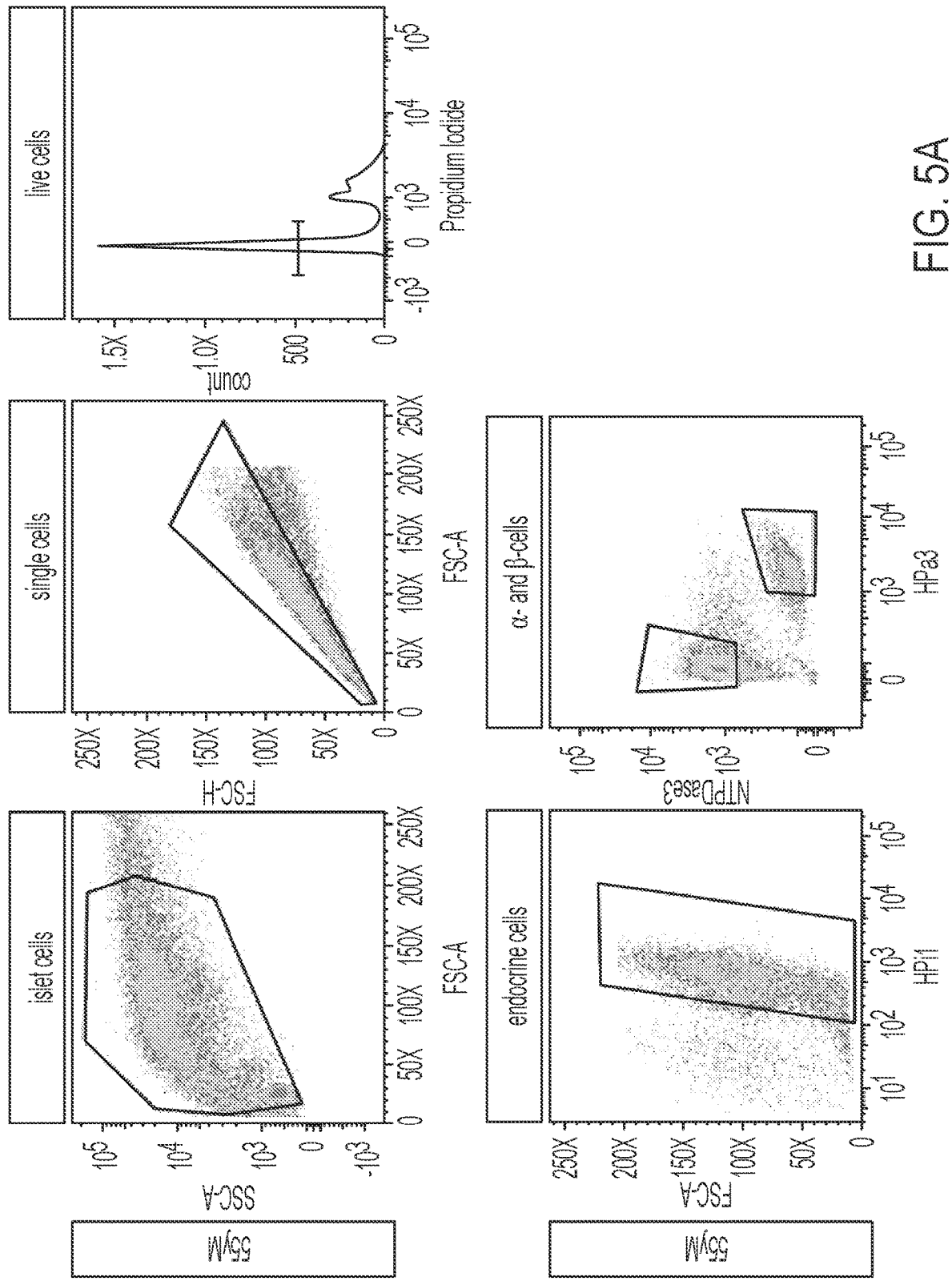
FIGS. 5A, 5B, 5C, 5D, and 5E show NTPDase3-based cell sorting method can be applied to islets from various disease states. The labeling strategy depicted in FIG. 23a is applicable to dispersed human islet cells from (5A) nondiabetic adult donors, (5B) juvenile donors, (5C) donors with T1D, (5D) donors with T2D, and (5E) donors with MODY. Donor information is available in Table 1. Gating strategy is shown in each row, with column labels indicating the gated population. Cell debris were excluded by forward scatter (FSC) and side scatter (SSC), single cells were identified by the FSC-A v. FSC-H plot, and non-viable cells were excluded using propidium iodide (PI). Endocrine cell subpopulations were then isolated based on positivity for HPi1 and additional positivity for HPa3 (α-cells) or NTPDase3 (β-cells).
Figure 5B:
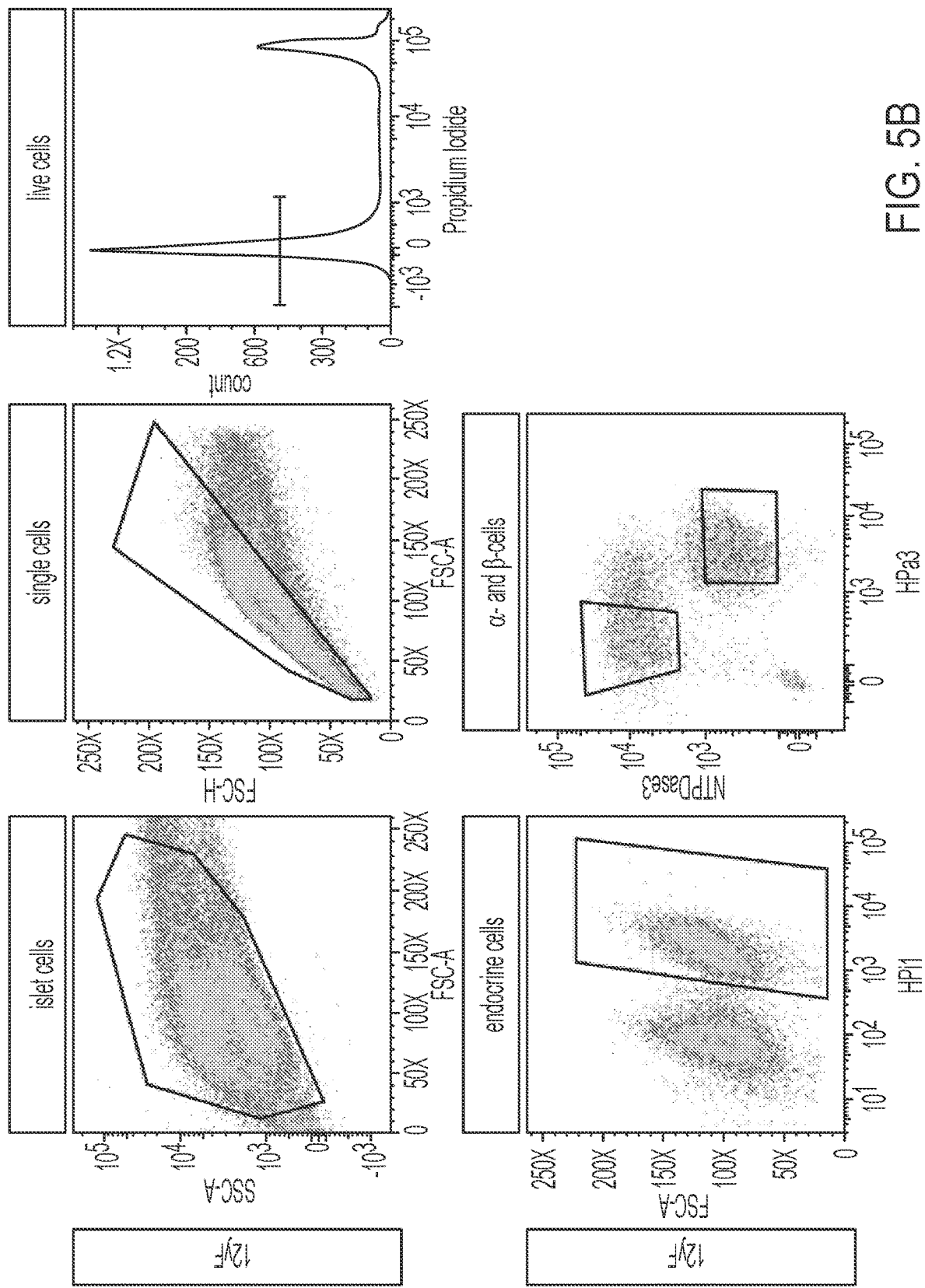
Figure 5C:
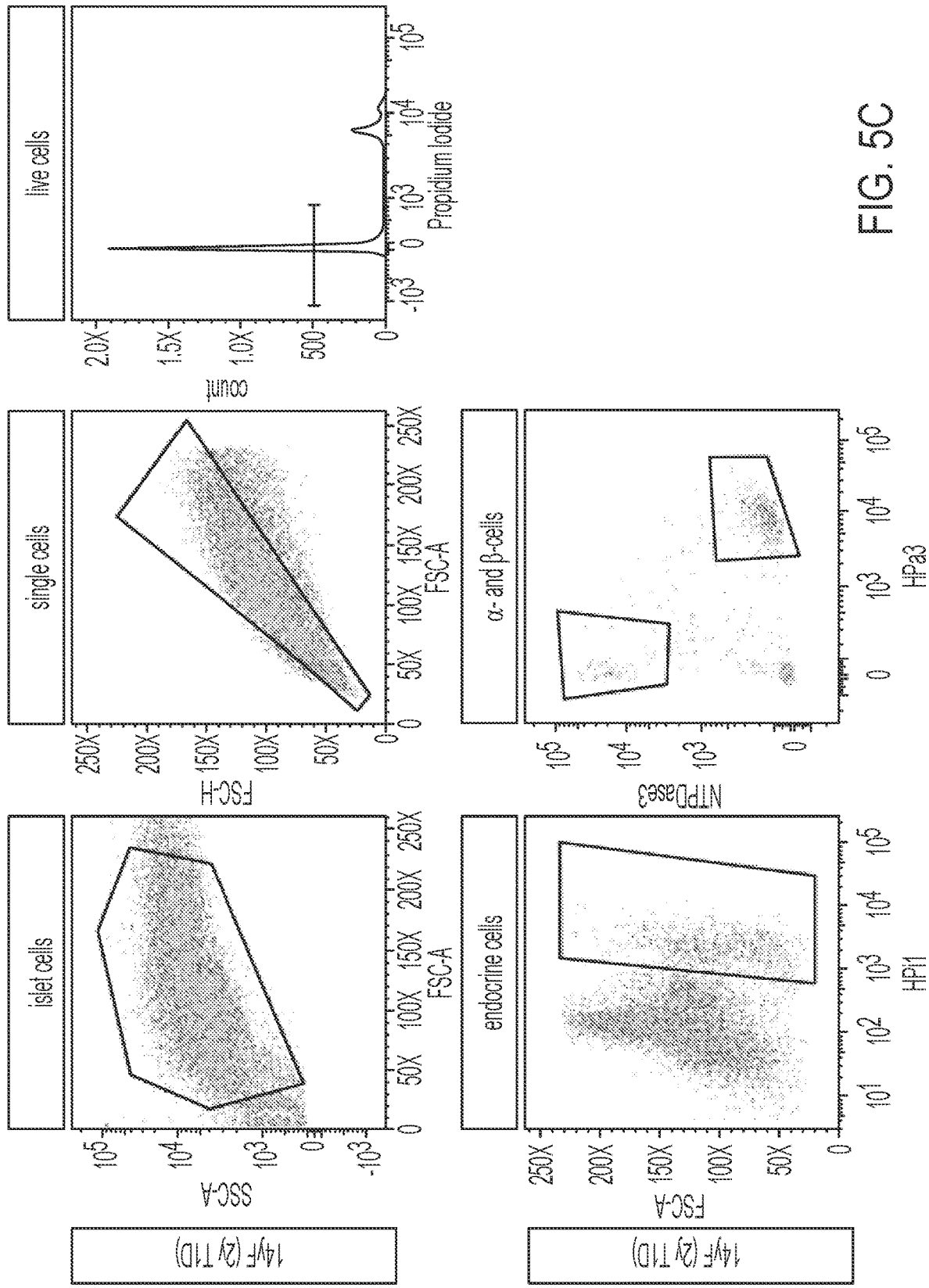
Figure 5D:
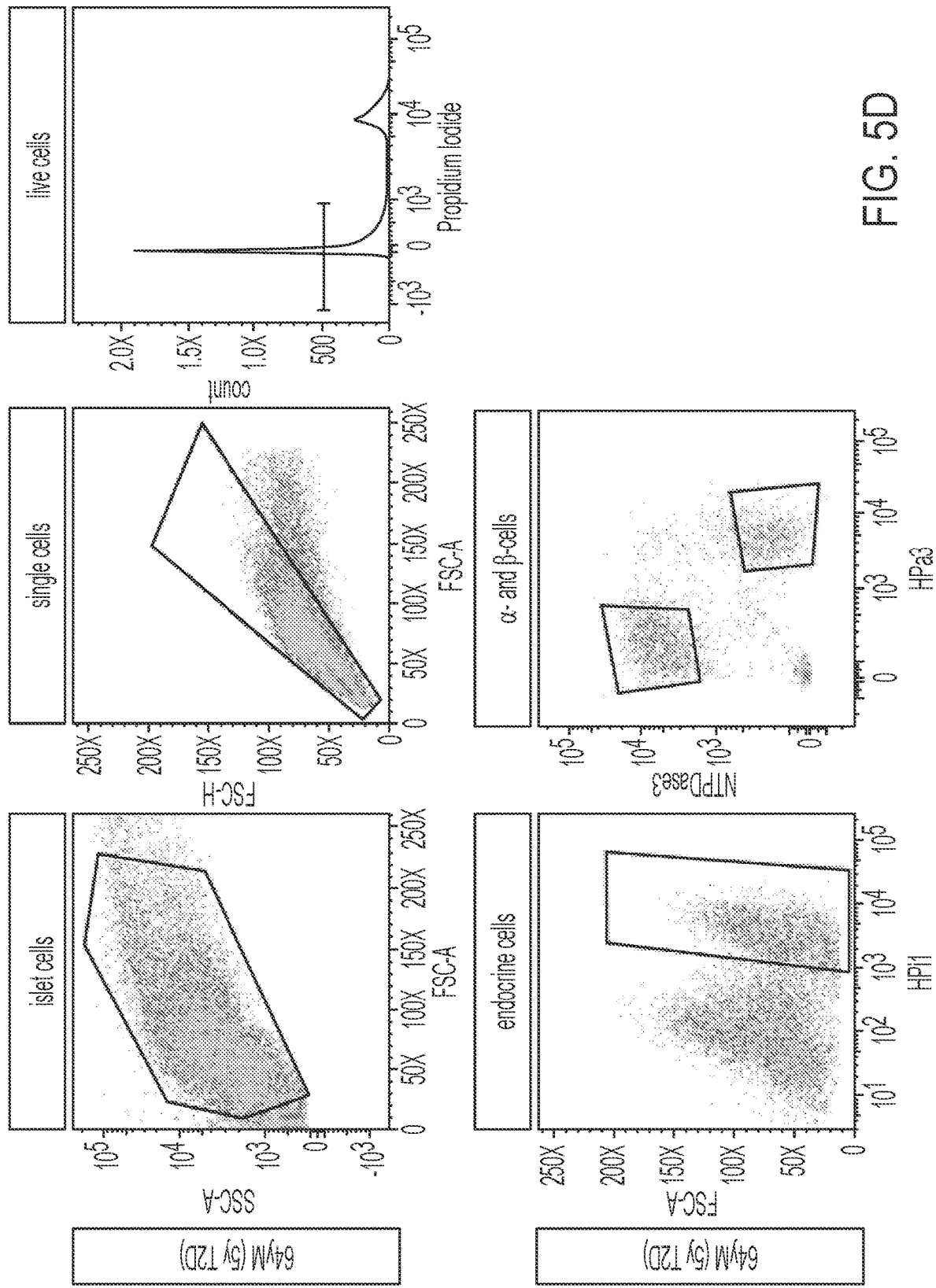
Figure 5E:
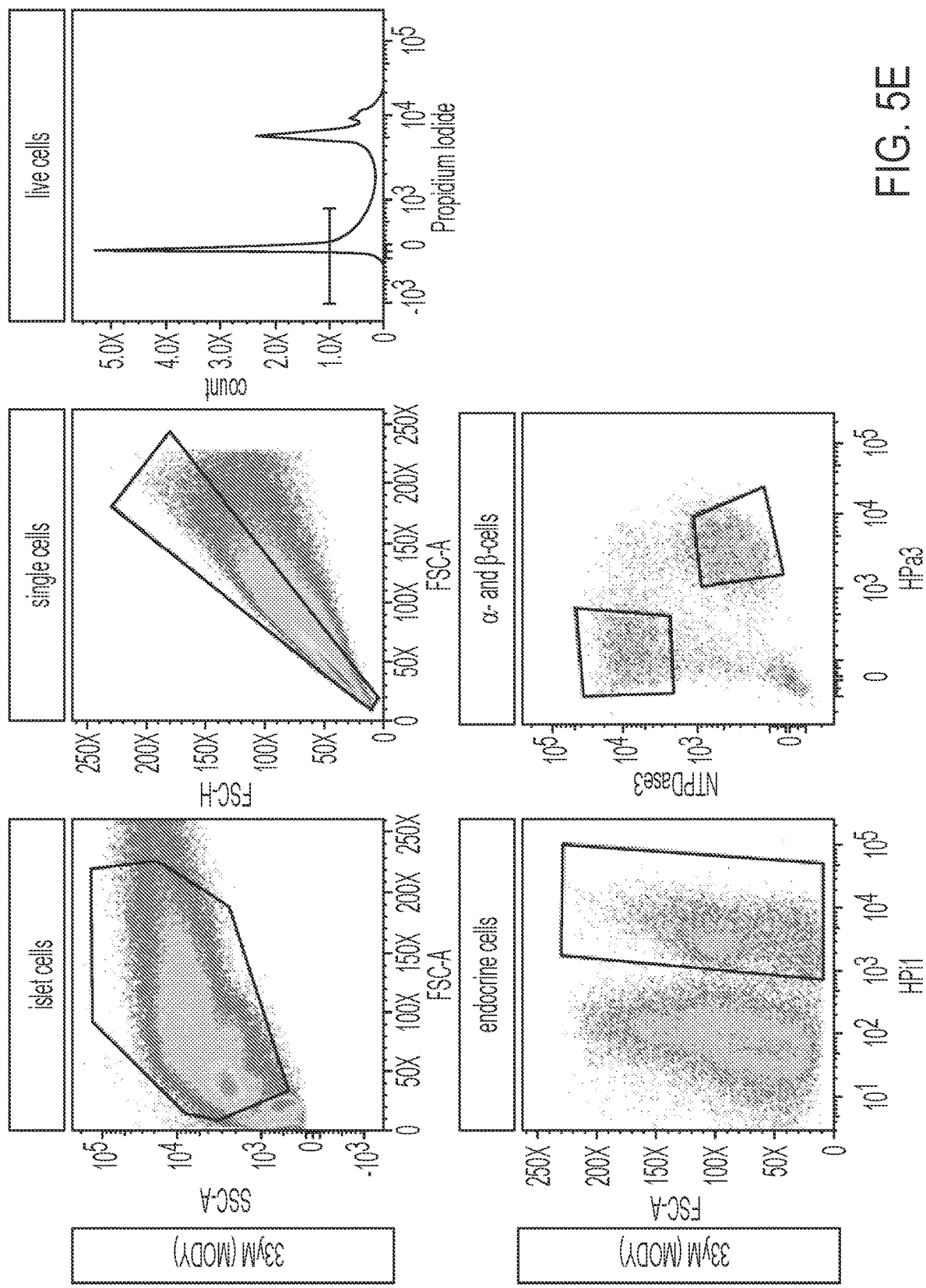

Targeting NTPDase3 in human β-cells opens several new avenues for investigation and discovery. Isolation of β-cell populations with greater purity can enable physiological experiments requiring live β-cells, including electrophysiology, high-resolution imaging, and formation of pseudoislets, and also allows for chromatin immunoprecipitation (CHIP)-seq and assay for transposase-accessible chromatin sequencing (ATAC-seq) experiments on human β-cells. As shown in FIGS. 5a, 5b, 5c, 5d, and 5e; NTPDase3-based cell sorting methods can be applied to islets from various disease states including nondiabetic adult donors (FIG. 5a), juvenile donors (FIG. 5b), donors with T1D (FIG. 5c), donors with T2D (FIG. 5d), and donors with maturity onset diabetes of the young (MODY) (FIG. 5e).

Figure 6D:
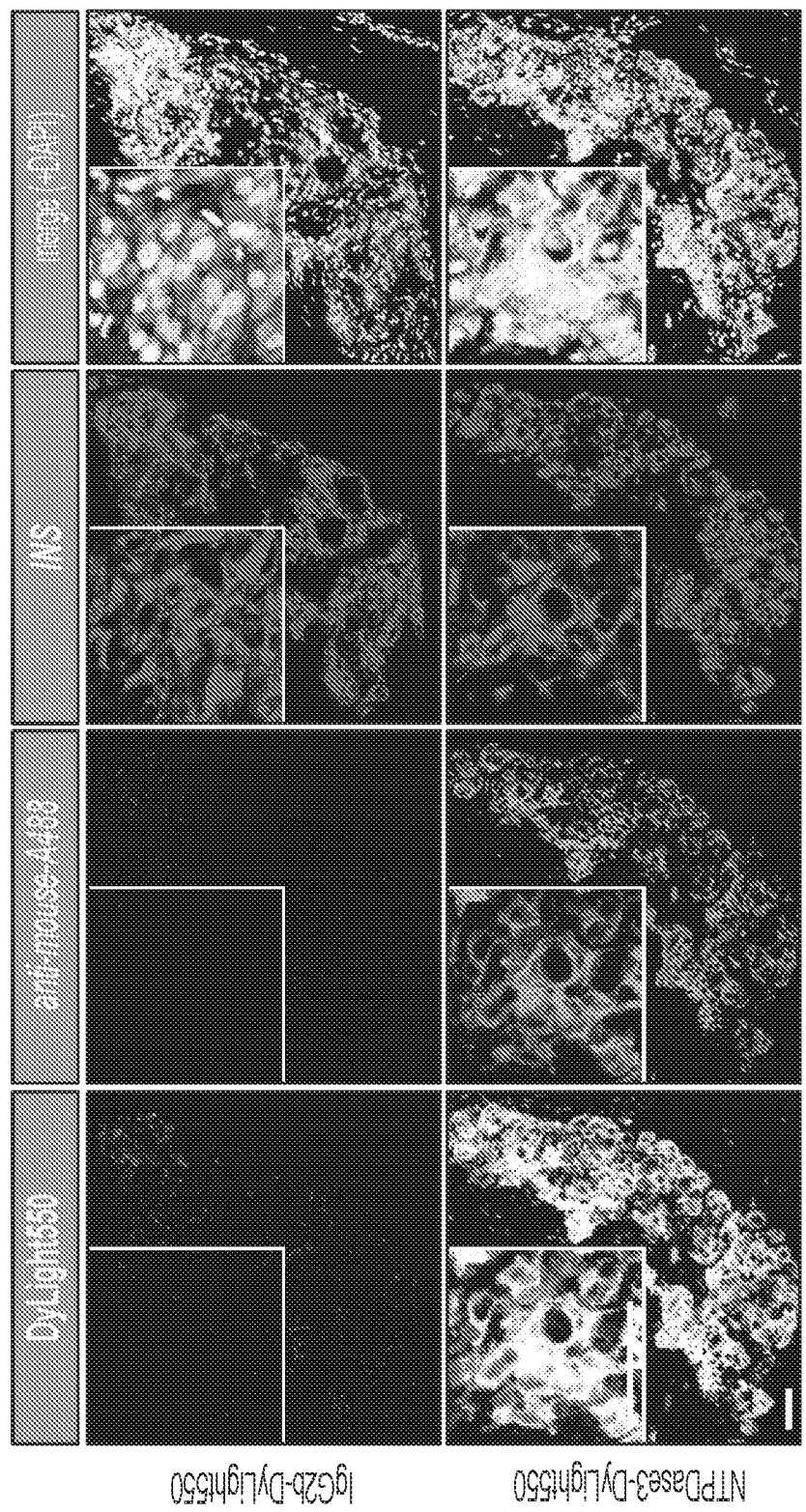
Figure 7C:
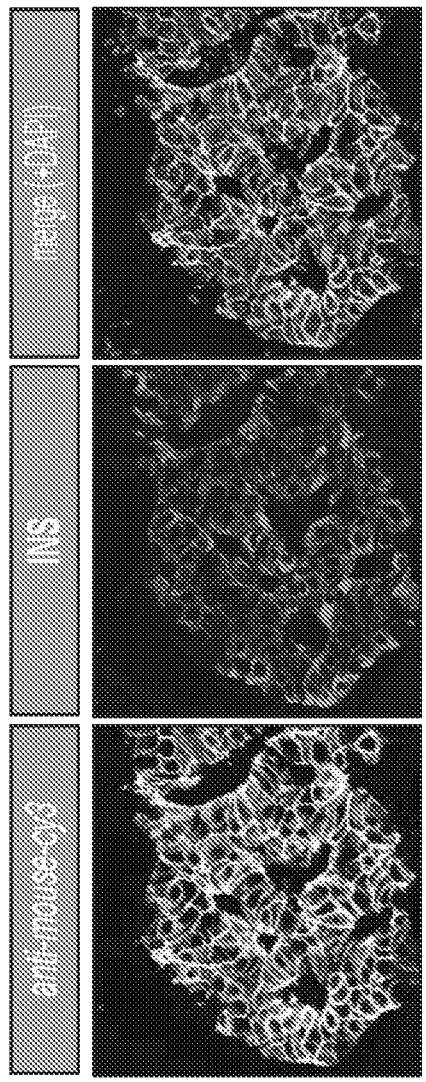
FIGS. 7A, 7B, and 7C show the detection of intravenously-injected NTPDase3 antibody in human islet graft beneath the kidney capsule of NSG mice.
Figure 7B:
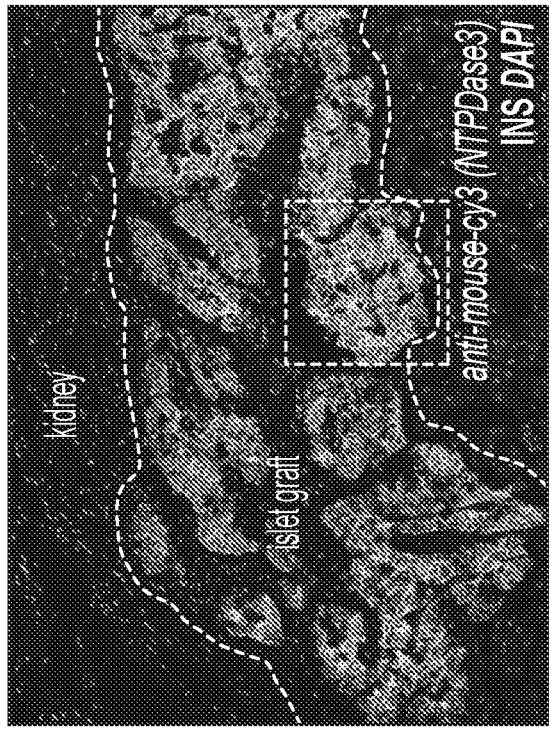
Figure 7A:
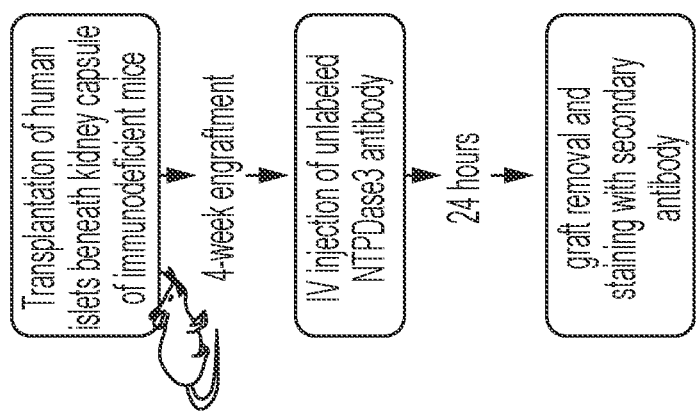
Figure 8A:
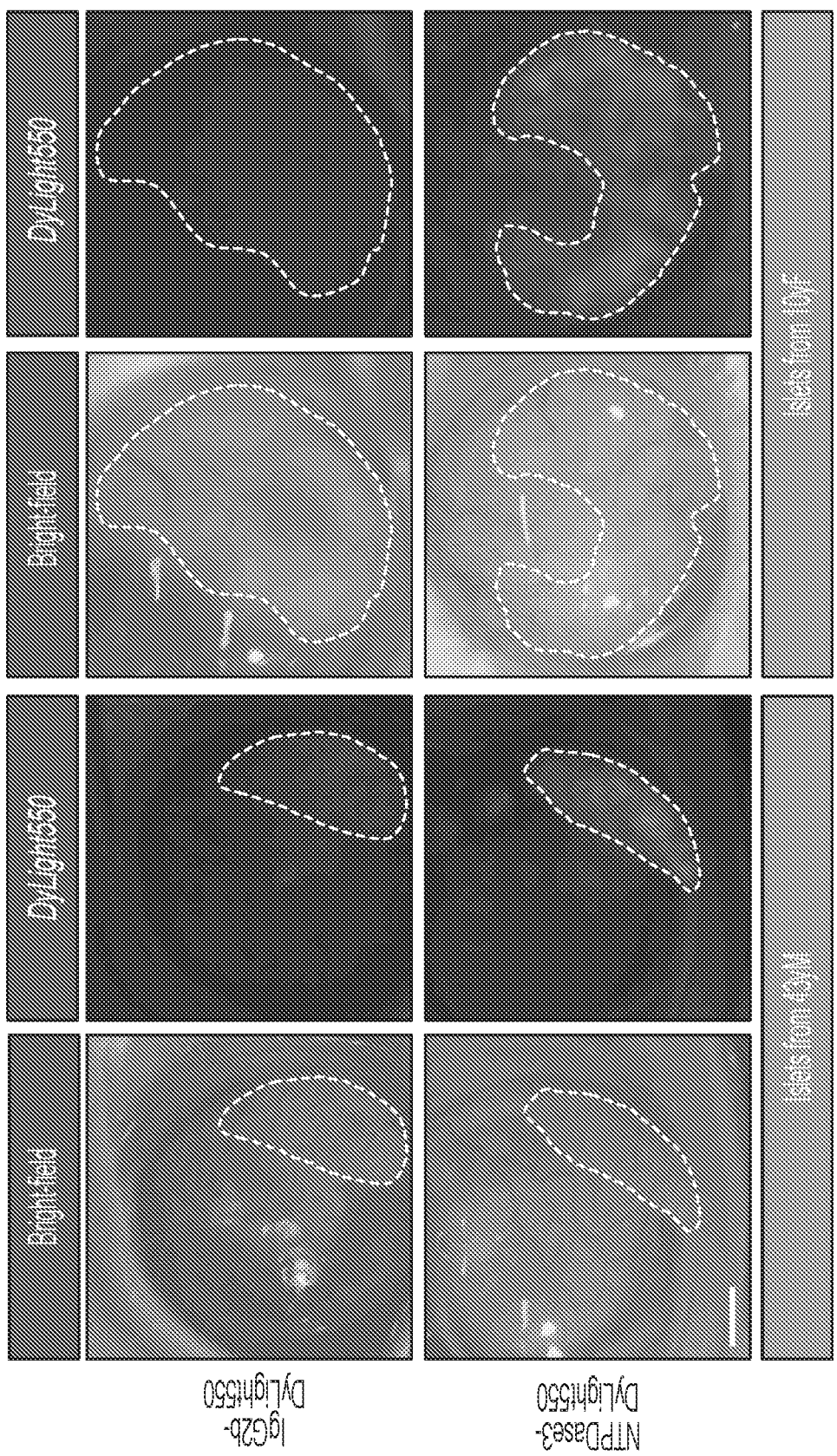
FIGS. 8A and 8B show that targeting NTPDase3 detects human β-cells in vivo.
Figure 8B:
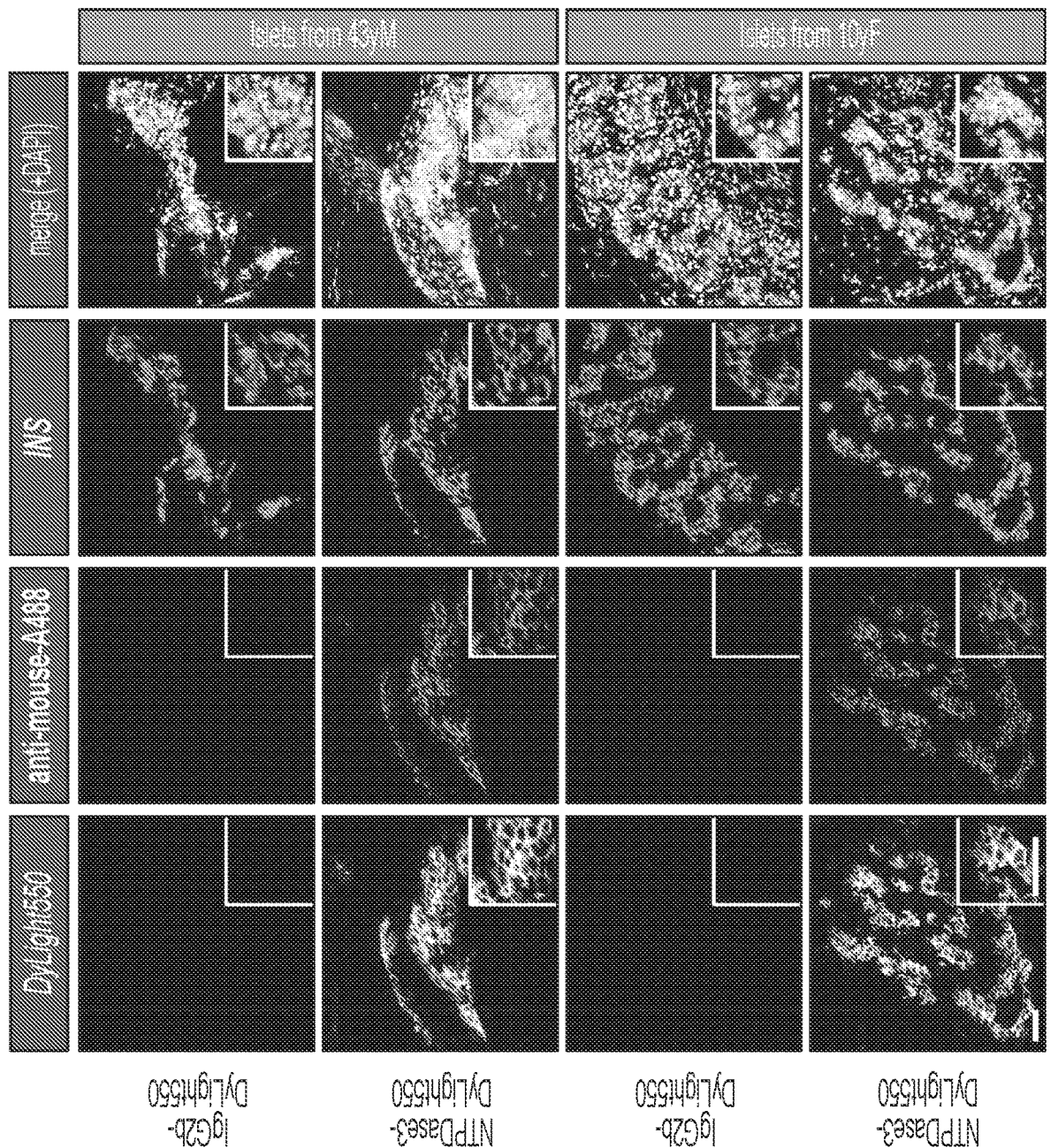

Since the NTPDase3 antibody allowed the sorting of live human β-cells, the ability to detect human β-cells in vivo was tested. To accomplish this, immunodeficient mice bearing human islets engrafted either under the kidney capsule or in the anterior chamber of the eye (ACE) were used (FIG. 6a). When mice received an intravenous injection of unlabeled NTPDase3 antibody and grafts were removed twenty-four hours later, visualization with a secondary antibody revealed that NTPDase3 bound β-cells in vivo with high specificity (FIG. 7). Next, the NTPDase3 antibody was conjugated to DyLight550 (FIG. 6a), injected the labeled antibody, and imaged the mice twenty-four hours post-injection. We observed fluorescent signal in the human islet grafts that was not present with an isotype control (FIGS. 6b and 8a). Immunohistochemistry on removed islet grafts confirmed this highly specific binding of the conjugated NTPDase3 antibody to human β-cells (FIGS. 6c and 8b). These data indicate that the antibody circulates, exits the vascular space, and reaches engrafted islet cells, where the NTPDase3 epitope is exposed on the β-cell surface in vivo. Such results indicate that the epitope is accessible in the native pancreas, which is important for imaging applications. The ability to quantify β-cell mass can also improve evaluation of clinical outcomes, ranging from assessment of islet transplantation to endogenous recovery of β-cell mass through pharmaceutical manipulation. The use of transplanted human islets notably expands the relevance of NTPDase3 as an in vivo imaging tool. These data provide key evidence of in vivo imaging characteristics lacked by other imaging agents and can enhance the understanding of β-cell mass dynamics, which has not been possible to study in humans. Additionally, in vitro analysis of T1D and T2D tissues indicates that NTPDase3 expression is not altered under pathophysiological conditions, a desirable quality of agents aimed at quantifying β-cell mass.

Diabetes is a major health concern worldwide, and its growing prevalence poses an increasing demand for effective therapeutic and preventative approaches. The disease is broadly classified as type 1 or type 2, with both types characterized by dysfunction or destruction of insulin-secreting β-cells of the Islets of Langerhans. The highly vascularized, highly innervated islet functions as a mini-organ, and its heterogeneous composition and anatomical location pose challenges particularly to identifying characteristics of individual cell subtypes in normal or disease states. Because of this, several groups have developed systems to isolate subpopulations of islet cells for transcriptional, metabolic, and functional analyses. These isolations are generally accomplished by dispersing and sorting cells using antibodies that target either cell surface antigens on live cells or intracellular proteins in fixed, permeabilized cells. Other groups have alternatively sorted β-cells based on zinc content, using the zinc-binding fluorochrome Newport Green. Each approach has advantages and drawbacks, but one critical limitation is the lack of a cell surface antibody that specifically targets human β-cells.

In addition to analyzing human β-cells ex vivo, there is great need to identify and visualize β-cells non-invasively in vivo. Indeed, although reduced β-cell mass is an established feature of diabetes progression, current knowledge has originated from post-mortem analysis because there are no effective methods to quantify β-cell mass non-invasively in humans. This limitation has greatly hindered the understanding of disease risk and progression and prevents the evaluation of interventions designed to preserve or increase β-cell mass. Many traditional imaging modalities lack necessary sensitivity for the small size and sparse distribution of islets, and better reagents are necessary to distinguish β-cells from other endocrine cells and neighboring exocrine tissue. Antibodies typically have greater specificity and affinity than other molecules such as peptides and small molecules, and multiple antibodies targeting islet cell surface antigens have unsuccessfully been tried for islet imaging applications in vivo.

In efforts to identify cell surface markers of human β-cells, the expression of nucleoside triphosphate diphosphohydrolase (NTPDase) 3, an enzyme localized to the endocrine islet in the human pancreas, was examined using a monoclonal antibody. NTPDase3 (encoded by gene ENTPD3) belongs to a group of ecto-enzymes whose function is to modulate local extracellular nucleotide levels, thereby affecting availability of ligands that mediate purinergic signaling. Isozyme NTPDase3 has been most studied in the rodent brain, where it is proposed to help regulate synaptic function, and it also is expressed in human brain, GI tract, and urinary bladder tissues as reported by the NIH Genotype-Tissue Expression (GTEx) program. Importantly, NTPDase3 is expressed in pancreatic islets of both human and rodents, and recent work has indicated activity in regulating insulin secretion.

b) Experimental Methods (1) Human Pancreas Procurement, Islet Isolation, and Preparation of Tissue for Histological Analysis Pancreata and islets from juvenile, adult, T1D, and T2D donors were obtained through partnerships with the International Institute for Advancement of Medicine (IIAM), National Disease Research Interchange (NDRI), Integrated Islet Distribution Program (IIDP), and Network for Pancreatic Organ Donors with Diabetes (nPOD) within 18 hours from cold clamp as described. Most pancreata from normal donors were processed either for islet isolation or histological analysis as described. Donor demographic information is summarized in Table 1. The Vanderbilt University Institutional Review Board does not classify de-identified human pancreatic specimens as human subject research. Pancreatic organs were processed for islet isolation in Pittsburgh and shipped to Vanderbilt University for further analysis following shipping protocols developed by the IIDP. Assays using isolated islets were performed within 48 hours of islet arrival.

TABLE 1

Demographic information of donors

| Donors | Age | Ethnicity/Race | Disease Duration | Gender | BMI | Cause of Death | Tissue/Islet Source |
|---|---|---|---|---|---|---|---|
| Normal Controls for Histology | G18 weeks | N/A | — | N/A | N/A | N/A | — |
| | 4 days | Caucasian | — | M | 13.1 | Anoxia | IIAM |
| | 2 months | African American | — | F | 13.4 | Head Trauma | IIAM |
| | 3 months | Hispanic/Latino | — | M | 16.1 | Head Trauma | NDRI |
| | 7 months | Hispanic/Latino | — | M | 17.3 | Head Trauma | IIAM |
| | 20 months | Caucasian | — | F | 23.4 | Anoxia | IIAM |
| | 5 years | African American | — | F | 15.9 | Anoxia | NDRI |
| | 10 years | Caucasian | — | M | 19.3 | Head trauma | NDRI |
| | 18 years | Caucasian | — | M | 31.4 | Head Trauma | IIAM |
| | 35 years | Caucasian | — | M | 26.8 | Head Trauma | IIAM |
| T1D, T2D Samples for Histology | 20 years | Caucasian | 7 years (T1D) | M | 25.5 | Anoxia | NDRI |
| | 47 years | Caucasian | 3 years (T2D) | M | 31.3 | Stroke | IIAM |
| | 49 years | Caucasian | 3 years (T2D) | F | 33.8 | Stroke | IIAM |
| Normal Controls for FACS Purity | 19 years | Caucasian | — | M | 27.2 | Head Trauma | IIDP |
| | 50 years | African American | — | M | 30.2 | Stroke | IIDP |
| Normal Controls for RNA - seq | 26 years | Hispanic/Latino | — | F | 35.9 | Anoxia | IIDP |
| | 35 years | Caucasian | — | F | 23.6 | Anoxia | IIDP |
| | 49 years | Caucasian | — | F | 31.6 | Stroke | IIDP |
| | 50 years | African American | — | M | 30.2 | Stroke | IIDP |
| | 55 years | Caucasian | — | M | 27.8 | Stroke | IIDP |
| Normal Controls | 10 years | Hispanic/Latino | — | F | 25.4 | Head Trauma | nPOD |

TABLE 1-continued

Demographic information of donors

| Donors | Age | Ethnicity/Race | Disease Duration | Gender | BMI | Cause of Death | Tissue/Islet Source |
|---|---|---|---|---|---|---|---|
| for Islet Transplants | 43 years | Caucasian | — | M | 35.0 | Stroke | IIDP |
| | 55 years | Caucasian | — | M | 30.1 | Head Trauma | IIDP |
| | 61 years | N/A | — | M | N/A | N/A | ADI |

ADI - Alberta Diabetes Institute;
IIAM - International Institute for the Advancement of Medicine;
IIDP - Integrated Islet Distribution Program;
N/A - not available;
NDRI - National Disease Research Interchange;
nPOD - Network for Pancreatic Organ Donors with Diabetes;
T1D - type 1 diabetes;
T2D - type 2 diabetes (2) Immunohistochemical Analysis Immunohistochemical analysis of pancreas was performed on serial 5-μm cryosections as described. Primary antibodies to all antigens and their working dilutions are listed in Table 2. The antigens were visualized using appropriate secondary antibodies listed in Table 3. Digital images were acquired with a Zeiss LSM510 META laser scanning confocal microscope (Carl Zeiss).

TABLE 2

Primary antibodies for immunohistochemistry, flow cytometry, and in vivo imaging

| Antigen | Species | Dilution | Application | Source | Catalog # |
|---|---|---|---|---|---|
| Amylase | Rabbit | 1:1000 | IHC | Sigma | A8273 |
| CD39L3 (NTPDase3) | Mouse | 1:50 | IHC, FC | gift of J. Sévigny | N/A |
| Glucagon | Rabbit | 1:100 | IHC | Cell Signaling | 2760s |
| HIC0-4F9 [Biotin] (HPi1) | Mouse | 1:100 | FC | Novus | NBP1-18872B |
| HIC3-2D12 (HPa3) | Mouse | 1:200 | FC | ALPCO | 77-HPA3-PU-0.1 |
| IgG2b Isotype Control [DyLight550-conjugated] | Mouse | — | IVI | Novus | NBP2-27231R |
| Insulin | Guinea Pig | 1:500 | IHC | Dako | A0564 |
| Pancreatic Polypeptide | Rabbit | 1:1000 | IHC | Bachem | T-4088 |
| Somatostatin | Goat | 1:500 | IHC | Santa Cruz | sc7819 |

FC - flow cytometry;
IHC - immunohistochemistry;
IVI - in vivo imaging;
N/A - not available

TABLE 3

Secondary antibodies for immunohistochemistry and flow cytometry

| Host Species | Primary Ab Species | Fluorophore | Dilution | Application | Source | Catalog # |
|---|---|---|---|---|---|---|
| Donkey | Goat | Cy5 | 1:200 | IHC | Jackson Immunoresearch | 705-175-147 |
| Donkey | Guinea Pig | Cy2 | 1:500 | IHC | Jackson Immunoresearch | 706-225-148 |
| Donkey | | Cy3 | 1:500 | IHC | Jackson Immunoresearch | 706-165-148 |
| Donkey | | Cy5 | 1:200 | IHC | Jackson Immunoresearch | 706-175-148 |
| Donkey | Mouse | Alexa 488 | 1:500 | IHC | Jackson Immunoresearch | 715-545-150 |
| Donkey | | Cy2 | 1:500 | IHC | Jackson Immunoresearch | 715-225-150 |
| Donkey | | Cy3 | 1:500 | IHC | Jackson Immunoresearch | 715-165-150 |
| Donkey | | Cy5 | 1:200 | IHC | Jackson Immunoresearch | 715-175-150 |
| Donkey | Rabbit | Cy2 | 1:500 | IHC | Jackson Immunoresearch | 711-225-152 |
| Donkey | | Cy5 | 1:200 | IHC | Jackson Immunoresearch | 711-175-152 |
| Goat | Mouse | APC | 1:500 | FC | Becton Dickinson | 550826 |
| Goat | Mouse | PE | 1:1000 | FC | Becton Dickinson | 550589 |

TABLE 3-continued

Secondary antibodies for immunohistochemistry and flow cytometry

| Host Species | Primary Ab Species | Fluoro-phore | Dilution | Application | Source | Catalog # |
|---|---|---|---|---|---|---|
| — | Strep | BV421 | 1:500 | FC | Becton Dickinson | 563259 |

FC - flow cytometry;
IHC - immunohistochemistry;
Strep - streptavidin (3) Culture and Assessment of Pancreatic Islet Function In Vitro Upon arrival at Vanderbilt University, human islets were cultured in CMRL1066 media (5.5 mM glucose, 10% FBS, 1% Pen/Strep, 2 mM L-glutamine) in 5% $CO_2$ at 37° C. for 0-48 hours prior to reported studies. Normal function of islets from adult controls (Table 1) was confirmed using a dynamic cell perifusion system and radioimmunoassay.

(4) α- and β-Cell Sorting by Flow Cytometry

Human islets from five normal donors (ages 26-55 years, BMI 24-36) were dispersed using a modified protocol. Briefly, 0.025% trypsin was used to disperse cells and reaction was quenched with modified RPMI medium (10% FBS, 1% Penn/Strep, 5 mM glucose). Cells were washed in the same medium and counted on a hemocytometer, then transferred to FACS buffer (2 mM EDTA, 2% FBS, 1×PBS). Indirect antibody labeling was completed via two sequential incubation periods at 4C, with one wash in FACS buffer following each incubation. Primary (HPi1, HPa3, NTPDase3) and secondary antibodies, are listed in Tables 2 and 3 and were used to isolate high-quality RNA from α- and β-cells. Appropriate single color compensation controls were run alongside samples. Prior to sorting, propidium iodide (0.05 ug/100,000 cells; BD Biosciences) was added to samples for non-viable cell exclusion. Flow analysis was performed using an LSRFortessa cell analyzer (BD Biosciences), and a FACSAria III cell sorter (BD Biosciences) was used for FACS. Analysis of flow cytometry data was completed using FlowJo 10.1.5 (Tree Star). Gating strategy is shown in FIG. 5. Where indicated, a subset of collected cells was washed 2× in PBS and collected onto a Plus Gold slide (Fisher Scientific) using a Cytospin 4 cytocentrifuge (ThermoFisher), then fixed in 4% PFA for 10 minutes prior to immunocytochemical analysis.

(5) RNA-Sequencing

Sorted α- and β-cells (9,000-123,000) were stored in 200 μL lysis/binding solution (Ambion) at −80° C. prior to RNA isolation using the RNAqueous micro-scale phenol-free total RNA isolation kit (Ambion). Trace DNA was removed with TURBO DNA-free (Ambion), RNA integrity was evaluated (Agilent 2100 Bioanalyzer; 8.11±0.34 RIN, n=10), and high-integrity total RNA was amplified (Ovation system; NuGen Technologies) per standard protocol. Amplified cDNA was sheared to target 200 bp fragment size and libraries were prepared using NEBNext DNA Library Prep (New England BioLabs). 50 bp Paired End (PE) sequencing was performed on an Illumina HiSeq 2500 using traditional Illumina methods to generate approximately 50 million reads per sample. Raw reads were mapped to the reference human genome hg19 using TopHat v2.1. Aligned reads were then imported onto the Avadis NGS analysis platform (Strand life Sciences) and filtered based on read quality followed by read statistics to remove duplicates. Transcript abundance was quantified using the TMM (Trimmed Mean of M-values) algorithm as the normalization method.

(6) RNA-Sequencing Analysis

Genes with normalized expression values less than 25 were removed prior to differential expression analysis between control and T1D groups. Fold change (cutoff≥±1.5) was calculated based on p-value estimated by z-score calculations (cutoff 0.05) as determined by Benjamini Hochberg false discovery rate (FDR) correction of 0.05. Differentially expressed genes were further analyzed through Ingenuity Pathway Analysis (IPA, Qiagen) and Gene Ontology (GO) analysis using DAVID v6.8. The accession number for the sequencing data reported in this paper is GEO: GSEXXXX.

(7) Islet Transplantation into Immunodeficient Mice

Immunodeficient 10-12 week old NOD-scid-IL2ry$^{null}$ (NSG) male mice (Jax) were used for human islet transplantation studies. Animals were maintained by Vanderbilt Division of Animal Care in group housing in sterile containers within a pathogen-free barrier facility housed with a 12 hr light/12 hr dark cycle and access to free water and standard rodent chow. All animal procedures were approved from by the Vanderbilt Institutional Animal Care and Use Committees. Human islets from four normal donors (ages 10-61 years, BMI 25-35) were obtained through IIDP, ADI, and nPOD (Table 1). For each set of islets, 3-5 mice were transplanted with 100 islet equivalents each into the anterior chamber of the eye (ACE). Islets were allowed to engraft for 1 month prior to imaging.

(8) In Vivo Imaging

Mice were anesthetized using a standard dose of isoflurane and injected with 100 μL of saline containing 30 μg of DyLight550-conjugated NTPDase3 antibody (Vanderbilt Antibody and Protein Resource) or isotype control (Novus) into the left retro-orbital space. After recovery for 24 hours, mice were again anesthetized and placed on the microscope stage with right eye facing up and oriented to reveal islet graft (visible under white light). Images showing the iris bearing grafted islets were obtained using an Olympus SZX12 fluorescent stereo zoom microscope equipped with a DP80 camera (Olympus). Following imaging, mice were sacrificed and grafts were removed and fixed according to the standard protocol for pancreas fixation (described above).

2. Example 2: New, Complementary Pre-Clinical Models to Evaluate Potential Islet Imaging Agents In the first model, the transgenic expression of the luciferase optical reporter gene (MIP-Luc-VU) in mouse beta cells enables bioluminescence imaging to accurately quantifies beta cell mass under conditions of increased or decreased beta cell mass and after islet transplantation. MIP-Luc-VU mice were bred with mice engineered to express the Diphtheria toxin (DT) receptor on the beta cell to create a new model (MIP-Luc-VU/RIP-DTR). Administration of DT results in rapid, specific, and near complete (>99%) ablation of beta cells (FIG. 9a) and allows the beta cell mass to be imaged before and after beta cell-specific ablation. However, the commonly used approach for ablating beta cells to evaluate imaging agents with streptozotocin (STZ) is problematic. While STZ models have been used to identify several agents that appeared to bind the islet, there are concerns about the specificity and off-target toxicity of STZ. For example, in addition to its toxicity to the beta cell, STZ also exhibits renal and hepatic toxicity. As these two organs are major excretion routes for many radiotracers, STZ may affect radiotracer biodistribution to the pancreas. Furthermore, streptozotocin was recently shown to reduce the amount of non-specific exocrine binding of [$^{11}$C]DTBZ, leading to a reduction in pancreatic signal that does not truly reflect beta cell mass. The new model of bioluminescence imaging and beta cell ablation (MIP-Luc-VU/RIP-DTR) provides an improved approach for evaluating islet-directed imaging agents with faster and more complete beta cell ablation than STZ, without the non-specific toxicity of STZ.

In the second model, luciferase was expressed in human islets with an adenovirus and after transplantation into immunodeficient mice, the human islets were imaged in vivo using bioluminescence imaging (BLI). The BLI persists for months after transplantation into immunodeficient hosts and there is a linear relationship between BLI and the number of islets, both in vitro and in vivo.

These complementary and synergistic models allow one to determine the islet specificity of imaging ligands and furthermore, enable the in vivo study of human islets, which are now known to have important differences from rodent islets. These two models were used to assess the sensitivity and specificity of new agents developed to target VMAT-2 (exact agents are propriety information protected by collaborative agreement). Following DT administration, MIP-Luc-VU/RIP-DTR mice had near complete beta cell destruction (FIG. 9a) and developed severe hyperglycemia (FIG. 9b). These same DT-treated mice displayed a concordant decrease in pancreatic bioluminescence intensity (FIGS. 9c and 9d). In contrast, PET imaging of the very same mice with a DTBZ-based PET imaging agent revealed no change in the pancreatic signal (FIG. 9e) or the biodistribution of the radiotracer, as assessed in dissected organs (FIG. 9f). Using the human islet transplant model, it was found that the labeled DTBZ ligand did not bind human islets in vivo. Taken together, these data indicate that the pancreatic PET signal reported in prior rat and human studies was not due to accumulation of radiotracer in beta cells, but was most likely due to non-endocrine cells in the pancreas. Such a conclusion could not have been reached without multimodal imaging of inducible, selective and extreme beta cell ablation and the human islet transplant model.

3. Example 3: Co-Registration of Multi-Modal Imaging

Figure 10C:
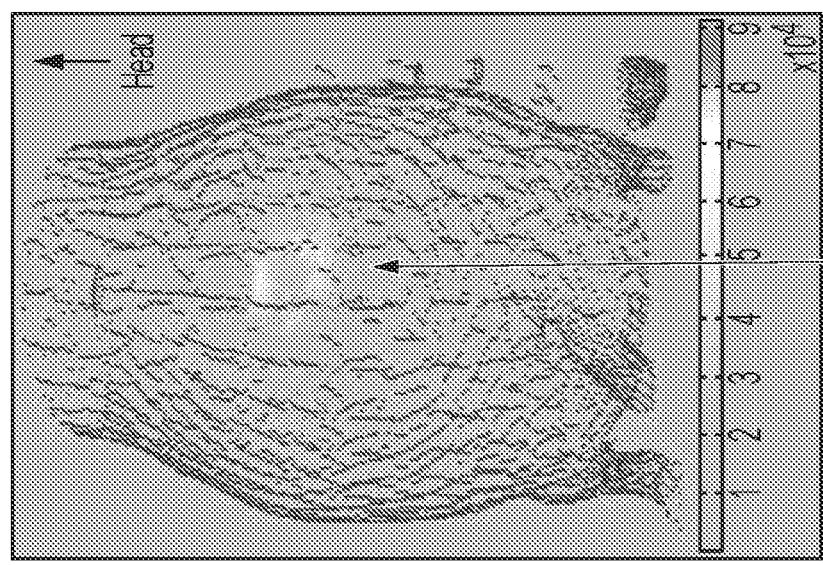
FIGS. 10A, 10B, 10C, 10D, and 10E show that co-registration of bioluminescence tomography and PET images enables delineation of the pancreas from surrounding organs and accurate evaluation of pancreatic radiotracer uptake.
Figure 10B:
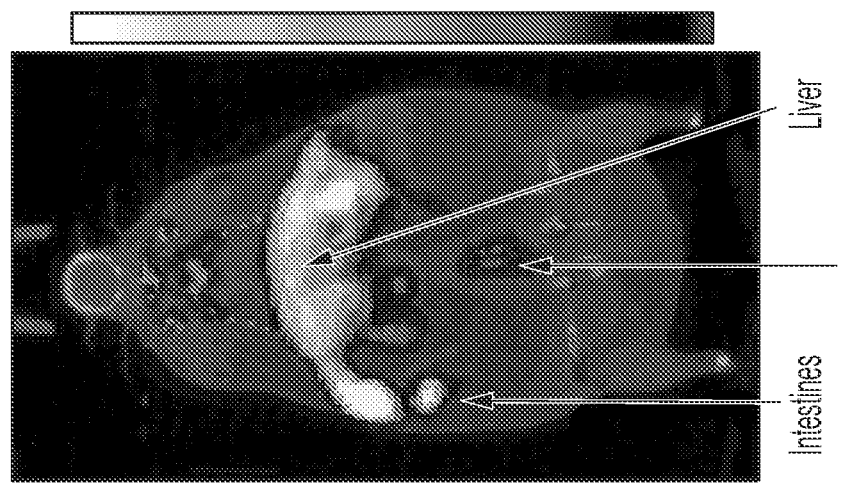
Figure 10A:
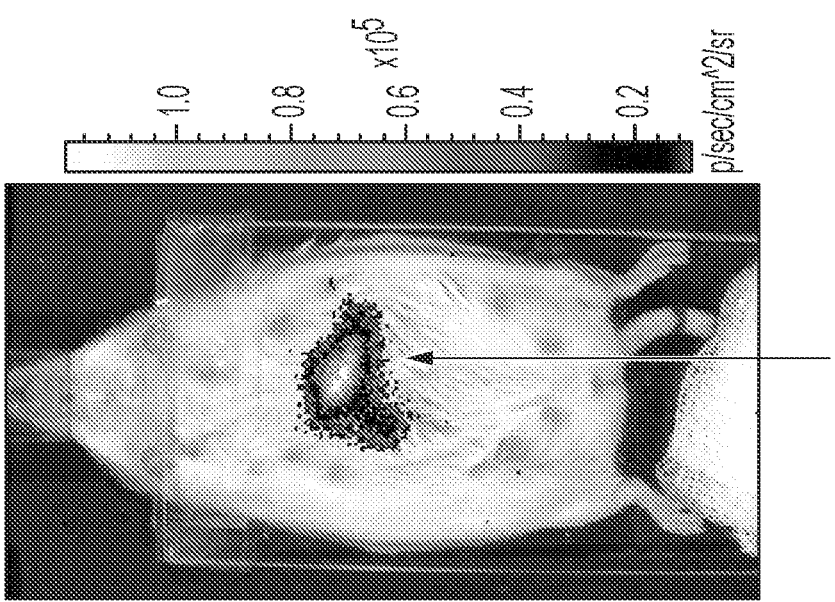
Figure 10D:
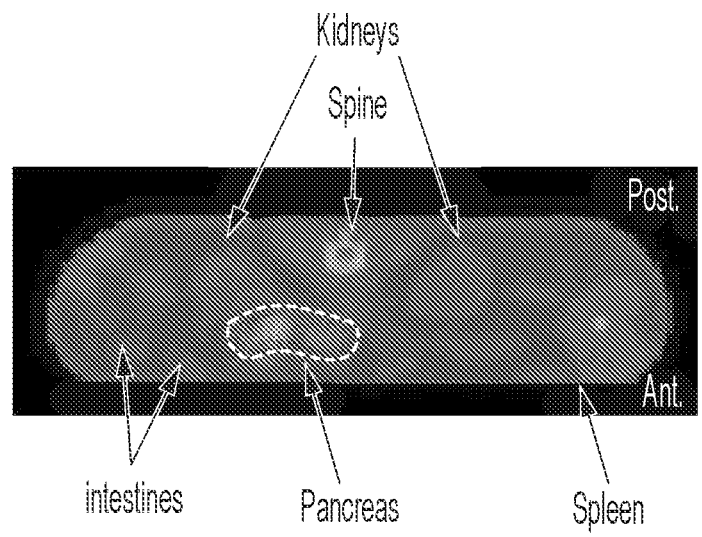
Figure 10E:
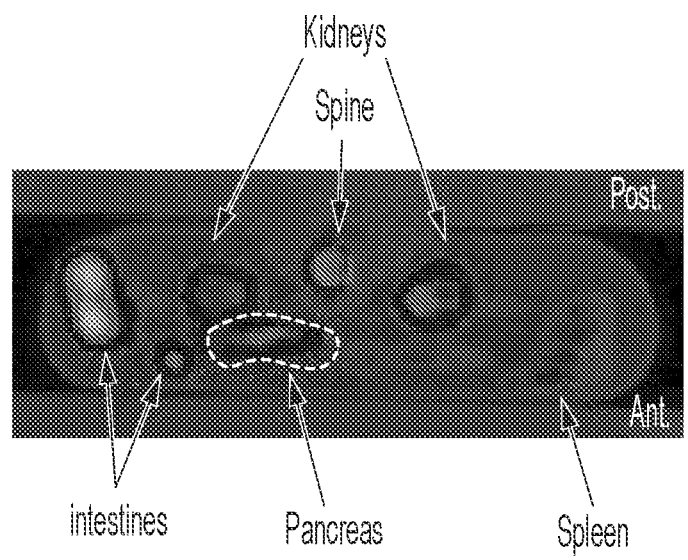

An algorithm was developed for reconstructing bioluminescent source location in 3-D and for co-registering this with PET/SPECT/CT images to spatially delineate the pancreas on the nuclear image. The scattering of light by biological tissue has hampered studies seeking to track cell migration, locate tumor metastasis, or spatially localize transgene expression using bioluminescence imaging. However, newly developed techniques for reconstructing the bioluminescent source location from surface projection images are under development to address these limitations. Three-dimensional bioluminescence tomography permits more accurate quantification of bioluminescence results and enables localization of bioluminescent sources in three-dimensional space. Bioluminescence tomography of MIP-Luc mice was performed which emit bioluminescence (BLI) solely from the beta cells of the pancreas (FIG. 10a). PET/CT imaging of MIP-Luc-VU/RIP-DTR mice after radiotracer administration showed uptake in the pancreas, as well as uptake in the liver, intestines, spleen, and bladder (FIG. 10b), and a few regions of the central nervous system. The proximity of the former abdominal set of organs to the pancreas prevented the accurate delineation of a region of interest (ROI) encompassing solely the pancreas on PET images. An algorithm was implemented for reconstructing bioluminescence source location in three-dimensional space (FIG. 10c). This reconstruction was co-registered, which demonstrated bioluminescence only in the pancreas (FIG. 10d), with PET and computed tomography (CT) images of the same axial slices (FIG. 10e). The PET/CT co-registration of the axial slice showed radiotracer uptake in the pancreas and in neighboring organs (FIG. 10e). An ROI comprising only the pancreas (red dashed line) was defined using the tomographic bioluminescence image (FIG. 10d) and co-registered with the PET image (FIG. 10e). This co-registration allows for unambiguous delineation of the pancreas ROI in the PET image (FIGS. 10d and 10e), which enabled the quantification of the PET pancreatic signal while preventing the confounding influence of radiotracer in adjacent organs.

4. Example 4: Perform Multi-Modal Imaging and Co-Register Images in Preclinical Models with Mouse or Human Islets The location of transplanted islets or the pancreas can be difficult to delineate, but by using a mouse model expressing luciferase in the islet and an algorithm that enables three-dimensional reconstruction of bioluminescent sources islets can be delineated in three dimensional space and co-registered with other imaging modalities.

a) Experimental Approach and Outcome Parameters.

The bioluminescence tomography image can be co-registered with the SPECT and fluorescence tomography image to delineate the pancreas or islet graft. An ROI encompassing the pancreas/islet graft can then be unambiguously drawn on the SPECT and fluorescence tomography images. Measurement of the pancreatic or islet graft fluorescence and radioactivity can be correlated with BLI. Ex vivo measurements of pancreatic or islet graft bioluminescence, fluorescence, and radioactivity can be used to validate in vivo measurements.

Bioluminescence imaging (BLI) can be performed using an IVIS 200 CCD camera. In order to perform three-dimensional bioluminescence tomography, anesthetized mice can be immobilized in an animal imaging cassette, which enables image acquisition from both ventral and dorsal sides of the animal. Dorsal and ventral spectrally-filtered images can be taken through six 20-nm bandpass filters, at wavelengths from 560 to 660 nm using the IVIS 200 CCD camera.

The bioluminescence projection images can be mapped to the fluorescence tomography and SPECT/CT images using a mutual information algorithm. A triangular finite element mesh can be generated from the CT image using Matlab. The internal bioluminescence source distribution can then be reconstructed from the surface light map using Matlab, by solving the NIRFAST inverse diffusion approximation of light propagation. As the MIP-Luc-VU model and bioluminescent human islet transplant model express luciferase only in the islet, the reconstruction can delineate the pancreas or islet graft. Due to the previous image space mapping step, the bioluminescence tomography image (delineating the pancreas/islet graft) and the fluorescence tomography and SPECT image (displaying biodistribution of the tracer) can be co-registered in three-dimensional space.

b) Results

The co-registered bioluminescence tomography image can be used to delineate a pancreatic/islet graft ROI on the fluorescence tomography and SPECT images. This allows a ROI to be defined on the fluorescence tomography and SPECT image which encompasses solely the pancreas or islet graft, without confounding signal from neighboring organs clearing the antibody or radiolabeled effector. This enables accurate quantitation of the signal that arises only from the pancreas or islet graft.

As bioluminescence tomography requires spectral filtering of the bioluminescent signal, weak signals can be difficult to image, especially for short wavelengths. However, the MIP-Luc-VU mouse and transplanted human islets each provides a robust optical signal for the reconstruction. Another limitation to bioluminescence tomography is that biological tissue is optically heterogeneous: different organs absorb and scatter light at different rates. The inclusion of a co-registered CT image in these scans can be used to account for optical heterogeneity and increase the accuracy of the bioluminescence tomography algorithm.

5. Example 5: Determine the Correlation of Pre-Targeted SPECT Imaging and BLI in Pre-Clinical Models with Increased or Decreased Islet Cell Mass This disclosure shows how well SPECT measurements with the five antibodies in Table 4 reflect $\beta$ cell mass as quantified by BLI and standard post-mortem measurements of $\beta$ cell mass.

TABLE 4

Antibodies to be used for islet imaging in this proposal

| Antibody name | Antibody name in prior publications | Information about the antibody | Hybridoma Source |
|---|---|---|---|
| Mab-1 | 1038; HPi1; HICO 4-F9 | Reacts with all islet endocrine cell types (human) | BCBC |
| Mab-2 | 1038B; HPi4; HIC1 5-F10 | Reacts with all islet endocrine cell types (human) | BCBC |
| Mab-3 | 1038E; HPi3; HIC1 7-H10 | Reacts with all islet endocrine cell types (human) | BCBC |
| Mab-4 | Ab2537 (F66) | Reacts with all islet endocrine cell types (mouse and human); antigen - Disp2 (related to dispatched SH-receptor; no known function)* | BCBC; |
| Mab-5 | A2B5 | Reacts with cell-surface ganglioside on all islet endocrine cell types (mouse and human); also reacts with ganglia, thymic epithelium and selected stem cell populations | ATCC |

BCBC - Beta Cell Biology Consortium;
ATCC - American Tissue Cell Culture;
*personal communication, Ole Madsen a) Experimental Approach and Outcome Parameters.

Human islets can be obtained from any reasonable source, including, but not limited to subjects and the Juvenile Diabetes Foundation Human Islet Distribution Program, shipped in CMRL media by overnight courier to Vanderbilt, and assessed for viability in a cell-perifusion system. Islets can be transfected overnight with an adenovirus (Adv-luciferase) that encodes firefly luciferase under the control of the cytomegalovirus (CMV) promoter. To examine the imaging signal over a range of human islet mass, human islets can be transplanted into normoglycemic NOD-SCID gamma mice, in quantities of 500, 1000, or 2000 islets.

To examine the imaging signal when beta cell mass is reduced, MIP-Luc-VU/RIP-DTR mice (male) can be injected with diphtheria toxin (DT) in a single intraperitoneal injection of 125 ng diphtheria toxin to render the mice diabetic. SPECT, fluorescence tomography, and bioluminescence tomography imaging can similarly be performed on mice prior to DT treatment.

To examine the imaging signal when beta cell mass is increased, MIP-Luc-VU/RIP-DTR mice (male) can be placed on a high-fat diet. SPECT, fluorescence tomography, and bioluminescence tomography imaging can similarly be performed on mice prior when the diet is started and every two weeks for the 12 week duration of the diet.

After injection of the antibody, the mouse can then be transferred to the Visen FMT 2500 and imaged for fluorescence.

Pancreatic SPECT measurements can also be correlated with post mortem measurements of beta cell mass as assessed by morphometric analysis of pancreatic sections and pancreatic insulin content. After imaging, the pancreas can be removed and imaged for fluorescence and radioactivity. In all models, pancreatic islet mass can be assessed by standard procedures in the laboratory (pancreatic insulin content, immunocytochemical and morphometric assessment, and BLI).

To determine whether the cell surface expression of the ligand is altered by the extracellular glucose concentration, a competition-binding assay can be performed by co-incubation of the labeled antibody with an excess of unlabeled antibody using mouse or human islets cultured in glucose concentrations of 2.8, 5.6, 11.0, and 16.7 mM for 48 hours prior to the in vitro binding assay.

b) Results

SPECT imaging of the pancreas correlates with BLI and post mortem measurements of beta cell mass, with lower activity after DT treatment or the high-fat diet. Mice bearing transplanted human islets display a SPECT signal proportional to the number of islets transplanted.

C. REFERENCES

Aamodt, K. I. et al. Development of a reliable automated screening system to identify small molecules and biologics that promote human β-cell regeneration. American Journal of Physiology—Endocrinology and Metabolism 311, E859-E868 (2016).

Abdulreda, M. H., Caicedo, A. & Berggren, P.-O. Transplantation into the anterior chamber of the eye for longitudinal, non-invasive in vivo imaging with single-cell resolution in real-time. J Vis Exp e50466 (2013). doi: 10.3791/50466

Ahlgren U, Gotthardt M. Approaches for imaging islets: recent advances and future prospects. Adv Exp Med Biol. 2010; 654:39-57.

Antonioli, L., Blandizzi, C., Csoka, B., Pacher, P. & Hasko, G. Adenosine signalling in diabetes mellitus—pathophysiology and therapeutic considerations. Nature Reviews Endocrinology 11, 228-241 (2015).

Balamurugan, A. N., Chang, Y., Fung, J. J., Trucco, M. & Bottino, R. Flexible management of enzymatic digestion improves human islet isolation outcome from sub-optimal donor pancreata. Am. J. Transplant. 3, 1135-1142 (2003).

Blodgett, D. M. et al. Novel Observations From Next-Generation RNA Sequencing of Highly Purified Human Adult and Fetal Islet Cell Subsets. Diabetes 64, 3172-3181 (2015).

Bonner-Weir S, Trent D F, Weir G C. Partial pancreatectomy in the rat and subsequent defect in glucose-induced insulin release. The Journal of clinical investigation. 1983; 71(6):1544-53.

Bonner-Weir S. Life and death of the pancreatic beta cells. Trends Endocrinol Metab. 2000; 11(9):375-8.

Bramswig, N. C. et al. Epigenomic plasticity enables human pancreatic α to β cell reprogramming J Clin. Invest. 123, 1275-1284 (2013).

Brissova M, Fowler M, Wiebe P, Shostak A, Shiota M, Radhika A, et al. Intraislet endothelial cells contribute to revascularization of transplanted pancreatic islets. Diabetes. 2004; 53(5):1318-25.

Brissova M, Shiota M, Nicholson W E, Gannon M, Knobel S M, Piston D W, et al. Reduction in pancreatic transcription factor PDX-1 impairs glucose-stimulated insulin secretion. The Journal of biological chemistry. 2002; 277(13):11225-32.

Brissova M, Shostak A, Shiota M, Wiebe P O, Poffenberger G, Kantz J, et al. Pancreatic islet production of vascular endothelial growth factor—a is essential for islet vascularization, revascularization, and function. Diabetes. 2006; 55(11):2974-85.

Brissova, M. et al. a Cell Function and Gene Expression Are Compromised in Type 1 Diabetes. Cell Reports 22, 1-11 (2018).

Brissova, M. et al. Islet microenvironment, modulated by vascular endothelial growth factor-A signaling, promotes β cell regeneration. Cell Metabolism 19, 498-511 (2014).

Brom M, Andralojc K, Oyen W J, Boerman O C, Gotthardt M. Development of radiotracers for the determination of the beta-cell mass in vivo. Curr Pharm Des. 2010; 16(14): 1561-7.

Butler A E, Janson J, Bonner-Weir S, Ritzel R, Rizza R A, Butler P C. Beta-cell deficit and increased beta-cell apoptosis in humans with type 2 diabetes. Diabetes. 2003; 52(1):102-10.

Chaudhari A J, Darvas F, Bading J R, Moats R A, Conti P S, Smith D J, et al. Hyperspectral and multispectral bioluminescence optical tomography for small animal imaging. Physics in medicine and biology. 2005; 50(23): 5421-41.

Clark P B, Gage H D, Brown-Proctor C, Buchheimer N, Calles-Escandon J, Mach R H, et al. Neurofunctional imaging of the pancreas utilizing the cholinergic PET radioligand [18F]4-fluorobenzyltrozamicol. European journal of nuclear medicine and molecular imaging. 2004; 31(2):258-60.

Coutinho-Silva, R., Parsons, M., Robson, T. & Burnstock, G. Changes in expression of P2 receptors in rat and mouse pancreas during development and ageing. Cell Tissue Res 306, 373-383 (2001).

Coutinho-Silva, R., Parsons, M., Robson, T., Lincoln, J. & Burnstock, G. P2X and P2Y purinoceptor expression in pancreas from streptozotocin-diabetic rats. Molecular and Cellular Endocrinology 204, 141-154 (2003).

Davalli A M, Ogawa Y, Scaglia L, Wu Y J, Hollister J, Bonner-Weir S, et al. Function, mass, and replication of porcine and rat islets transplanted into diabetic nude mice. Diabetes. 1995; 44(1):104-11.

Davalli A M, Scaglia L, Zangen D H, Hollister J, Bonner-Weir S, Weir G C. Early changes in syngeneic islet grafts: effect of recipient's metabolic control on graft outcome. Transplant Proc. 1995; 27(6):3238-9.

de la Tour D, Halvorsen T, Demeterco C, Tyrberg B, Itkin-Ansari P, Loy M, et al. Beta-cell differentiation from a human pancreatic cell line in vitro and in vivo. Molecular endocrinology (Baltimore, Md. 2001; 15(3):476-83.

Dehghani H, Davis S C, Jiang S, Pogue B W, Paulsen K D, Patterson M S. Spectrally resolved bioluminescence optical tomography. Optics letters. 2006; 31(3):365-7.

Dehghani H, Davis S C, Pogue B W. Spectrally resolved bioluminescence tomography using the reciprocity approach. Medical physics. 2008; 35(11):4863-71.

Dehghani H, Eames M E, Yalavarthy P K, Davis S C, Srinivasan S, Carpenter C M, et al. Near infrared optical tomography using NIRFAST: Algorithm for numerical model and image reconstruction. Communications in numerical methods in engineering. 2008; 25(6):711-32.

Dillies, M.-A. et al. A comprehensive evaluation of normalization methods for Illumina high-throughput RNA sequencing data analysis. Brief. Bioinformatics 14, 671-683 (2013).

Dorrell C, Abraham S L, Lanxon-Cookson K M, Canaday P S, Streeter P R, Grompe M. Isolation of major pancreatic cell types and long-term culture-initiating cells using novel human surface markers. Stem cell research. 2008; 1(3):183-94.

Dorrell, C. et al. Human islets contain four distinct subtypes of β cells. Nat Commun 7, 11756 (2016).

Dorrell, C. et al. Isolation of mouse pancreatic alpha, beta, duct and acinar populations with cell surface markers. Molecular and Cellular Endocrinology 339, 144-150 (2011).

Dorrell, C. et al. Transcriptomes of the major human pancreatic cell types. Diabetologia 54, 2832-2844 (2011).

Eisenbarth G S, Shimizu K, Bowring M A, Wells S. Expression of receptors for tetanus toxin and monoclonal antibody A2B5 by pancreatic islet cells. Proceedings of the National Academy of Sciences of the United States of America. 1982; 79(16):5066-70.

Enge, M. et al. Single-Cell Analysis of Human Pancreas Reveals Transcriptional Signatures of Aging and Somatic Mutation Patterns. Cell 171, 321-330.e14 (2017).

Eriksson O, Jahan M, Johnstrom P, Korsgren O, Sundin A, Halldin C, et al. In vivo and in vitro characterization of [18F]-FE-(+)-DTBZ as a tracer for beta-cell mass. Nuclear medicine and biology. 2010; 37(3):357-63.

Eriksson, O. et al. In vivo imaging of beta cells with radiotracers: state of the art, prospects and recommendations for development and use. Diabetologia 59, 1340-1349 (2016).

Fagerholm V, Mikkola K K, Ishizu T, Arponen E, Kauhanen S, Nagren K, et al. Assessment of islet specificity of dihydrotetrabenazine radiotracer binding in rat pancreas and human pancreas. J Nucl Med. 2010; 51(9):1439-46.

Fowler M, Virostko J, Chen Z, Poffenberger G, Radhika A, Brissova M, et al. Assessment of pancreatic islet mass after islet transplantation using in vivo bioluminescence imaging. Transplantation. 2005; 79(7):768-76.

Gepts W, Lecompte P M. The pancreatic islets in diabetes. The American journal of medicine. 1981; 70(1):105-15.

Gepts W. Pathologic anatomy of the pancreas in juvenile diabetes mellitus. Diabetes. 1965; 14(10):619-33.

Goland R, Freeby M, Parsey R, Saisho Y, Kumar D, Simpson N, et al. 11C-dihydrotetrabenazine PET of the pancreas in subjects with long-standing type 1 diabetes and in healthy controls. J Nucl Med. 2009; 50(3):382-9.

Gotthardt M, Boermann O C, Behr T M, Behe M P, Oyen W J. Development and clinical application of peptide-based radiopharmaceuticals. Curr Pharm Des. 2004; 10(24): 2951-63.

Gotthardt M. Beta cell imaging—why we need it and what has been achieved. Curr Pharm Des. 2010; 16(14):1545-6.

Hampe C S, Wallen A R, Schlosser M, Ziegler M, Sweet I R. Quantitative evaluation of a monoclonal antibody and its fragment as potential markers for pancreatic beta cell mass. Exp Clin Endocrinol Diabetes. 2005; 113(7):381-7.

Hanley S C, Austin E, Assouline-Thomas B, Kapeluto J, Blaichman J, Moosavi M, et al. {bet}-Cell mass dynamics and islet cell plasticity in human type 2 diabetes. Endocrinology. 2010; 151(4):1462-72.

Hague, A., Engel, J., Teichmann, S. A. & Lonnberg, T. A practical guide to single-cell RNA-sequencing for biomedical research and clinical applications. Genome Med 9, 1-12 (2017).

Holliger P, Hudson P J. Engineered antibody fragments and the rise of single domains. Nature biotechnology. 2005; 23(9):1126-36.

Huang, D. W. et al. Extracting biological meaning from large gene lists with DAVID. Curr Protoc Bioinformatics Chapter 13, Unit 13.11-13.11.13 (2009).

Hutton J C, Davidson H W. Getting beta all the time: discovery of reliable markers of beta cell mass. Diabetologia. 2010; 53(7):1254-7.

Imai K, Takaoka A. Comparing antibody and small-molecule therapies for cancer. Nature reviews. 2006; 6(9): 714-27.

Itkin-Ansari P, Geron I, Hao E, Demeterco C, Tyrberg B, Levine F. Cell-based therapies for diabetes: progress towards a transplantable human beta cell line. Annals of the New York Academy of Sciences. 2003; 1005:138-47.

Kaplan E L, Meier P. Nonparametric Estimation from Incomplete Observations. Journal of the American Statistical Association. 1958; 53(282):457-81.

Kayton, N. S. et al. Human islet preparations distributed for research exhibit a variety of insulin-secretory profiles. American Journal of Physiology—Endocrinology and Metabolism 308, E592-602 (2015).

Khan, S. et al. Autocrine activation of P2Y1 receptors couples Ca2+ influx to Ca2+ release in human pancreatic beta cells. Diabetologia 57, 2535-2545 (2014).

Kobayashi H, Sakahara H, Endo K, Yao Z S, Toyama S, Konishi J. Repeating the avidin "chase" markedly improved the biodistribution of radiolabelled biotinylated antibodies and promoted the excretion of additional background radioactivity. Eur J Cancer. 1995; 31A(10):1689-96.

Kume E, Fujimura H, Matsuki N, Ito M, Aruga C, Toriumi W, et al. Hepatic changes in the acute phase of streptozotocin (SZ)-induced diabetes in mice. Exp Toxicol Pathol. 2004; 55(6):467-80.

Ladriere L, Leclercq-Meyer V, Malaisse W J. Assessment of islet beta-cell mass in isolated rat pancreases perfused with D-[(3)H]mannoheptulose. Am J Physiol Endocrinol Metab. 2001; 281(2):E298-303.

Ladriere L, Malaisse-Lagae F, Alejandro R, Malaisse W J. Pancreatic fate of a (125)I-labelled mouse monoclonal antibody directed against pancreatic B-cell surface ganglioside(s) in control and diabetic rats. Cell Biochem Funct. 2001; 19(2):107-15.

Larsen M O, Gotfredsen C F, Wilken M, Carr R D, Porksen N, Rolin B. Loss of beta-cell mass leads to a reduction of pulse mass with normal periodicity, regularity and entrainment of pulsatile insulin secretion in Gottingen minipigs. Diabetologia. 2003; 46(2):195-202.

Laurent, D. et al. Pancreatic β-cell imaging in humans: fiction or option? Diabetes Obes Metab 18, 6-15 (2015).

Lavoie, E. G. et al. Identification of the ectonucleotidases expressed in mouse, rat, and human Langerhans islets: potential role of NTPDase3 in insulin secretion. American Journal of Physiology—Endocrinology and Metabolism 299, E647-56 (2010).

Liu C B, Liu G Z, Liu N, Zhang Y M, He J, Rusckowski M, et al. Radiolabeling morpholinos with 90Y, 111In, 188Re and 99mTc. Nuclear medicine and biology. 2003; 30(2): 207-14.

Liu G, Dou S, Chen X, Chen L, Liu X, Rusckowski M, et al. Adding a clearing agent to pretargeting does not lower the tumor accumulation of the effector as predicted. Cancer biotherapy & radiopharmaceuticals. 2010; 25(6): 757-62.

Liu G, Dou S, He J, Liu X, Rusckowski M, Hnatowich D J. Predicting the biodistribution of radiolabeled cMORF effector in MORF-pretargeted mice. European journal of nuclear medicine and molecular imaging. 2007; 34(2): 237-46.

Liu G, Dou S, Pretorius P H, Liu X, Chen L, Rusckowski M, et al. Tumor pretargeting in mice using MORF conjugated CC49 antibody and radiolabeled complimentary cMORF effector. Q J Nucl Med Mol Imaging. 2009.

Liu G, He J, Dou S, Gupta S, Rusckowski M, Hnatowich D J. Further investigations of morpholino pretargeting in mice—establishing quantitative relations in tumor. European journal of nuclear medicine and molecular imaging. 2005; 32(9):1115-23.

Liu G, Hnatowich D J. A semiempirical model of tumor pretargeting. Bioconjugate chemistry. 2008; 19(11):2095-104.

Liu G, Liu C, Zhang S, He J, Liu N, Gupta S, et al. Investigations of 99mTc morpholino pretargeting in mice. Nuclear medicine communications. 2003; 24(6):697-705.

Liu G, Mang'era K, Liu N, Gupta S, Rusckowski M, Hnatowich D J. Tumor pretargeting in mice using (99m) Tc-labeled morpholino, a DNA analog. J Nucl Med. 2002; 43(3):384-91.

Liu G, Zhang C, Liu F, Wang R, Fu Z, Li G, et al. 99mTc-N, N'-bis(aminoethyl)propanediamine hexaacetic acid (BPHA): a glomerular filtration agent similar to 99mTc-DTPA. Nuclear medicine and biology. 2002; 29(4):399-404.

Liu G, Zhang S, He J, Zhu Z, Rusckowski M, Hnatowich D J. Improving the labeling of S-acetyl NHS-MAG(3)-conjugated morpholino oligomers. Bioconjugate chemistry. 2002; 13(4):893-7.

Liu, S. & Trapnell, C. Single-cell transcriptome sequencing: recent advances and remaining challenges. F1000Res 5, 1-9 (2016).

Maes F, Collignon A, Vandermeulen D, Marchal G, Suetens P. Multimodality image registration by maximization of mutual information. IEEE transactions on medical imaging. 1997; 16(2):187-98.

Malaisse W J, Doherty M, Ladriere L, Malaisse-Lagae F. Pancreatic uptake of [2-(14)C]alloxan. Int J Mol Med. 2001; 7(3):311-5.

Malaisse W J, Ladriere L. Assessment of B-cell mass in isolated islets exposed to D-[3H]mannoheptulose. Int J Mol Med. 2001; 7(4):405-6.

Malone, J. H. & Oliver, B. Microarrays, deep sequencing and the true measure of the transcriptome. BMC Biol. 9, 34 (2011).

McCulloch D K, Koerker D J, Kahn S E, Bonner-Weir S, Palmer J P. Correlations of in vivo beta-cell function tests with beta-cell mass and pancreatic insulin content in streptozocin-administered baboons. Diabetes. 1991; 40(6):673-9.

Moore A, Bonner-Weir S, Weissleder R. Noninvasive in vivo measurement of beta-cell mass in mouse model of diabetes. Diabetes. 2001; 50(10):2231-6.

Munkonda, M. N. et al. Characterization of a monoclonal antibody as the first specific inhibitor of human NTP diphosphohydrolase-3. FEBS Journal 276, 479-496 (2009).

Nie N H, Hull C H, Jenkins J G, Steinbrenner K, Bent D H. Statistical package for the social sciences. New York: McGraw-Hill. 1975.

Nyman L R, Wells K S, Head W S, McCaughey M, Ford E, Brissova M, et al. Real-time, multidimensional in vivo imaging used to investigate blood flow in mouse pancreatic islets. The Journal of clinical investigation. 2008; 118(11):3790-7.

Olafsen T, Wu A. M. Antibody vectors for imaging. Seminars in nuclear medicine. 2010; 40(3):167-81.

Olafsen, T. & Wu, A. M. Antibody Vectors for Imaging. YSNUC 40, 167-181 (2010).

Otonkoski T, Nanto-Salonen K, Seppanen M, Veijola R, Huopio H, Hussain K, et al. Noninvasive Diagnosis of Focal Hyperinsulinism of Infancy With [18F]-DOPA Positron Emission Tomography. Diabetes. 2006; 55(1): 13-8.

Parnaud, G. et al. Proliferation of sorted human and rat beta cells. Diabetologia 51, 91-100 (2008).

Petit, P., Lajoix, A.-D. & Gross, R. P2 purinergic signalling in the pancreatic β-cell: Control of insulin secretion and pharmacology. European Journal of Pharmaceutical Sciences 37, 67-75 (2009).

Powers A C, Rabizadeh A, Akeson R, Eisenbarth G S. Characterization of monoclonal antibody 3G5 and utilization of this antibody to immobilize pancreatic islet cell gangliosides in a solid phase radioassay. Endocrinology. 1984; 114(4):1338-43.

Rahier J, Guiot Y, Goebbels R M, Sempoux C, Henquin J C. Pancreatic beta-cell mass in European subjects with type 2 diabetes. Diabetes, obesity & metabolism. 2008; 10 Suppl 4:32-42.

RFX6 Regulates Insulin Secretion by Modulating Ca2+ Homeostasis in Human β Cells. Cell Reports 9, 2206-2218 (2014).

Robertson R P. Estimation of beta-cell mass by metabolic tests: necessary, but how sufficient? Diabetes. 2007; 56(10):2420-4.

Robinson, M. D. & Oshlack, A. A scaling normalization method for differential expression analysis of RNA-seq data. Genome Biol. 11, R25 (2010).

Robson, S. C., Sévigny, J. & Zimmermann, H. The E-NTPDase family of ectonucleotidases: Structure function relationships and pathophysiological significance. Purinergic Signal. 2, 409-430 (2006).

Sadoff L. Nephrotoxicity of streptozotocin (NSC-85998). Cancer chemotherapy reports. 1970; 54(6):457-9.

Saito K, Yaginuma N, Takahashi T. Differential volumetry of A, B and D cells in the pancreatic islets of diabetic and nondiabetic subjects. The Tohoku journal of experimental medicine. 1979; 129(3):273-83.

Schmitz A, Shiue C Y, Feng Q, Shiue G G, Deng S, Pourdehnad M T, et al. Synthesis and evaluation of fluorine-18 labeled glyburide analogs as beta-cell imaging agents. Nuclear medicine and biology. 2004; 31(4):483-91.

Schneider S, Feilen P J, Schreckenberger M, Schwanstecher M, Schwanstecher C, Buchholz H G, et al. In vitro and in vivo evaluation of novel glibenclamide derivatives as imaging agents for the non-invasive assessment of the pancreatic islet cell mass in animals and humans. Exp Clin Endocrinol Diabetes. 2005; 113(7):388-95.

Segerstolpe, Å. et al. Single-Cell Transcriptome Profiling of Human Pancreatic Islets in Health and Type 2 Diabetes. Cell Metabolism 24, 593-607 (2016).

Silva, A. M. et al. Electrophysiological and immunocytochemical evidence for P2X purinergic receptors in pancreatic beta cells. Pancreas 36, 279-283 (2008).

Simpson N R, Souza F, Witkowski P, Maffei A, Raffo A, Herron A, et al. Visualizing pancreatic beta-cell mass with [11C]DTBZ. Nuclear medicine and biology. 2006; 33(7): 855-64.

Souza F, Simpson N, Raffo A, Saxena C, Maffei A, Hardy M, et al. Longitudinal noninvasive PET-based beta cell mass estimates in a spontaneous diabetes rat model. The Journal of clinical investigation. 2006; 116(6): 1506-13.

Speier, S. et al. Noninvasive high-resolution in vivo imaging of cell biology in the anterior chamber of the mouse eye. Nat Protoc 3, 1278-1286 (2008).

Speier, S. et al. Noninvasive in vivo imaging of pancreatic islet cell biology. Nature Medicine 14, 574-578 (2008).

Sweet I R, Cook D L, Lernmark A, Greenbaum C J, Krohn K A. Non-invasive imaging of beta cell mass: a quantitative analysis. Diabetes Technol Ther. 2004; 6(5):652-9.

Sweet I R, Cook D L, Lernmark A, Greenbaum C J, Wallen A R, Marcum E S, et al. Systematic screening of potential beta-cell imaging agents. Biochem Biophys Res Commun. 2004; 314(4):976-83.

Syed, S. K. et al. Ectonucleotidase NTPDase3 is abundant in pancreatic β-cells and regulates glucose-induced insulin secretion. American Journal of Physiology—Endocrinology and Metabolism 305, E1319-26 (2013).

Thorel F, Nepote V, Avril I, Kohno K, Desgraz R, Chera S, et al. Conversion of adult pancreatic alpha-cells to beta-cells after extreme beta-cell loss. Nature. 2010; 464 (7292):1149-54.

Trapnell, C., Pachter, L. & Salzberg, S. L. TopHat: discovering splice junctions with RNA-Seq. Bioinformatics 25, 1105-1111 (2009).

Virostko J, Chen Z, Fowler M, Poffenberger G, Powers A C, Jansen E D. Factors influencing quantification of in vivo bioluminescence imaging: application to assessment of pancreatic islet transplants. Mol Imaging. 2004; 3(4):333-42.

Virostko J, Jansen E D, Powers A C. Current status of imaging pancreatic islets. Current diabetes reports. 2006; 6(4):328-32.

Virostko J, Powers A C, Jansen E D. Validation of luminescent source reconstruction using single-view spectrally resolved bioluminescence images. Applied optics. 2007; 46(13):2540-7.

Virostko J, Powers A C. Molecular imaging of the pancreas in small animal models. Gastroenterology. 2009; 136(2): 407-9.

Virostko J, Radhika A, Poffenberger G, Chen Z, Brissova M, Gilchrist J, et al. Bioluminescence imaging in mouse models quantifies beta cell mass in the pancreas and after islet transplantation. Mol Imaging Biol. 2010; 12(1):42-53.

Virostko J, Xie J, Hallahan D E, Arteaga C L, Gore J C, Manning H C. A molecular imaging paradigm to rapidly profile response to angiogenesis-directed therapy in small animals. Mol Imaging Biol. 2009; 11(3):204-12.

Wangler B, Schneider S, Thews O, Schirrmacher E, Comagic S, Feilen P, et al. Synthesis and evaluation of (S)-2-(2-[18F]fluoroethoxy)-4-([3-methyl-1-(2-piperidin-1-yl-phenyl)-butyl-carbamoyl]-methyl)-benzoic acid ([18F]repaglinide): a promising radioligand for quantification of pancreatic beta-cell mass with positron emission tomography (PET). Nuclear medicine and biology. 2004; 31(5):639-47.

Wu A M. Antibodies and antimatter: the resurgence of immuno-PET. J Nucl Med. 2009; 50(1):2-5.

Wuttke, A., Idevall-Hagren, O. & Tengholm, A. P2Y1 receptor-dependent diacylglycerol signaling microdomains in β cells promote insulin secretion. FASEB J 27, 1610-1620 (2013).

Xin, Y. et al. RNA Sequencing of Single Human Islet Cells Reveals Type 2 Diabetes Genes. Cell Metabolism 24, 608-615 (2016).

Zimmermann, H., Zebisch, M. & Strater, N. Cellular function and molecular structure of ectonucleotidases. Purinergic Signal. 8, 437-502 (2012).

D. SEQUENCES

SEQ ID NO: 1 CD39L3 amino acid sequence
MFTVLTRQPCEQAGLKALYRTPTIIALVVLLVSIVVLVSITVIQIHKQEV
LPPGLKYGIVLDAGSSRTTVYVYQWPAEKENNTGVVSQTFKCSVKGSGIS
SYGNNPQDVPRAFEECMQKVKGQVPSHLHGSTPIHLGATAGMRLLRLQNE
TAANEVLESIQSYFKSQPFDPRGAQIISGQEEGVYGWITANYLMGNFLEK
NLWHMWVHPHGVETTGALDLGGASTQISFVAGEKMDLNTSDIMQVSLYGY
VYTLYTHSFQCYGRNEAEKKFLAMLLQNSPTKNHLTNPCYPRDYSISFTM
GHVFDSLCTVDQRPESYNPNDVITFEGTGDPSLCKEKVASIFDFKACHDQ
ETCSFDGVYQPKIKGPFVAFAGFYYTASALNLSGSFSLDTFNSSTWNFCS
QNWSQLPLLLPKFDEVYARSYCFSANYIYHLFVNGYKFTEETWPQIHFEK
EVGNSSIAWSLGYMLSLTNQIPAESPLIRLPIEPPVFVGTLAFFTAAALL
CLAFLAYLCSATRRKRHSEHAFDHAVDSD SEQ ID NO: 2 CD39L3 nucleic acid sequence
ACCCACGCGTCTGGCCGCGGGCCGCCTCTGCGGCAGCGCTAGTCGCCTTC
TCCGAATCGGCTCCGCACAGCTAGGAGAAAAGATGTTCACTGTGCTGACC
CGCCAACCATGTGAGCAAGCAGGCCTCAAGGCCCTCTACCGAACTCCAAC
CATCATTGCCTTGGTGGTCTTGCTTGTGAGTATTGTGGTACTTGTGAGTA
TCACTGTCATCCAGATCCACAAGCAAGAGGTCCTCCCTCCAGGACTGAAG
TATGGTATTGTGCTGGATGCCGGGTCTTCAAGAACCACAGTCTACGTGTA
TCAATGGCCAGCAGAAAAAGAGAATAATACCGGAGTGGTCAGTCAAACCT
TCAAATGTAGTGTGAAAGGCTCTGGAATCTCCAGCTATGGAAATAACCCC
CAAGATGTCCCCAGAGCCTTTGAGGAGTGTATGCAAAAAGTCAAGGGGCA
GGTTCCATCCCACCTCCACGGATCCACCCCCATTCACCTGGGAGCCACGG
CTGGGATGCGCTTGCTGAGGTTGCAAAATGAAACAGCAGCTAATGAAGTC
CTTGAAAGCATCCAAAGCTACTTCAAGTCCCAGCCCTTTGACTTTAGGGG
TGCTCAAATCATTTCTGGGCAAGAAGAAGGGGTATATGGATGGATTACAG
CCAACTATTTAATGGGAAATTTCCTGGAGAAGAACCTGTGGCACATGTGG
GTGCACCCGCATGGAGTGGAAACCACGGGTGCCCTGGACTTAGGTGGTGC
CTCCACCCAAATATCCTTCGTGGCAGGAGAGAAGATGGATCTGAACACCA
GCGACATCATGCAGGTGTCCCTGTATGGCTACGTATACACGCTCTACACA
CACAGCTTCCAGTGCTATGGCCGGAATGAGGCTGAGAAGAAGTTTCTGGC
AATGCTCCTGCAGAATTCTCCTACCAAAAACCATCTCACCAATCCCTGTT
ACCCTCGGGATTATAGCATCAGCTTCACCATGGGCCATGTATTTGATAGC
CTGTGCACTGTGGACCAGAGGCCAGAAAGTTATAACCCCAATGATGTCAT
CACTTTTGAAGGAACTGGGGACCCATCTCTGTGTAAGGAGAAGGTGGCTT
CCATATTTGACTTCAAAGCTTGCCATGATCAAGAAACCTGTTCTTTTGAT
GGGGTTTATCAGCCAAAGATTAAAGGGCCATTTGTGGCTTTTGCAGGATT
CTACTACACAGCCAGTGCTTTAAATCTTTCAGGTAGCTTTTCCCTGGACA
CCTTCAACTCCAGCACCTGGAATTTCTGCTCACAGAATTGGAGTCAGCTC
CCACTGCTGCTCCCCAAATTTGATGAGGTATATGCCCGCTCTTACTGCTT
CTCAGCCAACTACATCTACCACTTGTTTGTGAACGGTTACAAATTCACAG
AGGAGACTTGGCCCCAAATACACTTTGAAAAAGAAGTGGGGAATAGCAGC
ATAGCCTGGTCTCTTGGCTACATGCTCAGCCTGACCAACCAGATCCCAGC
TGAAAGCCCTCTGATCCGTCTGCCCATAGAACCACCTGTCTTTGTGGGCA
CCCTCGCTTTCTTCACAGTGGCAGCCTTGCTGTGTCTGGCATTTCTTGCA
TACCTGTGTTCAGCAACCAGAAGAAAGAGGCACTCCGAGCATGCCTTTGA
CCATGCAGTGGATTCTGACTGAGCCTTCAAAGCAGCTCCTGGAGTCCAAT
GGCTGCTTAGAGTCAGCCTGGGTGGCACCAGGCAATGCAGGTGAAGTGGC
TGCCTTCAGGAAATACAACTAACTAAAATCAAACACCTAGGTCACGTGCC
TCTCAAATACTGATTTCTGCCACAGCACCTCTTGAGGCATCCCCTTGGCTA
TTCTGTGCATATTGTTCTTCAGAGACCTCACTACCCACATGCTGATCTAT
TGGGGAACAGAGAAGAGACAGGCCACTAAGGTCAGGCTCTTTATATTAAG
TTCCCCAGAGGAAGAGTAAGTTGAGAAGGTATCAGTTTAATGTTGAAGAA
TTGACCTCAGGGCTCAGTTTCCATTTCCCTCCCTCAGTATTCTTCCTGGC
AAGATACCCATTAAGCATTTCGCCAATCAGAATCTCATTTTATAGTTTTT
CCCATTGGTCTTTAACTAAGACTTTCTTGTAGCAATCTCGTAAGCAGTGA
ACCCCCTCAGATCAGTAGAATATAGTATCTGGGGGAGAAGACTTACTTCC
TTCAGGGCAGCAGCCACAGCCAGGCTTCTGTCATACAGGTAGATCCCGAA
GCACAGAGACATAAAAAAGGTCTCCCAGAAAACTATAGACCATTCTCCAA
GTGGAATTCCCACTTAGGGCTCTGGTCACTAGATTGCAACCTGTGTGTTT
GTCATCATCCTCATCTCACCATTGTATTGCTATGCCCTCCCATAAAAACA
CATTGATCCCTAGCAAGATTATTGCATTCCAGATTTTACTGCCTTTGCTA
GGCTTTTGCTTAGCAAAGGGCTGACTTTCCATTGTTATCATGGTGTATAT
ATTTTTGTCACCATTCCCACAAGTATACTTGATGTTGTCATAGAACGAAC
ATCCTACTCTATGATTTACTAACCAATTACTTTCCCAGATCATAGACCTC
TCTGCATAGTAGTCATAGGTCTTGACTTTGGGGAAAGAAAAGGAAGCTGC
AGGAATATTTATCTCCAAAGTCGAATGAGAAAGAACTCCAGCAAATCCAA
TGGCTACAAACTAAAAATCAGCATTATTTCATATTGCTGTTTCTTAGCTG
AATATGGAATAAAGAACTATTATTTTATTTTGAAAAAAAAAAAAAAA

What is claimed is:

1. A method of treating diabetes in a subject comprising
   a) contacting pancreatic tissue from a recipient subject with a fluorescently labeled anti-CD39L3 antibody or magnetic beads conjugated to an anti-CD39L3 antibody, wherein the anti-CD39L3 antibody binds to CD39L3 expressed on islet β-cells from the pancreatic tissue;
   b) assaying the amount of islet β-cell-bound anti-CD39L3 antibody relative to a nondiabetic control, wherein a decrease in islet β-cell-bound anti-CD39L3 antibody indicates reduced islet β-cell mass in the pancreatic tissue and indicates that the recipient subject has diabetes;
   c) obtaining a pancreatic tissue sample from a donor;
   d) contacting the pancreatic tissue sample from the donor with a fluorescently labeled anti-CD39L3 antibody or magnetic beads conjugated to an anti-CD39L3 antibody, wherein the anti-CD39L3 antibody binds to CD39L3 expressed on islet β-cells from the pancreatic tissue sample;
   e) isolating the CD39L3 expressing islet β-cells from the donor in step d) using magnetic beads or fluorescence activated cell sorting; and
   f) transferring the isolated CD39L3 expressing islet β-cells from the donor to the recipient subject with diabetes.

2. The method of treating diabetes of claim 1, wherein the pancreatic tissue is a pancreatic tissue sample obtained from the recipient and wherein the contacting of the recipient pancreatic tissue with the anti-CD39L3 antibody and assaying the level of islet β-cell-bound anti-CD39L3 antibody occurs ex vivo.

3. The method of treating diabetes of claim 1, wherein the pancreatic tissue is contacted with the anti-CD39L3 antibody in vivo and the amount of islet β-cell-bound anti-CD39L3 antibody is detected using bioluminescence imaging (BLI) magnetic resonance imaging, positron emission tomography (PET), single photon emission computed tomography (SPECT), computed tomography (CT) scanning, or fluorescence molecular tomography (FMT).

* * * * *

UNITED STATES PATENT AND TRADEMARK OFFICE
CERTIFICATE OF CORRECTION

| | |
|---|---|
| PATENT NO. | : 11,287,427 B2 |
| APPLICATION NO. | : 16/620747 |
| DATED | : March 29, 2022 |
| INVENTOR(S) | : Alvin C. Powers et al. |

It is certified that error appears in the above-identified patent and that said Letters Patent is hereby corrected as shown below:

In the Specification

In Column 1, Line 14, before the "BACKGROUND" section, please insert the following new paragraph:
--STATEMENT OF GOVERNMENT SUPPORT
This invention was made with government support under Grant Number DK094199, awarded by the National Institutes of Health. The Government has certain rights in the invention.--

Signed and Sealed this
Seventeenth Day of September, 2024

Katherine Kelly Vidal
*Director of the United States Patent and Trademark Office*